United States Patent
Brittain et al.

(10) Patent No.: US 9,603,939 B2
(45) Date of Patent: Mar. 28, 2017

(54) PLATFORM DRUG DELIVERY SYSTEM UTILIZING CRYSTAL ENGINEERING AND THEANINE DISSOLUTION

(71) Applicant: THEAPRIN PHARMACEUTICALS INC., Hauppauge, NY (US)

(72) Inventors: Harry G. Brittain, Milford, NJ (US); Philip V. Felice, Smithtown, NY (US)

(73) Assignee: THEAPRIN PHARMACEUTICALS INC., Hauppauge, NY (US)

( * ) Notice: Subject to any disclaimer, the term of this patent is extended or adjusted under 35 U.S.C. 154(b) by 0 days.

(21) Appl. No.: 15/097,681

(22) Filed: Apr. 13, 2016

(65) Prior Publication Data

US 2016/0263138 A1   Sep. 15, 2016

Related U.S. Application Data

(62) Division of application No. 14/642,191, filed on Mar. 9, 2015.

(51) Int. Cl.
| | |
|---|---|
| A61K 47/18 | (2006.01) |
| A61K 47/48 | (2006.01) |
| A61K 31/704 | (2006.01) |
| A61K 31/13 | (2006.01) |
| A61K 31/137 | (2006.01) |
| A61K 31/192 | (2006.01) |
| A61K 31/198 | (2006.01) |
| A61K 31/277 | (2006.01) |
| A61K 31/4045 | (2006.01) |
| A61K 31/4164 | (2006.01) |
| A61K 31/4196 | (2006.01) |
| A61K 31/426 | (2006.01) |

(Continued)

(52) U.S. Cl.
CPC ........ *A61K 47/48038* (2013.01); *A61K 31/13* (2013.01); *A61K 31/137* (2013.01); *A61K 31/192* (2013.01); *A61K 31/198* (2013.01); *A61K 31/277* (2013.01); *A61K 31/4045* (2013.01); *A61K 31/4164* (2013.01); *A61K 31/4196* (2013.01); *A61K 31/426* (2013.01); *A61K 31/43* (2013.01); *A61K 31/445* (2013.01); *A61K 31/4745* (2013.01); *A61K 31/48* (2013.01); *A61K 31/496* (2013.01); *A61K 31/4985* (2013.01); *A61K 31/506* (2013.01); *A61K 31/522* (2013.01); *A61K 31/536* (2013.01); *A61K 31/545* (2013.01); *A61K 31/546* (2013.01); *A61K 31/549* (2013.01); *A61K 31/573* (2013.01); *A61K 31/635* (2013.01); *A61K 31/704* (2013.01); *A61K 31/7048* (2013.01); *A61K 31/7072* (2013.01); *A61K 38/12* (2013.01); *A61K 47/183* (2013.01)

(58) Field of Classification Search
None
See application file for complete search history.

(56) References Cited

PUBLICATIONS

Brittain, Harry G., "Pharmaceutical cocrystals: the coming wave of new drug substances." J. Pharm. Sci. (2013) 102 p. 311-317.*

(Continued)

*Primary Examiner* — Fred Reynolds
(74) *Attorney, Agent, or Firm* — Notaro, Michalos & Zaccaria P.C.

(57) ABSTRACT

A method of treating Hodgkin's disease in a subject. The method involves administering to the subject an effective amount of a water-soluble composition which includes a cocrystal composition containing doxorubicin and a theanine enantiomer.

3 Claims, 34 Drawing Sheets

Scattering Angle (degrees 2θ)

Wavenumber (cm⁻¹)

(51) Int. Cl.
*A61K 31/43* (2006.01)
*A61K 31/445* (2006.01)
*A61K 31/4745* (2006.01)
*A61K 31/48* (2006.01)
*A61K 31/496* (2006.01)
*A61K 31/4985* (2006.01)
*A61K 31/506* (2006.01)
*A61K 31/522* (2006.01)
*A61K 31/536* (2006.01)
*A61K 31/545* (2006.01)
*A61K 31/546* (2006.01)
*A61K 31/549* (2006.01)
*A61K 31/573* (2006.01)
*A61K 31/635* (2006.01)
*A61K 31/7048* (2006.01)
*A61K 31/7072* (2006.01)
*A61K 38/12* (2006.01)

(56) References Cited

PUBLICATIONS

Sekhon, B. S., "Pharmaceutical cocrystals—a review." Ars. Pharm. (2009) 50(3) p. 99-117.*

* cited by examiner

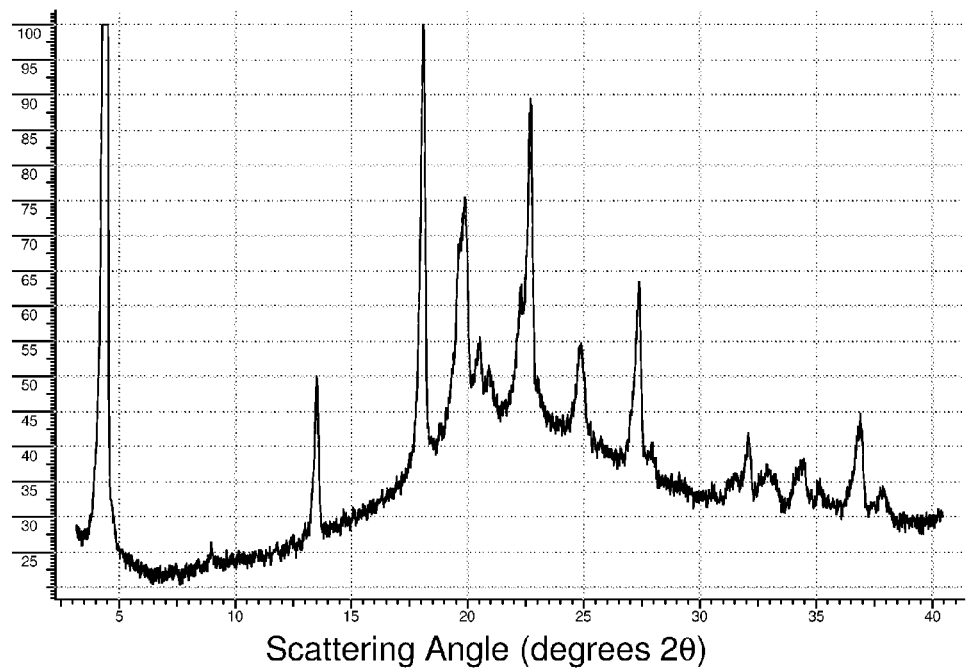
Figure 9a
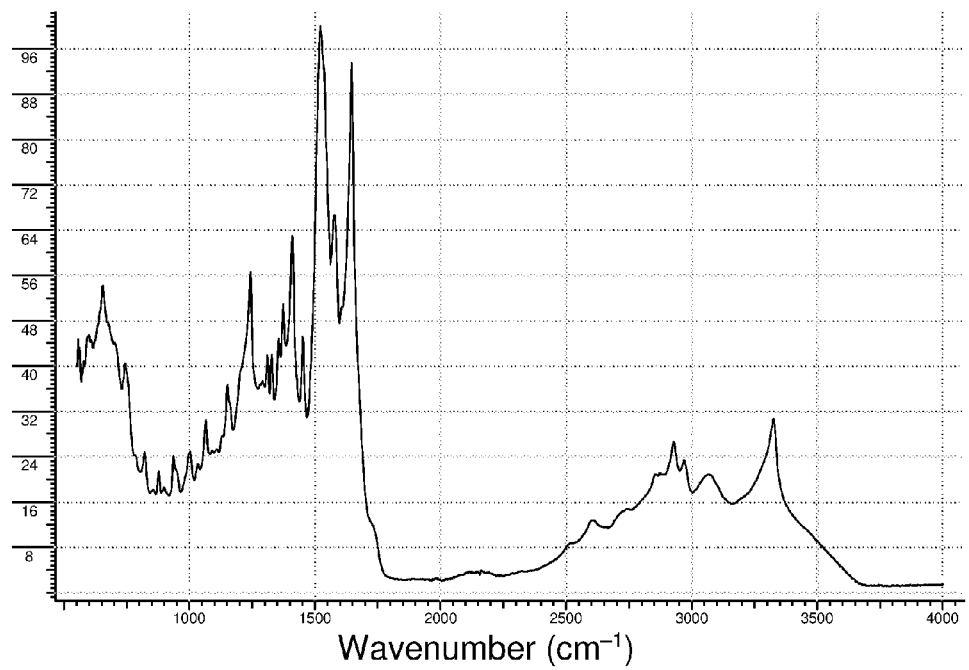
Figure 9b: Infrared absorption spectrum of the L-theanine/daptomycin cocrystal.

PLATFORM DRUG DELIVERY SYSTEM UTILIZING CRYSTAL ENGINEERING AND THEANINE DISSOLUTION

CROSS-REFERENCE TO RELATED APPLICATION

This is a divisional of application Ser. No. 14/642,191, filed Mar. 9, 2015, which is incorporated herein by reference.

FIELD AND BACKGROUND OF THE INVENTION

Field of the Invention

The present invention relates to a platform drug delivery system and, more specifically, to a novel method of improving the delivery of low solubility pharmaceuticals utilizing crystal engineering and Theanine dissolution resulting in enhanced bioactivity, dissolution rate, and solid state stability.

Background of the Invention

There are clear unmet needs in the pharmaceutical industry and medical community to improve drug delivery and improve the clinical status of the patient more rapidly. Therapeutic compounds are most stable in a crystalline form, but can display slow dissolution rates resulting in reduced bioavailability of the active pharmaceutical ingredient, thereby slowing absorption. The ongoing interest in modification of drug substances whose physical properties are less than desirable has led to significant study of issues associated with polymorphism and solvatomorphism. More recently, it has been recognized that many substances may cocrystallize in a single continuous lattice structure, leading pharmaceutical scientists into new areas of crystal engineering. Cocrystals are mixed crystals where the cocrystal is a structurally homogeneous crystalline material that has been formed from discrete neutral molecular species that are solids at ambient temperatures.

Cocrystals represent novel forms of drug substances that would be suitable for incorporation in pharmaceutical solid dosage forms, and should enable formulation scientists to overcome a variety of problems that are encountered during development of traditional formulations. One could consider cocrystals as being an alternative to polymorphs, solvatomorphs, and salts, and cocrystals represent a different approach to solve problems related to dissolution, crystallinity, hygroscopicity, etc. The most important improvement that might accompany the formation of a cocrystal would be an enhancement in the solubility of the drug substance, or at least a faster degree of dissolution.

The recently disclosed cocrystal system formed by aspirin (acetylsalicylic acid) and theanine (5-N-ethyl-glutamine) amply demonstrates the potential advantages that can be achieved. Although several new pharmaceutical cocrystals have been advanced into preclinical and clinical studies, further advances are needed to address the increasing complexity of new drug candidates. Unfortunately, it is not yet possible to predict whether two substances will cocrystallize or not, and therefore cocrystal screening studies are largely empirical in nature.

The cocrystal of Theanine is a general form which can be translated to other ion containing drugs. This makes it very attractive to the pharmaceutical industry for the following reasons: drug companies want to know that there are pipeline possibilities for other new products, creates a defensive measure for an existing branded pharmaceutical against generic introduction, and expands indications for a low solubility branded pharmaceutical.

Crystallization and Theanine dissolution of low solubility pharmaceuticals is paramount in the treatment of patients presenting with a wide variety of emergent conditions where improved drug delivery would be of benefit.

The harmful effect of glutamate upon the CNS were first observed in 1954 by T. Hayashi, a Japanese scientist who noted that direct application of glutamate to the CNS caused seizure activity (Wikipedia, "Excitotoxicity". March, 2012. http://en.wikipedia.org/wiki/Excitotoxicity). Excitotoxicity is the pathological process by which nerve cells are damaged and killed by excessive stimulation by neurotransmitters such as glutamate and similar substances. This occurs when receptors for the excitatory neurotransmitter glutamate (glutamate receptors) such as the NMDA receptor (N-methyl-D-aspartate receptor) and AMPA receptor (α-amino-3-hydroxy-5-methyl-4-isoxazolepropionic acid receptor) are overactivated by glutamatergic storm (Wikipedia, "Excitotoxicity" March, 2012 http://en.wikipedia.org/wiki/Excitotoxicitv). Excitotoxins like NMDA and kainic acid which bind to these receptors, as well as pathologically high levels of glutamate, can cause excitotoxicity by allowing high levels of calcium ions ($Ca^{2+}$) to enter the cell (Manev, H.; Favaron, M.; Guidotti, A.; and Costa, E., Delayed increase of $Ca^{2+}$ influx elicited by glutamate: role in neuronal death. *Molecular Pharmacoloy.* 1989 July; 36(1):106-112)). $Ca^{2+}$ influx into cells activates a number of enzymes, including phospholipases, endonucleases, and proteases such as calpain. These enzymes go on to damage cell structures such as components of the cytoskeleton, membrane, and DNA. Normally, glutamate concentration inside the cells is 10,000 times greater than outside the cell (Teichberg, Vivian., and Vikhanski, Luba. "Protecting the Brain from a Glutamate Storm." The DANA Foundation. Thursday, May 10, 2007). Increased extracellular glutamate levels leads to the activation of $Ca^{2+}$ permeable NMDA receptors on myelin sheaths and oligodendrocytes, leaving oligodendrocytes susceptible to $Ca^{2+}$ influxes and subsequent excitotoxicity (Nakamura et al, "S-nitrosylation of Drp1 links excessive mitochondrial fission to neuronal injury in neurodegeneration" *Mitochondrion,* 2010 August; 10(5):573-8; Dutta et al. (January 2011). "Mechanisms of neuronal dysfunction and degeneration in multiple sclerosis". *Prog Neurobiol* 93 (1): 1-12). Excitotoxicity may be involved in spinal cord injury, stroke, traumatic brain injury, multiple sclerosis, Alzheimer's disease, Parkinson's disease, alcoholism, alcohol withdrawal, over-rapid benzodiazepine withdrawal, and Huntington's disease (Wikipedia, "Excitotoxicity". March, 2012. http://en.wikipedia.org/wiki/Excitotoxicity; Kim, A. H.; Kerchner, G. A.; and Choi, D. W., "Blocking Excitotoxicity or Glutamatergic Storm." *CNS Neuroproteciton.* Marcoux, Chap 1. Springer, New York. 2002. pp. 3-36; Hughes, J. R., "Alcohol withdrawal seizures". *Epilepsy Behav* 15 (2): 92-7) (February 2009)). Toxicity from excess glutamate is also thought to be a component of other conditions as diverse as hypoglycemia, damage to a newborns brain caused by interrupted oxygen supply during delivery, exposure to nerve gas, and is probably involved in chronic nerve damage in such conditions as glaucoma, amyotrophic lateral sclerosis, and HIV dementia (Teichberg, Vivian, and Vikhanski, Luba. "Protecting the Brain from a Glutamate Storm." The DANA Foundation. Thursday, May 10, 2007).

Theanine is extremely safe, with a $LD_{50}$ toxicity of >5000 mg/kg in humans ("L-Theanine". www.drugs.com/npp/l-theanine.html). Theanine may protect against nerve cell damage by blocking glutamine entrance to cells due to the similarity in stereochemical structures of Theanine and glutamine. (Kakuda T, et al., "Protective effect of gamma-glutamylethylamide (Theanine) on ischemic delayed neuronal death in gerbils," *Neuroscience Letters* 2000; 289(3): 189-192). GABA (Gamma-Aminobutyric Acid) is the most widespread inhibitory neurotransmitter of the brain. When GABA levels are decreased there is an augmentation of nerve impulses in the neuron. Theanine increases GABA levels in the brain, opposing excess stimulation of nerve impulses by excitatory neurotransmitters.

As such, crystal engineering and Theanine dissolution may be useful in the prevention and treatment of diseases or conditions associated with glutamate toxicity, decreased glutathione levels, decreased GABA levels, neuronal damage or death from neurotransmitter excitotoxicity, amyloid beta-induced neurotoxicity, neurotoxins and oxidative stress inducers that damage the nervous system. Theanine crosses the blood-brain barrier via leucine-preferring transport system (Yokogoshi, Hidehiko; Kobayashi, Miki; Mochizuki, Mikiko; and Terashima, Takehiko, "Effect of Theanine, r-Glutamylethylamide, on Brain Monoamines and Striatal Dopamine Release in Conscious Rats." *Neurochemical Research*, May 1998, Volume 23, Issue 5, pp. 667-673). The protective effect of L-Theanine against aluminum-induced neurotoxicity was shown by Sumathi et al., 2014. The study clearly indicates the potential of L-Theanine in counteracting the damage inflicted by aluminum on rat brain regions (Sumathi, T.; Shobana, C.; Thangarajeswari, M.; Usha, R. "Protective effect of L-Theanine against aluminum-induced neurotoxicity in cerebral cortex, hippocampus and cerebellum of rat brain-histopathological, and biochemical approach." *Drug Chem Toxicol* Mar. 24, 2014). Several environmental neurotoxins and oxidative stress inducers are known to damage the nervous system and are considered major factors associated with the selective vulnerability of nigral dopaminergic neurons in Parkinson's disease (Cho, H. S.; Kim S.; Lee S. Y.; Park J. A.; Kim S. J.; Chun H. S.; "Protective effect of the green tea component, L-Theanine on environmental toxins-induced neuronal cell death." *Neurotoxicology*. 2008 July; 29(4):656-62). Cho et al., analyzed L-Theanine's capabilities to protect DNA in cells from environmental toxins. The researchers used the human dopaminergic cell line SH-SY5Y, and subjected the cell line to the neurotoxins rotenone and dieldrin. There were a variety of benefits found in the cell cultures that were also treated or pre-treated with L-Theanine, namely, decreased DNA fragmentation and apoptotic cell death. Yet, L-Theanine protected brain-derived neurotrophic factor (BDNF) and glial cell line-derived neurotrophic factor (GDNF) production in the cells (Biohacks Blog, "L-Theanine Attenuates Beta-Amyloid Plaque Neurotoxicity and Neuronal Cell Death."). The authors claim that L-Theanine directly provides neuroprotection against Parkinson's disease-related neurotoxicants and may be clinically useful for preventing Parkinson's disease symptoms (Cho, H. S.; Kim S.; Lee S. Y.; Park J. A.; Kim S. J.; Chun H. S., "Protective effect of the green tea component, L-Theanine on environmental toxins-induced neuronal cell death." *Neurotoxicology*. 2008 July; 29(4):656-62). Di et al., showed that L-Theanine protects the APP (Swedish Mutation) transgenic SH-SY5Y cell against glutamate-induced excitotoxicity via inhibition of the NMDA receptor pathway (Di X., et al., "L-Theanine Projects The APP (Swedish Mutation) Transgenic SH-SY5Y Cell Against Glutamate-Induced Exitotoxicity via Inhibition of the NMDA Receptor Pathway." *Neuroscience* 168 (2010) 778-786). Memantine a glutamate antagonist, decreases glutamate's effect by blocking the NMDA receptor. As well, present inventor H. G. Brittain has shown that Memantine does form a cocrystal with Theanine which may be useful in the prevention and treatment of diseases or conditions associated with glutamate toxicity. The present invention satisfies these and other medical needs and overcomes deficiencies found in the prior art.

A new study that identifies the cause of Alzheimer's disease, dementia, and Parkinson's disease as the breakdown in function of the tau protein in nerve cells and shows that a drug that is presently approved can reverse the memory loss associated with the diseases was reported in the Oct. 31, 2014, edition of the journal *Molecular Neurodegeneration* (Hamaker, Paul. "New research points to tau protein malfunction as cause of Alzheimer's." Nov. 2, 2004). This is the first time that research has proven that the loss of tau protein function precedes the formation of beta-amyloid plaques in Alzheimer's disease. Dr. Charbel Moussa, professor of neuroscience at Georgetown University Medical Center, and colleagues made the discovery (Hamaker, Paul. "New research points to tau protein malfunction as cause of Alzheimer's." Nov. 2, 2004). Cell death is the result of the accumulation of nonfunctional tau protein and beta-amyloid plaques in the nerve cells. The introduction of functional tau protein into nerve cells that had a loss of tau protein restored the normal nerve function. The discovery explains why some people can have beta-amyloid plaques and suffer no memory loss or nerve damage (Hamaker, Paul. "New research points to tau protein malfunction as cause of Alzheimer's." Nov. 2, 2004). Nilotinib was found to assist in the restoration of nerve function in cells that had some tau protein in them (Hamaker, Paul. "New research points to tau protein malfunction as cause of Alzheimer's." Nov. 2, 2004). The present invention satisfies these and other medical needs and overcomes deficiencies found in the prior art.

Glutathione is the liver's first-line defense against drugs and chemicals. It is used by cancer cells against drugs and chemicals. Cancer cells use glutathione to detoxify doxorubicin and escort the drug out of cells. Theanine is able to interfere with this process due to its structural similarity to glutamate. Glutamic acid, or glutamate, is one of the components of glutathione, the drug detoxifier. Because it looks like glutamic acid, cancer cells take up and mistakenly use the Theanine to create glutathione. But the glutathione they create with Theanine does not detoxify like natural glutathione. Instead, this Theanine-based glutathione appears to block the ability of cancer cells to detoxify. Further, in addition to enhancing doxorubicin's cancer-killing effects without harming healthy tissue, Theanine also keeps doxorubicin out of healthy tissue. This is a major added benefit, since one of the drawbacks of the use of doxorubicin is its toxicity to the heart. The potential of Theanine as an adjunct to cancer chemotherapy was proposed by researcher Yasuyuki Sadzuka, who confirmed that Theanine, a major amino acid in green tea, enhances the antitumor activity of doxorubicin (DOX) without an increase in DOX-induced side effects. He postulated that the action of Theanine is due to decreases in glutamate uptake via inhibition of the glutamate transporter and reduction of glutathione and DOX export from the cell. Theanine enhances the antitumor activity not only of DOX but also of cisplatin and irinotecan. In essence, Sadzuka found that Theanine could block the export of doxorubicin (Adriamycin) from cancer cells by blocking the glutamate and glutathione transporter mechanisms. The elevated level of the drug within cancer cells strongly inhibits the tumor. (Sadzuka Y, et al., "The effects of Theanine, as a novel biochemical modulator, on the antitumor activity of Adriamycin." *Cancer Letters* 1996;

105(2):203-209; Sadzuka Y, et al., "Modulation of cancer chemotherapy by green tea." *Clinical Cancer Research* 1998; 4(1): 153-156; Sadzuka Y, et al., "Efficacies of tea components on doxorubicin induced antitumor activity and reversal of multidrug resistance." *Toxicology Letters* 2000; 114(1-3): 155-162; Sadzuka Y, et al., "Improvement of idarubicin induced antitumor activity and bone marrow suppression by Theanine, a component of tea." *Cancer Letters* 2000; 158(2): 119-24; Sadzuka Y, et al., "Enhancement of the activity of doxorubicin by inhibition of glutamate transporter." *Toxicology Letters* 2001; 123(2-3): 159-67; Sadzuka Y, et al., "Effect of dihydrokainate on the antitumor activity of doxorubicin." *Cancer Letters* 2002; 179(2): 157-163). The present invention satisfies these and other medical needs and overcomes deficiencies found in the prior art.

The box jellyfish (Chironex fleckeri) live primarily in coastal waters of northern Australia and throughout the Indo-Pacific. (Box Jellyfish, Box Jellyfish Pictures, Box Jellyfish Facts. *National Geographic*. 1996-2014; Nation). Australian box jellyfish stings can cause acute cardiovascular collapse and death. Yanagihara and Shohet developed methods to recover venom with high specific activity, and evaluated the effects of both total venom and constituent porins at doses equivalent to lethal envenomation. Marked potassium release occurred within 5 min and hemolysis within 20 min in human red blood cells (RBC) exposed to venom or purified venom porin. (Yanagihara, A. A.; Shohet, R. V.; "Cubozoan Venom-Induced Cardiovascular Collapse Is Caused by Hyperkalemia and Prevented by Zinc Gluconate in Mice." *PLoS ONE*, 2012; 7 (12)). Electron microscopy revealed abundant, 12-nm transmembrane pores in RBC exposed to purified venom porins. C57BL/6 mice injected with venom showed rapid decline in ejection fraction with progression to electromechanical dissociation and electrocardiographic findings consistent with acute hyperkalemia. (Yanagihara, A. A.; Shohet, R. V.; "Cubozoan Venom-Induced Cardiovascular Collapse Is Caused by Hyperkalemia and Prevented by Zinc Gluconate in Mice." *PLoS ONE*, 2012; 7 (12)). Recognizing that porin assembly can be inhibited by zinc, Yanagihara and Shohet found that zinc gluconate inhibited potassium efflux from RBC exposed to total venom or purified porin, and prolonged survival time in mice following venom injection. These findings suggest that hyperkalemia is the critical event following Chironex fleckeri envenomation and that rapid administration of zinc could be lifesaving in human sting victims. (Yanagihara, A. A.; Shohet, R. V.; "Cubozoan Venom-Induced Cardiovascular Collapse Is Caused by Hyperkalemia and Prevented by Zinc Gluconate in Mice." *PLoS ONE*, 2012; 7 (12)). Since the current box jellyfish antivenom is not very effective, there is a clear unmet need in the medical community for a novel method of improving the drug delivery of an intravenous zinc gluconate formulation utilizing crystal engineering and Theanine dissolution. The present invention satisfies these and other medical needs and overcomes deficiencies found in the prior art.

Malignant hyperthermia is a hypermetabolic disorder of skeletal muscle that is triggered in susceptible individuals (inherited as an autosomal dominant disorder) by several inhalation anesthetic agents (sevoflurane, desflurane, isoflurane, halothane, enflurane, and methoxyflurane) and succinylcholine. (Akif. "Malignant Hyperthermia." *Anesthesia General*, Feb. 11, 2011). These anesthetic triggers cause intracellular hypercalcemia in skeletal muscle by decreasing the uptake of calcium by the sarcoplasmic reticulum. The intracellular hypercalcemia activates metabolic pathways that result in adenosine triphosphate (ATP) depletion, acidosis, membrane destruction, and ultimately cell death. (Akif. "Malignant Hyperthermia." *Anesthesia General*, Feb. 11, 2011). Core body temperature may reach as high as 112° F. Possible complications of malignant hyperthermia includes amputation, rhabdomyolysis, compartment syndrome, disseminating intravascular coagulation, arrhythmias, renal failure, metabolic acidosis, respiratory acidosis, myopathy, and death. (Heller, J. L. "Malignant Hyperthermia." *Medline Plus*, US National Library of Medicine, Apr. 5, 2013). If malignant hyperthermia is not recognized and treated immediately during surgery, cardiac arrest may ensue. Dantrolene sodium which acts by inhibiting the release of calcium from the sarcoplasmic reticulum is the only medication that is currently approved for the treatment of malignant hyperthermia. Application of a platform drug delivery system utilizing crystal engineering and Theanine dissolution with Dantrolene sodium is paramount, since improved drug delivery would benefit the patient and reduce or prevent the severe complications of this hypermetabolic disorder of skeletal muscle. The present invention satisfies these and other medical needs and overcomes deficiencies found in the prior art.

The beneficial effects of the triptans in patients with migraine are related their multiple mechanisms of actions at sites implicated in the pathophysiology of migraine. These mechanisms are mediated by 5-HT (1B/1 D) receptors and include vasoconstriction of painfully dilated cerebral blood vessels, inhibition of the release of vasoactive neuropeptides by trigeminal nerves, and inhibition of nociceptive neurotransmission (Tepper, S. J.; Rapoport, A. M.; Sheftell, F. D. "Mechanisms of Action of the 5-HT 1B/1D Receptor Agonists." *Arch Neurol*. 2002 July; 59(7): 1084-8). Sumatriptan is indicated for the acute treatment of migraine with or without aura in adults. It is known that large doses of sumatriptan can cause sulfhemoglobinemia, a rare condition in which the blood changes from red to greenish-black, due to the integration of sulfur into the hemoglobin molecule (Patient Bleeds Dark Green Blood." *BBC News*. Jun. 8, 2007). Serious cardiac events, including some that has been fatal, have occurred following the use of sumatriptan tablets and have included ventricular tachycardia, ventricular fibrillation, coronary artery vasospasm, myocardial ischemia, and myocardial infarction (Sumatriptan—FDA Prescribing Information, Side Effects and Uses." January 2014). Application of a platform drug delivery system utilizing crystal engineering and Theanine dissolution with sumatriptan is paramount, since improved drug delivery would improve the clinical status of the patient more rapidly, and would be expected to reduce many serious side effects associated with the use of sumatriptan. The present invention satisfies these and other medical needs and overcomes deficiencies found in the prior art.

The various features of novelty which characterize the invention are pointed out with particularity in the claims annexed to and forming a part of this disclosure. For a better understanding of the invention, its operation advantages and specific objects attained by its uses, reference is made to the accompanying figures and descriptive matter in which a preferred embodiment of the invention is illustrated.

SUMMARY OF THE INVENTION

It is therefore an object of the present invention to provide a method utilizing crystallization and Theanine dissolution of low solubility pharmaceuticals which is readily administrable to individuals through a variety of media.

Accordingly a platform drug delivery system and a method of improving the delivery of low solubility pharmaceuticals utilizing crystal engineering and Theanine dissolution resulting in enhanced bioactivity, dissolution rate, and solid state stability is disclosed.

It is an object of the present invention to provide a cocrystal composition composed of a quantity of a theanine enantiomer, and a quantity of a drug from a class selected from the group consisting of nucleoside analog reverse transcriptase inhibitors, non-nucleoside reverse transcriptase inhibitors, non-purine selective xanthine oxidase inhibitors, leukotriene receptor antagonists, beta-adrenergic agonists/alpha-adrenergic agonists, antihypertensive agents, loop diuretics, thiazide diuretics, atypical antipsychotic/partial dopamine agonists, non-steroidal anti-inflammatory drugs, corticosteroids, antihistamines, antineoplastic agents, antibacterial agents, antibiotics, antiviral agents, antifungal agents, antiprotozoan agents, immediate dopamine precursor agent, catechol-o-methyltransferase inhibitors, ergoline dopamine agonists, ergot derivative/dopamine $D_2$, $D_3$, $D_4$, $5-HT_{1A}$, $5-HT_{2A}$, $5-HT_{2B}$, $5-HT_{2C}$, $\alpha_{2B}$ receptor agonists, antiparkinsonian agents, direct-acting skeletal muscle relaxants, noncompetitive N-methyl D-aspartate receptor antagonists, zinc salts of gluconic acid, serotonin-1 b and serotonin-1 d receptor agonists/antimigraine agents, cytomegalovirus nucleoside analog DNA polymerase inhibitors, and guanosine analogue antiviral agents.

In certain embodiments, the antihistimines are selected from the group which includes ethanolamines and histamine $H_1$ receptor antagonists.

In further embodiments, the antineoplastic agents are selected from the group which includes protein tyrosine kinase inhibitors, antileukemic drugs, topoisomerase 1 inhibitors, and anthracycline topoisomerase inhibitors.

In yet further embodiments, the antibiotics are selected from the group which includes cephalosporins, aminopenicillins, macrolides, sulfonamides, nitroimidazole antibiotics, fluorinated bistriazole antibiotics, and cyclic lipopeptide antibiotics.

In certain embodiments, the direct-acting skeletal muscle relaxants are hydantoin derivatives.

It is also an object to provide a cocrystal composition which includes a quantity of a theanine enantiomer, and a quantity of a drug selected from the group which includes lasix, aspirin, epinephrine, zinc gluconate, dantrolene sodium, levodopa, entacapone, bromocriptine, cabergoline, nilotinib, memantine, ibuprofen, efavirenz, zidovudine, metronidazole, valganciclovir, fluconazole, ampicillin, erythromycin, sulfamethoxzole, cefdinir, cefadroxil, amoxicillin, daptomycin, acyclovir, febuxostat, hydrochlorothiazide, sumatriptan, prednisone, zinc gluconate, doxorubicin, irinotecan, aripiprazole, diflunisal, zafirlukast, and fexofenadine.

It is also an object to provide a cocrystal composition which includes a quantity of a theanine enantiomer, and a quantity of a drug for treating a condition selected from the group which includes acute pulmonary edema/congestive heart failure; acute myocardial infarction; acute ischemic stroke; acute allergic reactions, anaphylactic reactions from medications, food, latex, insect bites/stings, cardiac arrest, acute exacerbation of asthma, ventricular fibrillation, airway obstruction; Australian box jelly fish envenomations; neurologic emergencies including, malignant hyperthermia, 3,4-methylenedioxymethamphetamine intoxication, serotonin syndrome, 2,4-dinitrophenol poisoning.

In certain embodiments, the theanine enantiomer is selected from the group which includes L-theanine, D-theanine, and DL-theanine.

In yet further embodiments, the theanine enantiomer is selected from the group which includes an alpha variant of theanine and a beta variant of theanine.

In certain of these embodiments, the alpha variant of theanine is selected from the group which includes L-homotheanine, D-homotheanine, DL-homotheanine, L-bishomotheanine, D-bishomotheanine, and DL-bishomotheanine.

In certain other of these embodiments the alpha variant of theanine is a homologous analog of theanine.

In certain other of these embodiments, the alpha variant of theanine contains a functional group selected from the group which includes linear, cyclic, or branched alkyl and derivatives thereof, linear, cyclic, or branched alkenyl and derivatives thereof, and aromatic radicals and derivatives thereof.

In some of these embodiments, the aromatic radicals are aryl radicals.

In further embodiments, the theanine enantiomer is a racemic mixture of a beta variant of theanine containing a functional group selected from the group which includes linear, cyclic, or branched alkyl groups and derivatives thereof, linear, cyclic, or branched alkenyl groups and derivatives thereof, and aromatic radicals and derivatives thereof.

In certain other of these embodiments, the aromatic radicals are aryl radicals.

In certain embodiments the theanine enantiomer is an S enantiomer of a beta variant of theanine containing a functional group selected from the group which includes linear, cyclic, or branched alkyl groups and derivatives thereof, linear, cyclic, or branched alkenyl groups and derivatives thereof, and aromatic radicals and derivatives thereof.

In further embodiments, the aromatic radicals are aryl radicals.

In yet further embodiments, the theanine enantiomer is an R enantiomer of a beta variant of theanine containing a functional group selected from the group which includes linear, cyclic, or branched alkyl groups and derivatives thereof, linear, cyclic, or branched alkenyl groups and derivatives thereof, and aromatic radicals and derivatives thereof.

In certain of these embodiments, the aromatic radicals are aryl radicals.

In certain of these embodiments, the mixture further includes a sugar alcohol.

In certain of these embodiments, the sugar alcohol has a configuration selected from the group which includes the L-configuration and the D-configuration.

It is also an object to provide a cocrystal composition which includes a quantity of L-theanine, and a quantity of a chemical composition selected from the group which includes acyclovir, amoxicillin, ampicillin, aripiprazole, bromocriptine, cabergoline, cefadroxil, cefdinir, dantrolene, daptomycin, diflunisal, doxorubicin, efavirenz, entacapone, epinephrine, erythromycin, febuxostat, fexofenadine, fluconazole, furosemide, hydrochlorothiazide, R-ibuprofen, irinotecan, levodopa, memantine, metronidazole, nilotinib, prednisone, sulfamethoxazole, sumitriptan, valganciclovir, zafirlukast, zidovudine, and gluconate-zinc.

During the development of the present invention, the ability of theanine to form cocrystal products with a wide variety of drug substances has been evaluated. While theanine was not found to form cocrystals with 31 drug substances (i.e., Acetaminophen, Acetazolamide, Amiodarone, Atorvastatin, Atropine, Carbamazepine, Celecoxib, Cisplatin, CoQ-10, Cyclosporine A, Dalbavancin, Dalmaprine, Desloratadine, Famotidine, Fenofibrate, Fingolimod, (RS)-Ibuprofen, Lamivudine, Linezolid, Mannitol, Moxifloxacin, (S)-Naproxen, Ondansetron, Oxcarbazepine, Pregabalin, Ramipril, Rosuvastatin, Rufinamide, Telmisartan, Venlafaxine, and Vilazodone), surprisingly theanine was found to form cocrystals with 34 drug substances (i.e., Acyclovir, Amoxicillin, Ampicillin, Aripiprazole, Bromocriptine, Cabergoline, Cefadroxil, Cefdinir, Dantrolene, Daptomycin, Diflunisal, Doxorubicin, Efavirenz, Entacapone, Epinephrine, Erythromycin, Febuxostat, Fexofenadine, Fluconazole, Furosemide, Gluconate zinc, Hydrochlorothiazide, (R)-Ibuprofen, Irinotecan, Levodopa, Memantine, Metronidazole, Nilotinib, Prednisone, Sulfamethoxazole, Sumitriptan, Valganciclovir, Zafirlukast, and Zidovudine).

Embodiments of the present invention are directed to a cocrystal compositions including a quantity of a theanine enantiomer and drugs from the following drug classes: nucleoside analog reverse transcriptase inhibitors, nonnucleoside reverse transcriptase inhibitors, non-purine selective xanthine oxidase inhibitors, leukotriene receptor antagonists, beta-adrenergic agonists/alpha-adrenergic agonists, antihypertensive agents, loop diuretics, thiazide diuretics, atypical antipsychotic/partial dopamine agonists, nonsteroidal anti-inflammatory drugs, corticosteroids, antihistamines, antineoplastic agents, antibacterial agents, antibiotics, antiviral agents, antifungal agents, antiprotozoan agents, immediate dopamine precursor agent, catechol-o-methyltransferase inhibitors, ergoline dopamine agonists, ergot derivative/dopamine $D_2$, $D_3$, $D_4$, $5\text{-}HT_{1A}$, $5\text{-}HT_{2A}$, $5\text{-}HT_{2B}$, $5\text{-}HT_{2C}$, $\alpha_{2B}$ receptor agonists, antiparkinsonian agents, direct-acting skeletal muscle relaxants, noncompetitive N-methyl D-aspartate receptor antagonists, zinc salts of gluconic acid, serotonin-1 b and serotonin-1 d receptor agonists/antimigraine agents, cytomegalovirus nucleoside analog DNA polymerase inhibitors and guanosine analogue antiviral agents.

In addition, embodiments of the present invention are directed to compositions including a quantity of a theanine enantiomer and the following drugs lasix, aspirin, epinephrine, zinc gluconate, dantrolene sodium, levodopa, entacapone, bromocriptine, cabergoline, nilotinib, memantine, ibuprofen, efavirenz, zidovudine, metronidazole, valganciclovir, fluconazole, ampicillin, erythromycin, sulfamethoxzole, cefdinir, cefadroxil, amoxicillin, daptomycin, acyclovir, febuxostat, hydrochlorothiazide, sumatriptan, prednisone, zinc gluconate, doxorubicin, irinotecan, aripiprazole, diflunisal, zafirulkast, and fexofenadine.

Embodiments of the present invention are also directed to compositions including a quantity of a theanine enantiomer and drugs for treating the following conditions: acute pulmonary edema/congestive heart failure; acute myocardial infarction; acute ischemic stroke; acute allergic reactions, anaphylactic reactions from medications, food, latex, insect bites/stings, cardiac arrest, acute exacerbation of asthma, ventricular fibrillation, airway obstruction; Australian box jelly fish envenomations; neurologic emergencies including malignant hyperthermia, 3,4-methylenedioxymethamphetamine intoxication, serotonin syndrome, 2,4-dinitrophenol poisoning.

These and other non-limiting aspects and/or objects of the disclosure are more particularly described below. The various features of novelty which characterize the invention are pointed out with particularity in the claims annexed hereto and forming a part of the disclosure. For a better understanding of the invention, its operating advantages and specific benefits attained by its uses, reference is made to the accompanying drawings and descriptive matter in which exemplary embodiments of the invention are illustrated.

BRIEF DESCRIPTION OF THE DRAWINGS

The following is a brief description of the drawings, which are presented for the purposes of illustrating the exemplary embodiments disclosed herein and not for the purposes of limiting the same.

FIG. 9a is an x-ray powder diffraction pattern of the L-theanine/daptomycin cocrystal;

FIG. 9b is an infrared absorption spectrum of the L-theanine/daptomycin cocrystal;

DETAILED DESCRIPTION OF THE PREFERRED EMBODIMENTS

Figure 1A:
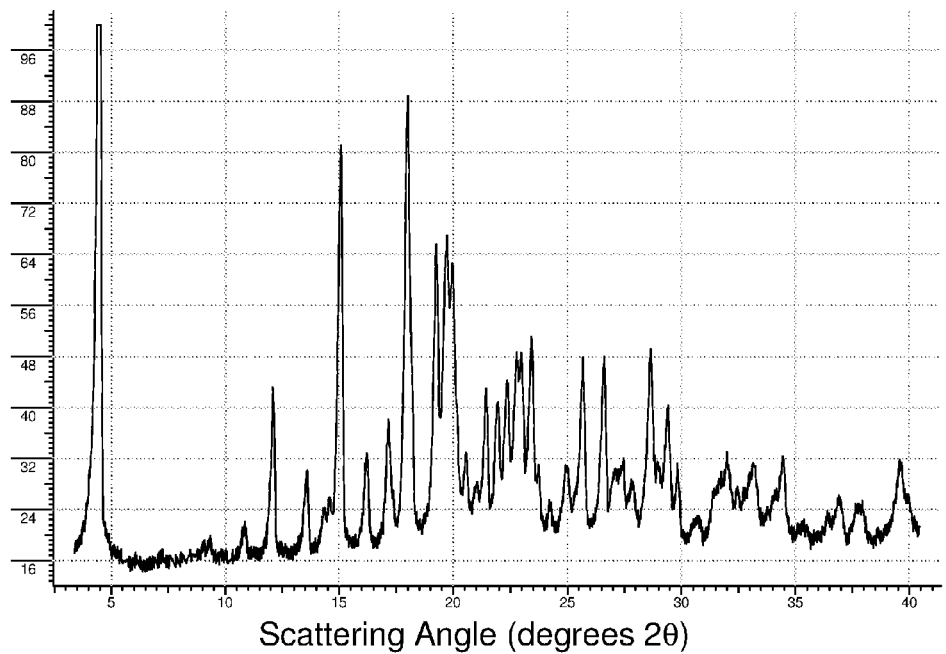
FIG. 1a is an x-ray powder diffraction pattern of the L-theanine/amoxicillin cocrystal.

Embodiments of the present invention employ Theanine (5-N-ethyl glutamine) a non-protein amino acid found naturally in green tea leaves.

Embodiments of the present invention include cocrystallization of low-solubility medication groups with Theanine (5-N-ethyl-glutamine).

Embodiments of the present invention include cocrystallization of the following medication groups with theanine (5-N-ethyl-glutamine): nucleoside analog reverse transcriptase inhibitors, non-nucleoside reverse transcriptase inhibitors, non-purine selective xanthine oxidase inhibitors, leukotriene receptor antagonists, beta-adrenergic agonists/alpha-adrenergic agonists, antihypertensive agents, loop diuretics, thiazide diuretics, atypical antipsychotic/partial dopamine agonists, non-steroidal anti-inflammatory drugs, corticosteroids, antihistamines (ethanolamines, histamine H1 receptor antagonists), antineoplastic agents (protein tyrosine kinase inhibitors/antileukemic drugs, topoisomerase 1 inhibitors, anthracycline topoisomerase inhibitors), antibacterial agents/antibiotics (cephalosporins, aminopenicillins, macrolides, sulfonamides, nitroimidazole antibiotics, fluorinated bistriazole antibiotics, cyclic lipopeptide antibiotics), antiviral agents, antifungal agents, antiprotozoan agents, immediate dopamine precursor agent, catechol-o-methyltransferase inhibitors, ergoline dopamine agonists, ergot derivative/dopamine $D_2$, $D_3$, $D_4$, 5-$HT_{1A}$, 5-$HT_{2A}$, 5-$HT_{2B}$, 5-$HT_{2C}$, $\alpha_{2B}$ receptor agonists, antiparkinsonian agents, direct-acting skeletal muscle relaxants (hydantoin derivatives), noncompetitive NMDA (N-methyl D-aspartate receptor) antagonists, zinc salts of gluconic acid, serotonin-1 b and serotonin-1d receptor agonists/antimigraine agents, cytomegalovirus nucleoside analog DNA polymerase inhibitors and guanosine analogue antiviral agents.

The present invention is directed to, among other things, crystallization and theanine dissolution of medications from the following drug classes: nucleoside analog reverse transcriptase inhibitors, non-nucleoside reverse transcriptase inhibitors, non-purine selective xanthine oxidase inhibitors, leukotriene receptor antagonists, beta-adrenergic agonists/alpha-adrenergic agonists, antihypertensive agents, loop diuretics, thiazide diuretics, atypical antipsychotic/partial dopamine agonists, non-steroidal anti-inflammatory drugs, corticosteroids, antihistamines (ethanolamines, histamine H1 receptor antagonists), antineoplastic agents (protein tyrosine kinase inhibitors/antileukemic drugs, topoisomerase 1 inhibitors, anthracycline topoisomerase inhibitors), antibacterial agents/antibiotics (cephalosporins, aminopenicillins, macrolides, sulfonamides, nitroimidazole antibiotics, fluorinated bistriazole antibiotics, cyclic lipopeptide antibiotics), antiviral agents, antifungal agents, antiprotozoan agents, immediate dopamine precursor agent, catechol-o-methyltransferase inhibitors, ergoline dopamine agonists, ergot derivative/dopamine $D_2$, $D_3$, $D_4$, $5\text{-}HT_{1A}$, $5\text{-}HT_{2A}$, $5\text{-}HT_{2B}$, $5\text{-}HT_{2C}$, $\alpha_{2B}$ receptor agonists, antiparkinsonian agents, direct-acting skeletal muscle relaxants (hydantoin derivatives), noncompetitive NMDA (N-methyl D-aspartate receptor) antagonists, zinc salts of gluconic acid, serotonin-1b and serotonin-1d receptor agonists/antimigraine agents, cytomegalovirus nucleoside analog DNA polymerase inhibitors and guanosine analogue antiviral agents.

Further, the Theanine contained in compositions according to embodiments of the present invention may be of any of L-form, D-form, DL-form.

According to embodiments of the present invention the L-, D-, DL-alpha amino acids of Theanine and their sidechain carbon homologues (nor, homo, and bishomologues) may have a functional R-group, where R1 may contain linear, cyclic, or branched alkyl groups and derivatives thereof; linear, cyclic, or branched alkenyl groups and derivatives thereof; and aromatic radicals and derivatives thereof. In embodiments of the present invention, the aromatic radicals may be aryl radicals.

According to the embodiments of the present invention in addition to L-Theanine, other analogues include D-Theanine, racemic Theanine or D, L-Theanine and its congeners including beta and reverse beta amino acid forms, shortened or nor-Theanine (aspartic acid analogue), and the lengthened homo-Theanines and their isomers. Further, gamma alkylamido analogues extend a full range of molecular property for drug cocrystals.

According to the embodiments of the present invention the single enantiomers (S and R) and racemic forms (S, R-mixture) of the beta amino acids of Theanine may have a functional R-group, where R1 may contain linear, cyclic, or branched alkyl groups and derivatives thereof; linear, cyclic, or branched alkenyl groups and derivatives thereof; and aromatic radicals and derivatives thereof. In embodiments of the present invention, the aromatic radicals may be aryl radicals.

Embodiments of the present invention may include cocrystal compositions of drugs from the classes listed below and the enantiomers, L- and D-isomers, D, L-racemic mixture, S- and R-isomers, S, R-racemic mixtures, all rotamers, tautomers, salt forms, and hydrates of the alpha and beta amino acids of Theanine in which the N-substituted functional R1-group [C4 or gamma-CH2-C(O)—NR1] may contain linear, cyclic, or branched alkyl groups and derivatives thereof; linear, cyclic or branched alkenyl groups and derivatives thereof; and aromatic radicals (which may be aryl radicals) and derivatives thereof making up all the analogue forms of Theanine: nucleoside analog reverse transcriptase inhibitors, non-nucleoside reverse transcriptase inhibitors, non-purine selective xanthine oxidase inhibitors, leukotriene receptor antagonists, beta-adrenergic agonists/ alpha-adrenergic agonists, antihypertensive agents, loop diuretics, thiazide diuretics, atypical antipsychotic/partial dopamine agonists, non-steroidal anti-inflammatory drugs, corticosteroids, antihistamines (ethanolamines, histamine H1 receptor antagonists), antineoplastic agents (protein tyrosine kinase inhibitors/antileukemic drugs, topoisomerase 1 inhibitors, anthracycline topoisomerase inhibitors), antibacterial agents/antibiotics (cephalosporins, aminopenicillins, macrolides, sulfonamides, nitroimidazole antibiotics, fluorinated bistriazole antibiotics, cyclic lipopeptide antibiotics), antiviral agents, antifungal agents, antiprotozoan agents, immediate dopamine precursor agent, catechol-o-methyltransferase inhibitors, ergoline dopamine agonists, ergot derivative/dopamine $D_2$, $D_3$, $D_4$, $5\text{-}HT_{1A}$, $5\text{-}HT_{2A}$, $5\text{-}HT_{2B}$, $5\text{-}HT_{2C}$, $\alpha_{2B}$ receptor agonists, antiparkinsonian agents, direct-acting skeletal muscle relaxants (hydantoin derivatives), noncompetitive NMDA (N-methyl D-aspartate receptor) antagonists, zinc salts of gluconic acid, serotonin-1b and serotonin-1d receptor agonists/antimigraine agents, cytomegalovirus nucleoside analog DNA polymerase inhibitors and guanosine analogue antiviral agents.

Embodiments of the present invention include cocrystal compositions with Theanine dissolution of sumtriptan in combination with an NSAID.

Embodiments of the present invention include cocrystal compositions with Theanine dissolution of Levodopa in combination with Entacapone.

Embodiments of the present invention include cocrystal compositions with theanine dissolution of zinc gluconate in combination with (R)-Ibuprofen.

Derivatives prepared using compositions according to embodiments of the present invention can be administered via intravenous, intramuscular, intradermal, transdermal, subcutaneous, intraperitoneal, intraventricular, intrathecal, intraarticular, sublingual, subconjunctival, and intravitreal routes, or in the form of eye drops, orally, topically, transmucosal, rectally, via nasal spray, inhalation, nanoparticle delivery systems, protein and peptide drug delivery systems, beaded delivery systems, mucosal vaccine delivery, colloidal drug carrier systems, controlled-released technology, liposomal and targeted drug delivery systems, iontophoretic devices to administer drugs through skin, programmable implanted drug-delivery devices, molecular targeting with immunoliposomes and other ligand-directed constructs, drug carriers featuring direct molecular targeting of cancer cells via antibody-mediated or other ligand-medicated interactions (Tiwari, G., "Drug Delivery Systems: An updated review." *Int J Pharm Ivestig*. 2012 January-March; 2(1): 2-11).

The pharmaceutical compositions according to embodiments of the present invention may be prepared as oral solids (tablets, oral disintegrating tablets, effervescent tablets, capsules), oral liquids, hard or soft gelatin capsules, microgels, microspheres, microcapsules, quick dissolve, controlled released, modified released, extended release, slow release, sustained release, syrups, suspensions, granules, wafer (films), pellets, lozenges, powders, chewable, suppositories, ointments, solutions, parenteral/injectable powders or granules that are pre-mixed or reconstituted, lotions, gels, creams, foams, propellants, strips, liposomes, proliposomes, prodrugs, cyclodextrins, m16 nasal and buccal aerosol sprays, encapsulated cells, oral soft gels, micellar solutions, vesicle and liquid crystal dispersions and nanoparticle dispersions (coated nanoparticles, pegylated nanoparticles, solid lipid particles, nanogels), and nanoemulsions (Tiwari, G., "Drug Delivery Systems: An updated review." *Int J Pharm Ivestig*. 2012 January-March; 2(1): 2-11).

Cocrystals according to embodiments of the present invention may be used to improve one or more physical properties, such as solubility, stability, and dissolution rate, of the active pharmaceutical ingredient of a selected treatment or prevention.

Next, the present invention will be described in further detail by means of examples, without intending to limit the scope of the present invention to these examples alone. The following are exemplary formulations with cocrystal compositions and Theanine dissolution from the following medication groups in accordance with the present invention: nucleoside analog reverse transcriptase inhibitors, non-nucleoside reverse transcriptase inhibitors, non-purine selective xanthine oxidase inhibitors, leukotriene receptor antagonists, beta-adrenergic agonists/alpha-adrenergic agonists, antihypertensive agents, loop diuretics, thiazide diuretics, atypical antipsychotic/partial dopamine agonists, nonsteroidal anti-inflammatory drugs, corticosteroids, antihistamines (ethanolamines, histamine H1 receptor antagonists), antineoplastic agents (protein tyrosine kinase inhibitors/antileukemic drugs, topoisomerase 1 inhibitors, anthracycline topoisomerase inhibitors), antibacterial agents/antibiotics (cephalosporins, aminopenicillins, macrolides, sulfonamides, nitroimidazole antibiotics, fluorinated bistriazole antibiotics, cyclic lipopeptide antibiotics), antiviral agents, antifungal agents, antiprotozoan agents, immediate dopamine precursor agent, catechol-o-methyltransferase inhibitors, ergoline dopamine agonists, ergot derivative/dopamine $D_2$, $D_3$, $D_4$, $5-HT_{1A}$, $5-HT_{2A}$, $5-HT_{2B}$, $5-HT_{2C}$, $\alpha_{2B}$ receptor agonists, antiparkinsonian agents, direct-acting skeletal muscle relaxants (hydantoin derivatives), noncompetitive NMDA (N-methyl D-aspartate receptor) antagonists, zinc salts of gluconic acid, serotonin-1b and serotonin-1 d receptor agonists/antimigraine agents, cytomegalovirus nucleoside analog DNA polymerase inhibitors and guanosine analogue antiviral agents.

Experimental Details

X-ray powder diffraction (XRPD) patterns were obtained using a Rigaku MiniFlex powder diffraction system, equipped with a horizontal goniometer operating in the θ/2θ mode. The X-ray source was nickel-filtered Kα emission of copper (1.54184 Å). Samples were packed into the sample holder using a back-fill procedure, and were scanned over the range of 3.5 to 40 degrees 2θ at a scan rate of 0.5 degrees 2θ/min. Using a data acquisition rate of 1 point per second, these scanning parameters equate to a step size of 0.0084 degrees 2θ. Calibration of the diffractometer system was effected using purified talc as a reference material. The intensity scale for all diffraction patterns was normalized so that the relative intensity of the most intense peak in the pattern equaled 100%.

Measurements of differential scanning calorimetry (DSC) were obtained on a TA Instruments 2910 thermal analysis system. Samples of approximately 1-2 mg were accurately weighed into an aluminum DSC pan, and then covered with an aluminum lid that was inverted and pressed down so as to tightly contain the powder between the top and bottom aluminum faces of the lid and pan. The samples were then heated over the temperature range of 20-250° C., at a heating rate of 10° C./min.

Fourier-transform infrared absorption (FTIR) spectra were obtained at a resolution of 4 $cm^{-1}$ using a Shimadzu model 8400S spectrometer, with each spectrum being obtained as the average of 40 individual spectra. The data were acquired using the attenuated total reflectance (ATR) sampling mode, where the samples were clamped against the ZnSe/diamond crystal of a Pike MIRacle™ single reflection horizontal ATR sampling accessory. The intensity scale for all spectra was normalized so that the relative intensity of the most intense peak in the spectrum 100%.

Example 1

Figure 1B:
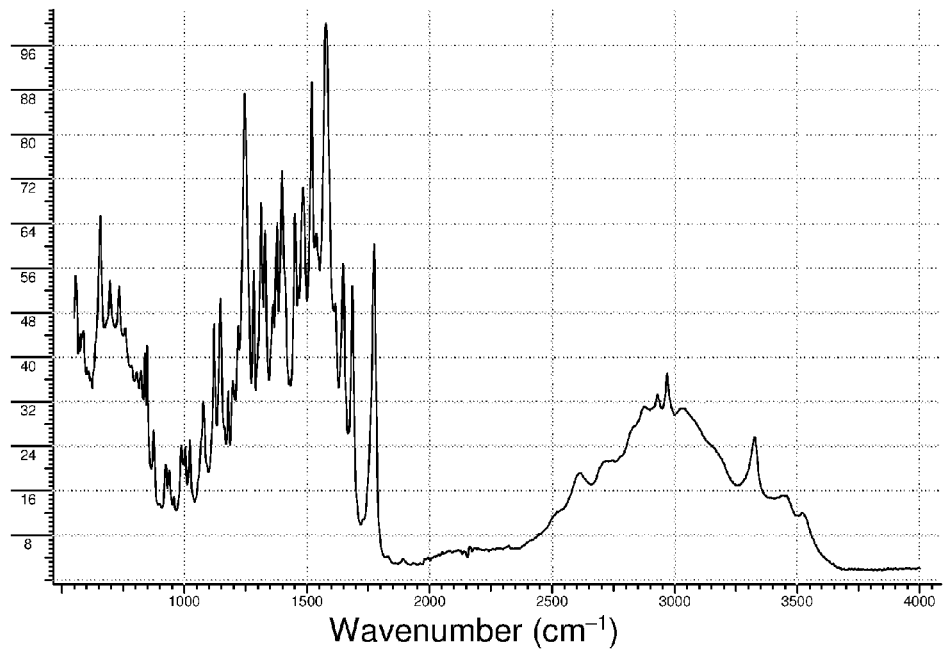
FIG. 1b is an infrared absorption spectrum of the L-theanine/amoxicillin cocrystal.

0.327 g of amoxicillin trihydrate (0.780 mmol) and 0.136 g of L-theanine (0.781 mmol) were weighed directly into the bowl of an agate mortar, and wetted with 70% isopropanol to form a moderately thick slurry. The slurry was thoroughly ground at the time of mixing, and then periodically reground until the contents were dry. The XRPD pattern of the product is shown in FIG. 1a, while the FTIR spectrum is shown in FIG. 1b. The DSC melting endotherm of the product was characterized by a peak maximum at 208° C.

Example 2

Figure 2A:
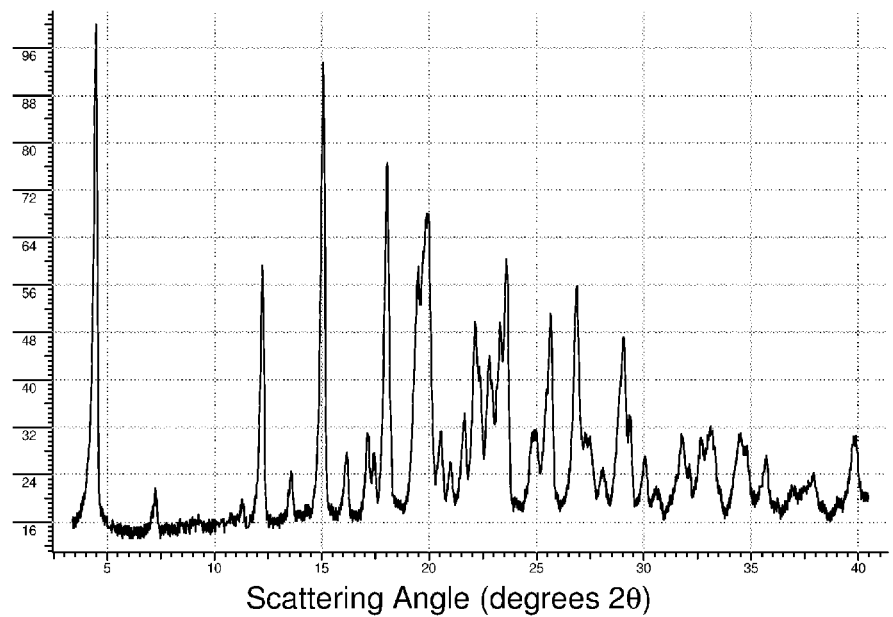
FIG. 2a is an x-ray powder diffraction pattern of the L-theanine/ampicillin cocrystal.
Figure 2B:
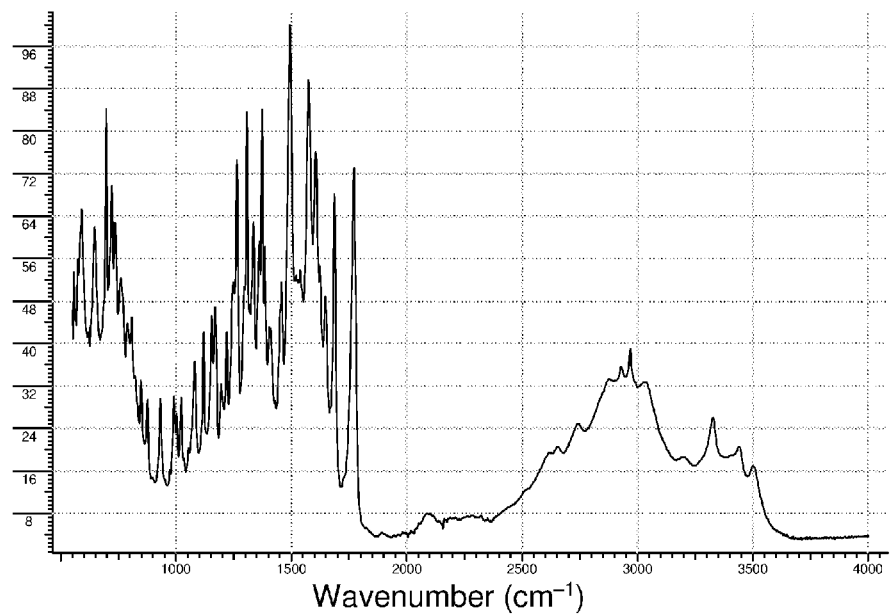
FIG. 2b is an infrared absorption spectrum of the L-theanine/ampicillin cocrystal.

0.311 g of ampicillin trihydrate (0.771 mmol) and 0.141 g of L-theanine (0.809 mmol) were weighed directly into the bowl of an agate mortar, and wetted with 70% isopropanol to form a moderately thick slurry. The slurry was thoroughly ground at the time of mixing, and then periodically reground until the contents were dry. The XRPD pattern of the product is shown in FIG. 2a, while the FTIR spectrum is shown in FIG. 2b. The DSC melting endotherm of the product was characterized by a peak maximum at 212° C.

Example 3

Figure 3A:
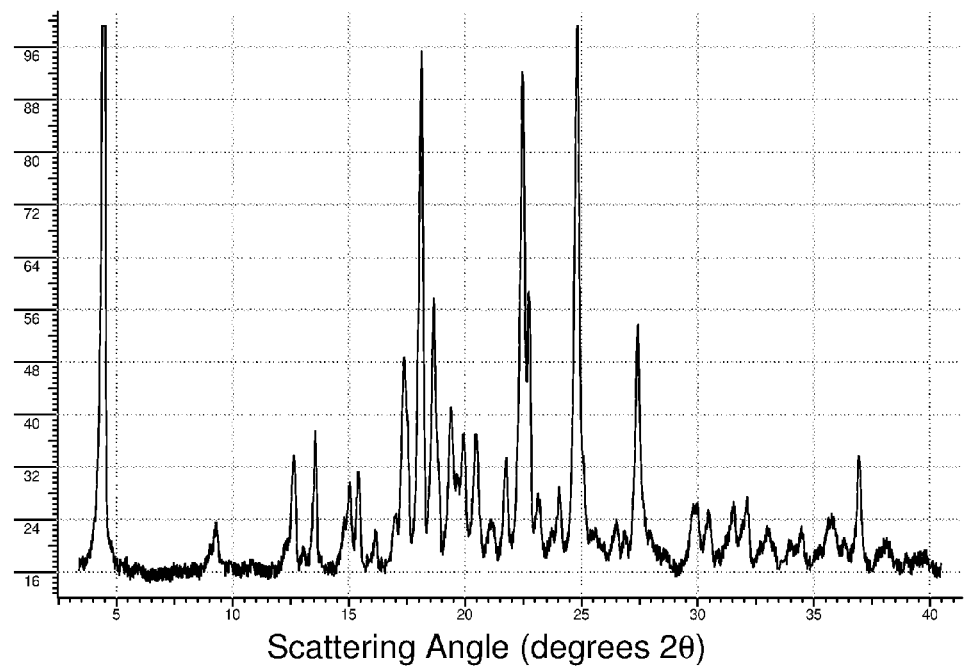
FIG. 3a is an x-ray powder diffraction pattern of the L-theanine/aripiprazole cocrystal.
Figure 3B:
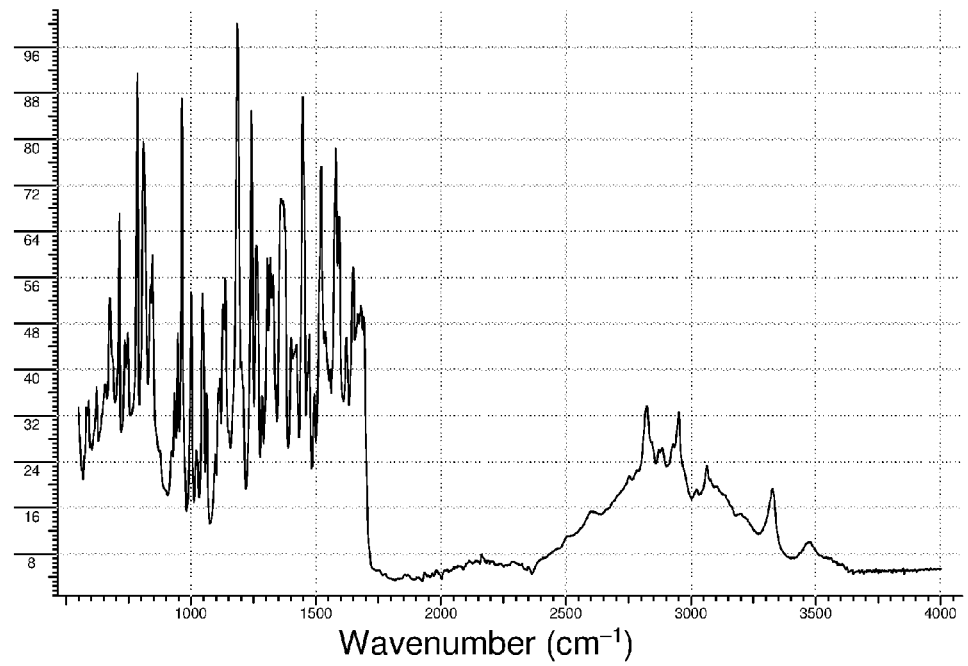
FIG. 3b is an infrared absorption spectrum of the L-theanine/aripiprazole cocrystal.

0.315 g of aripiprazole (0.703 mmol) and 0.129 g of L-theanine (0.741 mmol) were weighed directly into the bowl of an agate mortar, and wetted with 70% isopropanol to form a moderately thick slurry. The slurry was thoroughly ground at the time of mixing, and then periodically reground until the contents were dry. The XRPD pattern of the product is shown in FIG. 3a, while the FTIR spectrum is shown in FIG. 3b. The DSC melting endotherm of the product was characterized by a peak maximum at 148° C.

Example 4

Figure 4A:
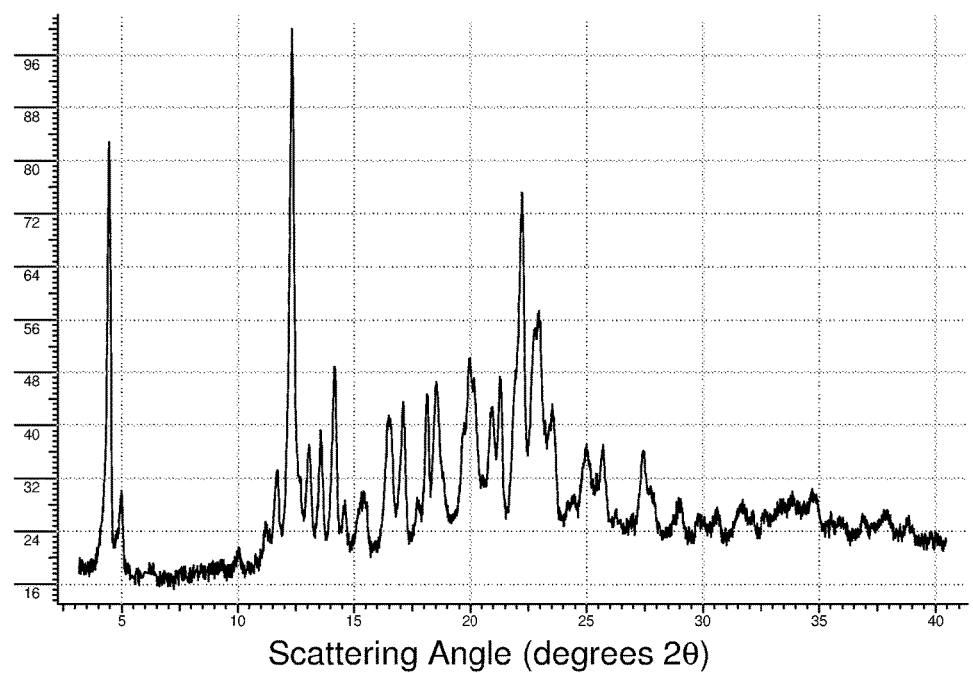
FIG. 4a is an x-ray powder diffraction pattern of the L-theanine/bromocriptine cocrystal.
Figure 4B:
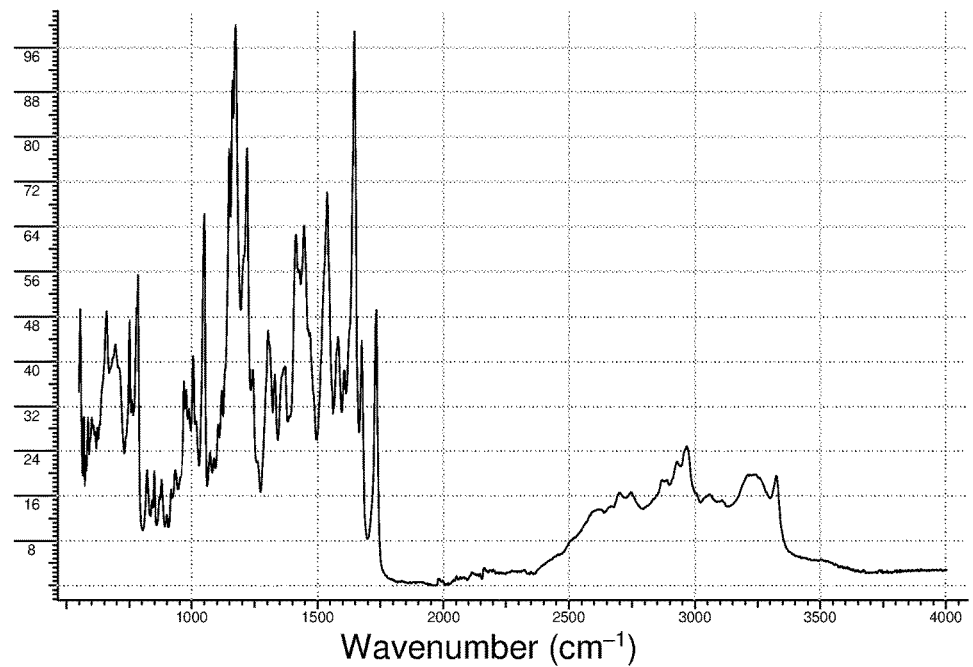
FIG. 4b is an infrared absorption spectrum of the L-theanine/bromocriptine cocrystal.

0.165 g of bromocriptine (0.252 mmol) and 0.046 g of L-theanine (0.264 mmol) were weighed directly into the bowl of an agate mortar, and wetted with 70% isopropanol to form a moderately thick slurry. The slurry was thoroughly ground at the time of mixing, and then periodically reground until the contents were dry. The XRPD pattern of the product is shown in FIG. 4a, while the FTIR spectrum is shown in FIG. 4b. The DSC melting endotherm of the product was characterized by a peak maximum at 197° C.

Example 5

Figure 5A:
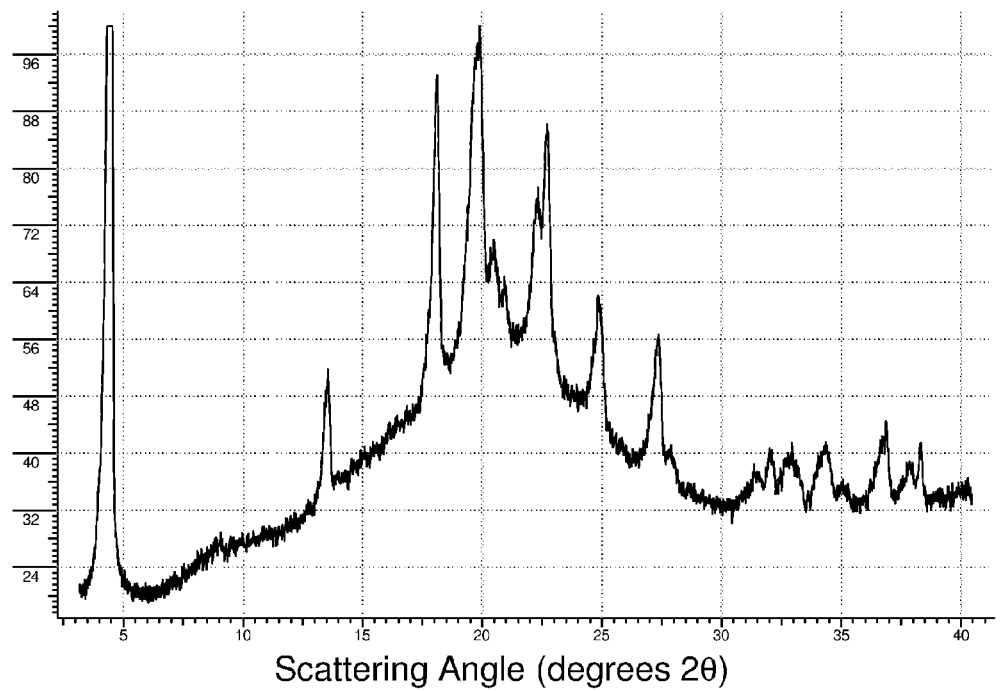
FIG. 5a is an x-ray powder diffraction pattern of the L-theanine/cabergoline cocrystal.
Figure 5B:
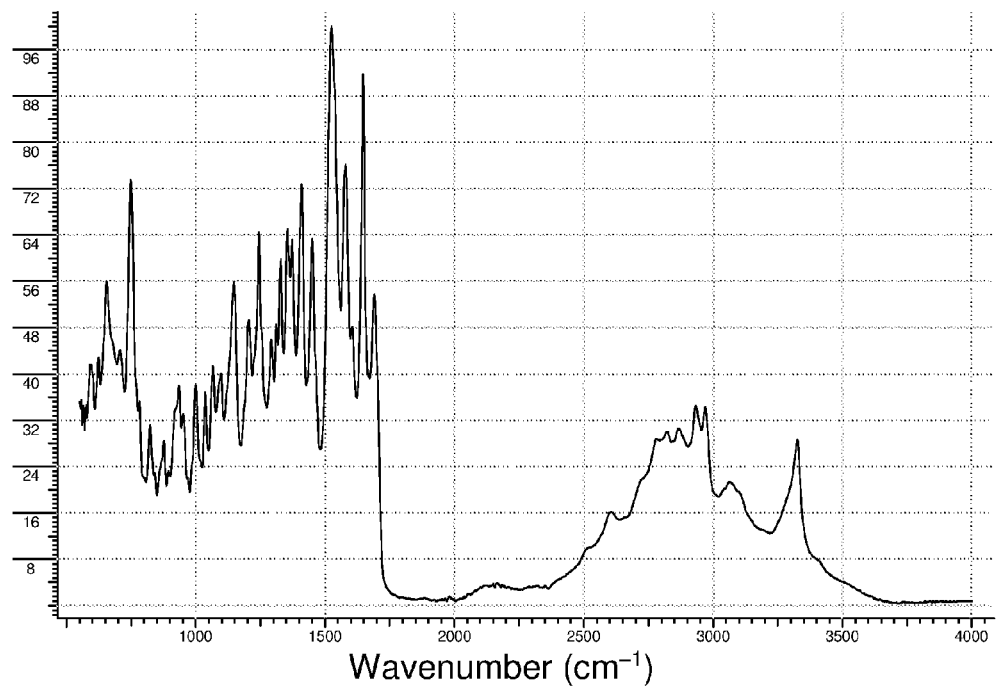
FIG. 5b is an infrared absorption spectrum of the L-theanine/cabergoline cocrystal.

0.218 g of cabergoline (0.483 mmol) and 0.088 g of L-theanine (0.505 mmol) were weighed directly into the bowl of an agate mortar, and wetted with 70% isopropanol to form a moderately thick slurry. The slurry was thoroughly ground at the time of mixing, and then periodically reground until the contents were dry. The XRPD pattern of the product is shown in FIG. 5a, while the FTIR spectrum is shown in FIG. 5b. The DSC melting endotherm of the product was characterized by a peak maximum at 52° C.

Example 6

Figure 6A:
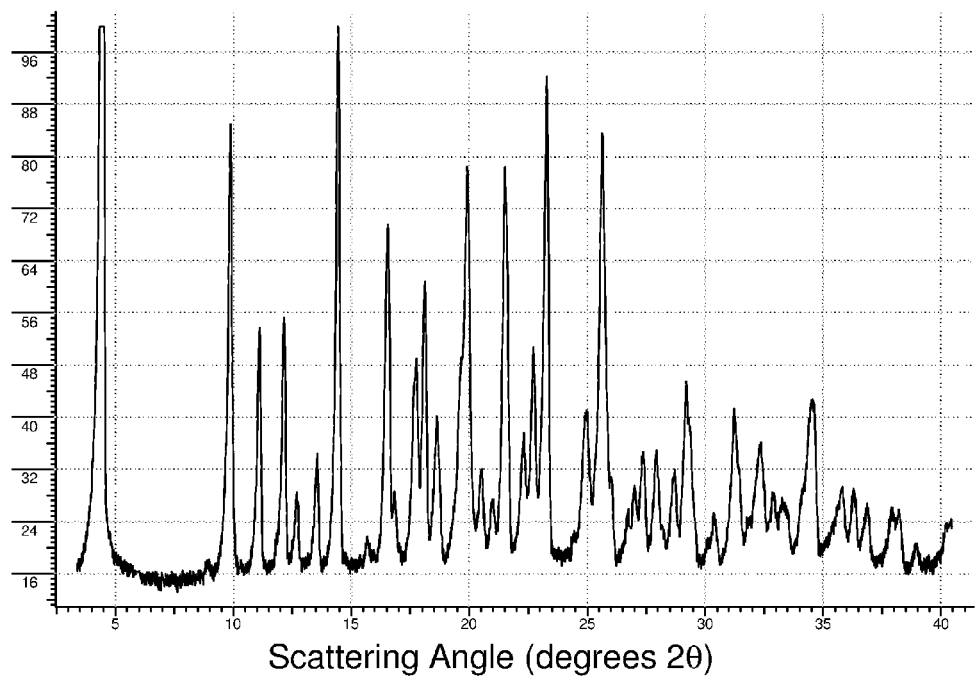
FIG. 6a is an x-ray powder diffraction pattern of the L-theanine/cefadroxil cocrystal.
Figure 6B:
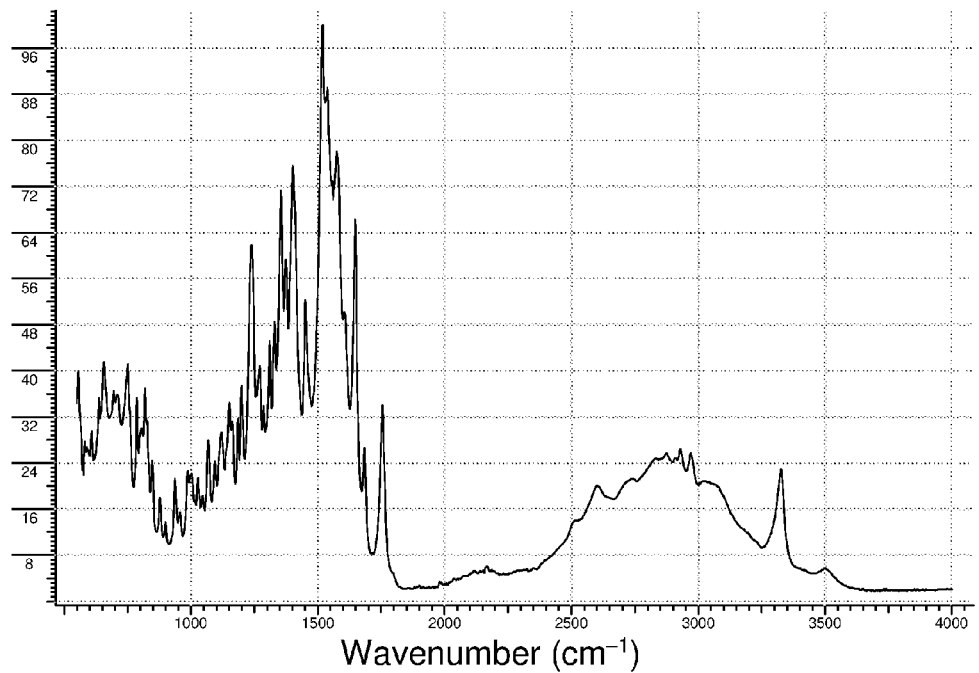
FIG. 6b is an infrared absorption spectrum of the L-theanine/cefadroxil cocrystal.

0.314 of cefadroxil monohydrate (0.849 mmol) and 0.151 g of L-theanine (0.867 mmol) were weighed directly into the bowl of an agate mortar, and wetted with 70% isopropanol to form a moderately thick slurry. The slurry was thoroughly ground at the time of mixing, and then periodically reground until the contents were dry. The XRPD pattern of the product is shown in FIG. 6a, while the FTIR spectrum is shown in FIG. 6b. The DSC melting endotherm of the product was characterized by a peak maximum at 213° C.

Example 7

Figure 7A:
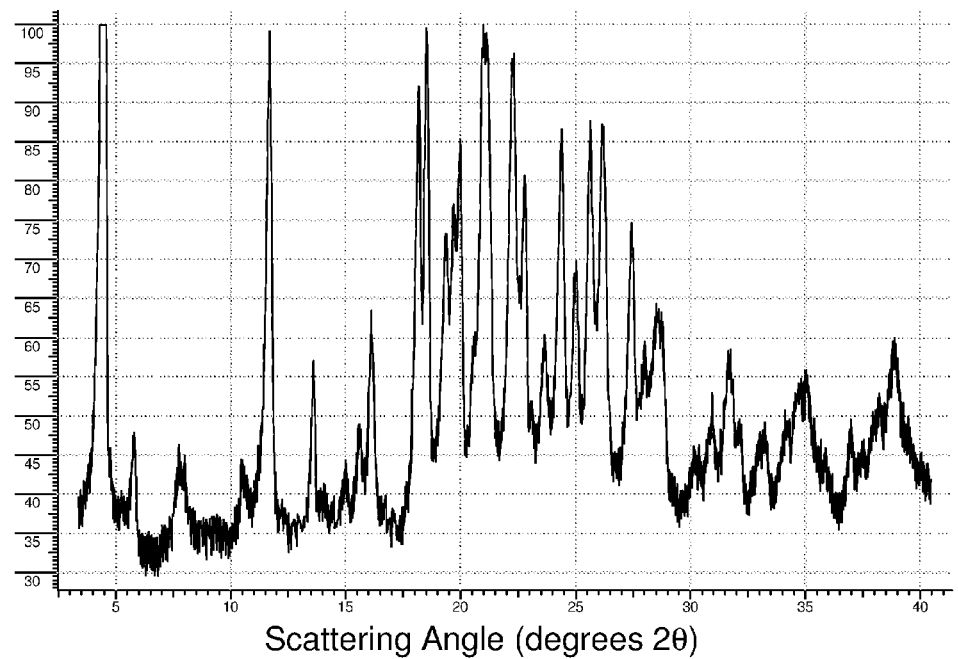
FIG. 7a is an x-ray powder diffraction pattern of the L-theanine/cefdinir cocrystal.
Figure 7B:
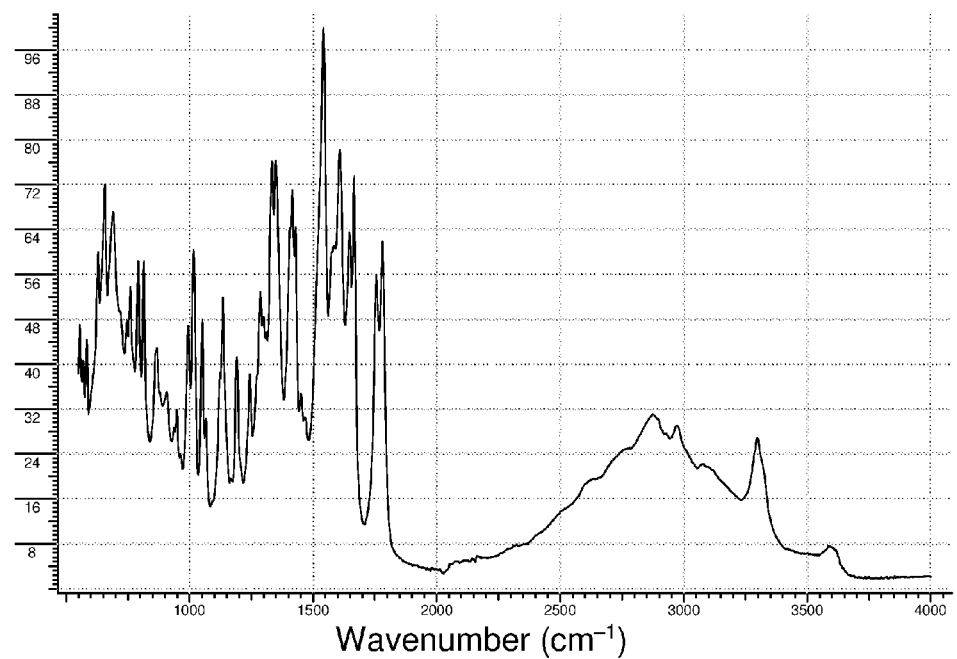
FIG. 7b is an infrared absorption spectrum of the L-theanine/cefdinir cocrystal.

0.335 of cefdinir monohydrate (0.810 mmol) and 0.140 g of L-theanine (0.804 mmol) were weighed directly into the bowl of an agate mortar, and wetted with 70% isopropanol to form a moderately thick slurry. The slurry was thoroughly ground at the time of mixing, and then periodically re-ground until the contents were dry. The XRPD pattern of the product is shown in FIG. 7a, while the FTIR spectrum is shown in FIG. 7b. The DSC melting endotherm of the product was characterized by a peak maximum at 157° C.

Example 8

Figure 8A:
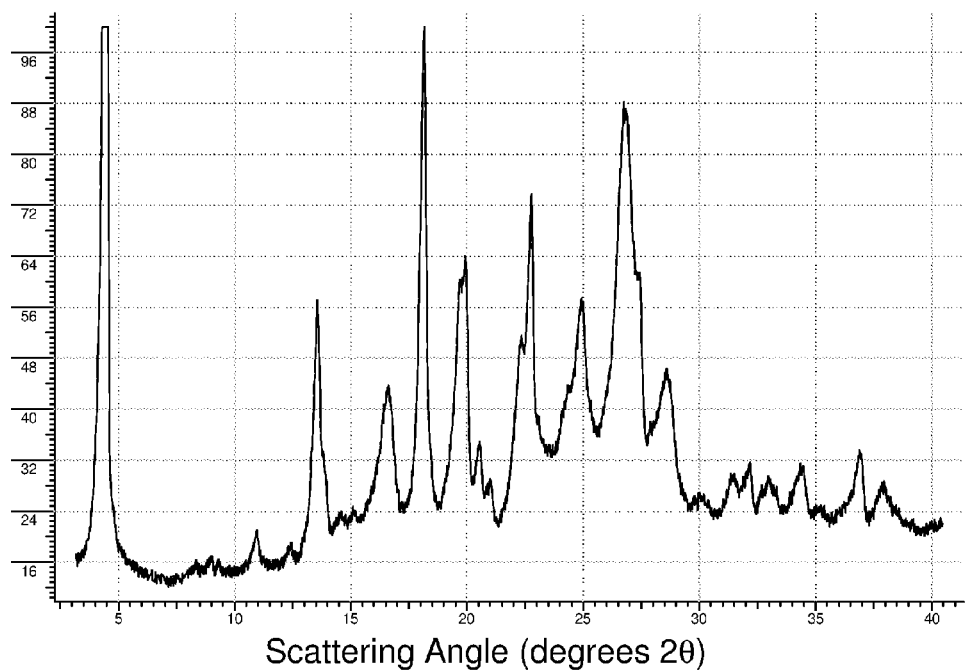
FIG. 8a is an x-ray powder diffraction pattern of the L-theanine/dantrolene cocrystal.
Figure 8B:
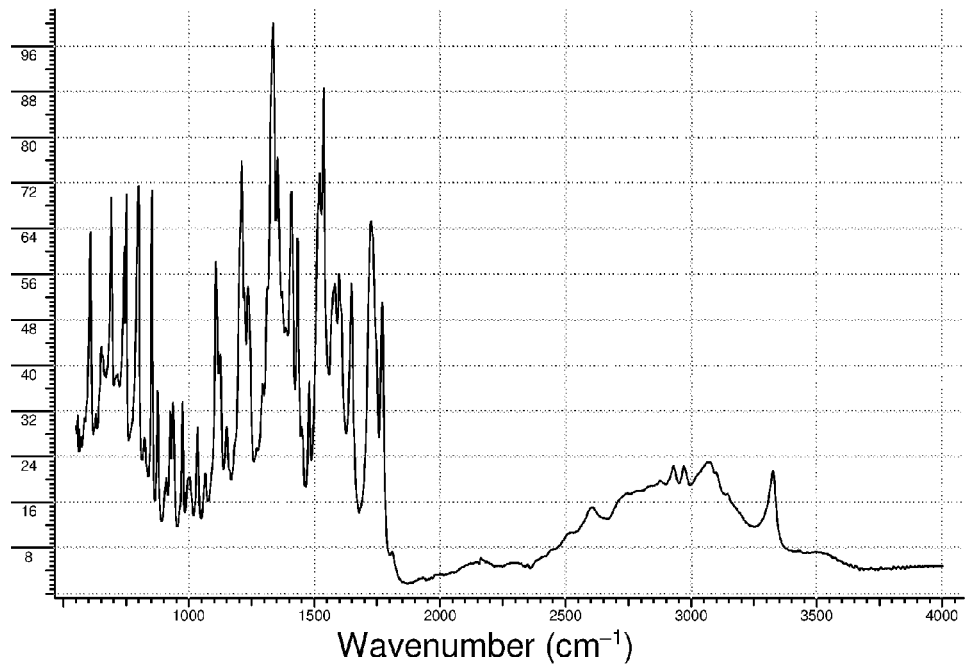
FIG. 8b is an infrared absorption spectrum of the L-theanine/dantrolene cocrystal.

0.208 g of cabergoline (0.662 mmol) and 0.115 g of L-theanine (0.660 mmol) were weighed directly into the bowl of an agate mortar, and wetted with 70% isopropanol to form a moderately thick slurry. The slurry was thoroughly ground at the time of mixing, and then periodically re-ground until the contents were dry. The XRPD pattern of the product is shown in FIG. 8a, while the FTIR spectrum is shown in FIG. 8b. The DSC melting endotherm of the product was characterized by a peak maximum at 209° C.

Example 9

0.256 g of daptomycin (0.158 mmol) and 0.030 g of L-theanine (0.172 mmol) were weighed directly into the bowl of an agate mortar, and wetted with 70% isopropanol to form a moderately thick slurry. The slurry was thoroughly ground at the time of mixing, and then periodically re-ground until the contents were dry. The XRPD pattern of the product is shown in FIG. 9a, while the FTIR spectrum is shown in FIG. 9b. The DSC melting endotherm of the product was characterized by a peak maximum at 213° C.

Example 10

Figure 10A:
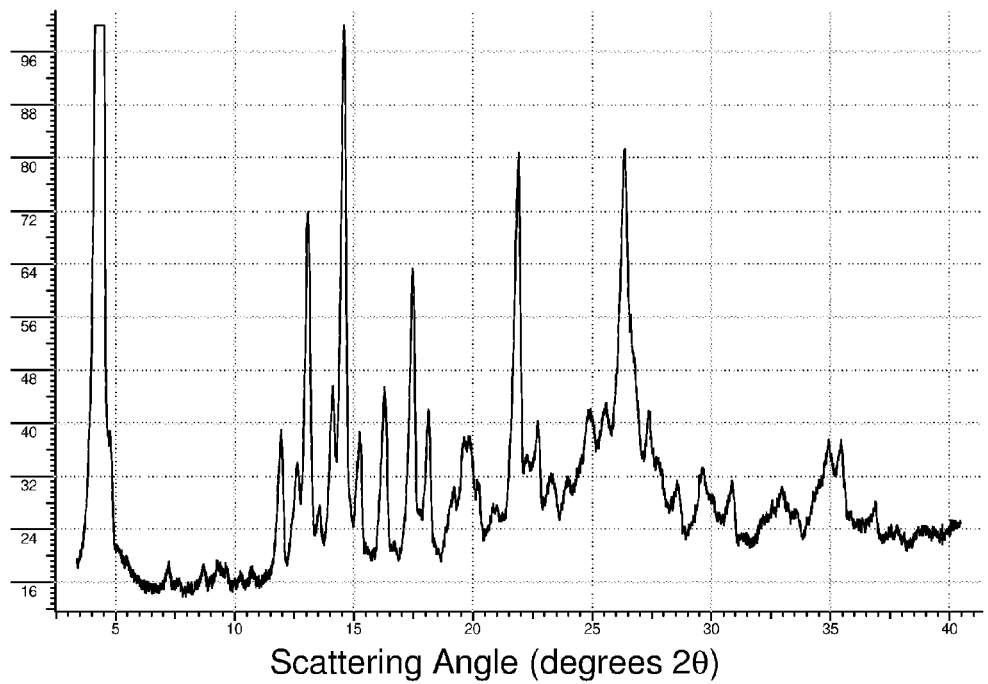
FIG. 10a is an x-ray powder diffraction pattern of the L-theanine/diflunisal cocrystal.
Figure 10B:
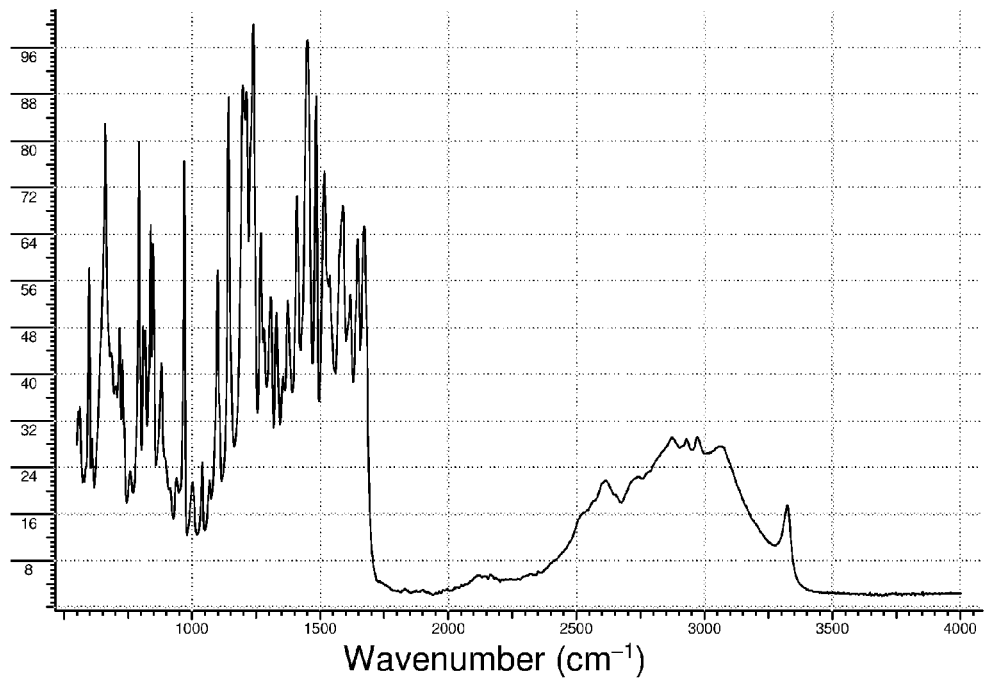
FIG. 10b is an infrared absorption spectrum of the L-theanine/diflunisal cocrystal.

0.373 g of diflunisal (1.491 mmol) and 0.269 g of L-theanine (1.544 mmol) were weighed directly into the bowl of an agate mortar, and wetted with 70% isopropanol to form a moderately thick slurry. The slurry was thoroughly ground at the time of mixing, and then periodically re-ground until the contents were dry. The XRPD pattern of the product is shown in FIG. 10a, while the FTIR spectrum is shown in FIG. 10b. The DSC melting endotherm of the product was characterized by a peak maximum at 172° C.

Example 11

Figure 11A:
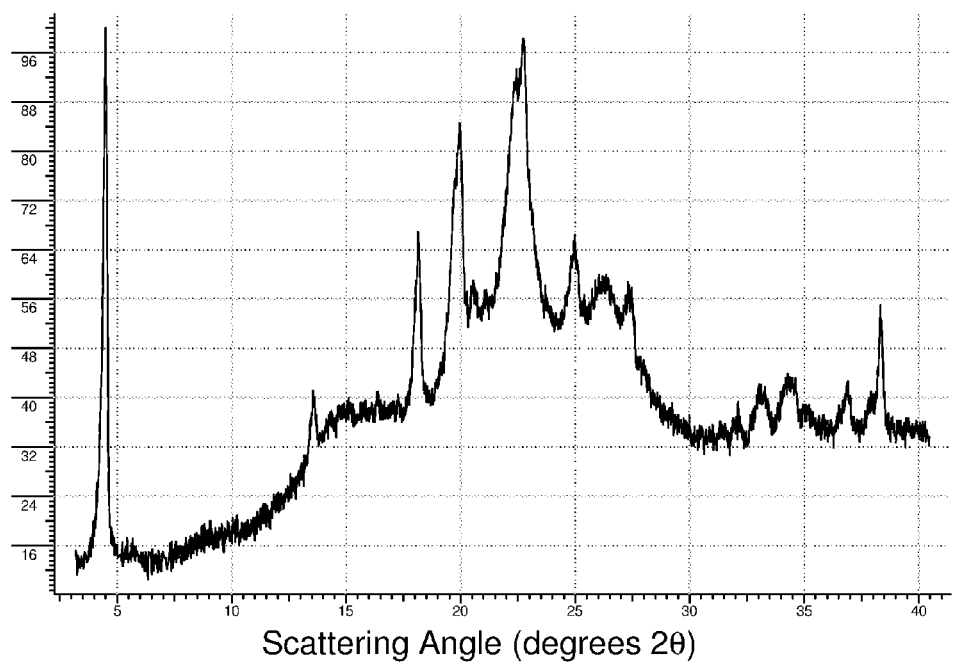
FIG. 11a is an x-ray powder diffraction pattern of the L-theanine/doxorubicin cocrystal.
Figure 11B:
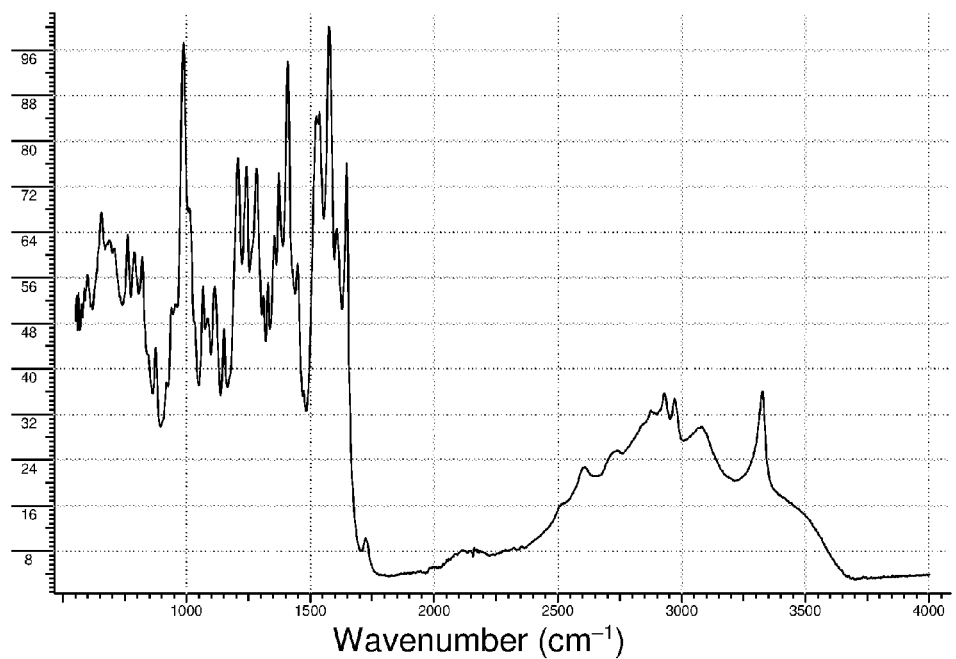
FIG. 11b is an infrared absorption spectrum of the L-theanine/doxorubicin cocrystal.

0.077 g of doxorubicin (0.142 mmol) and 0.027 g of L-theanine (0.155 mmol) were weighed directly into the bowl of an agate mortar, and wetted with 70% isopropanol to form a moderately thick slurry. The slurry was thoroughly ground at the time of mixing, and then periodically re-ground until the contents were dry. The XRPD pattern of the product is shown in FIG. 11a, while the FTIR spectrum is shown in FIG. 11b. The DSC melting endotherm of the product was characterized by a peak maximum at 209° C.

Example 12

Figure 12A:
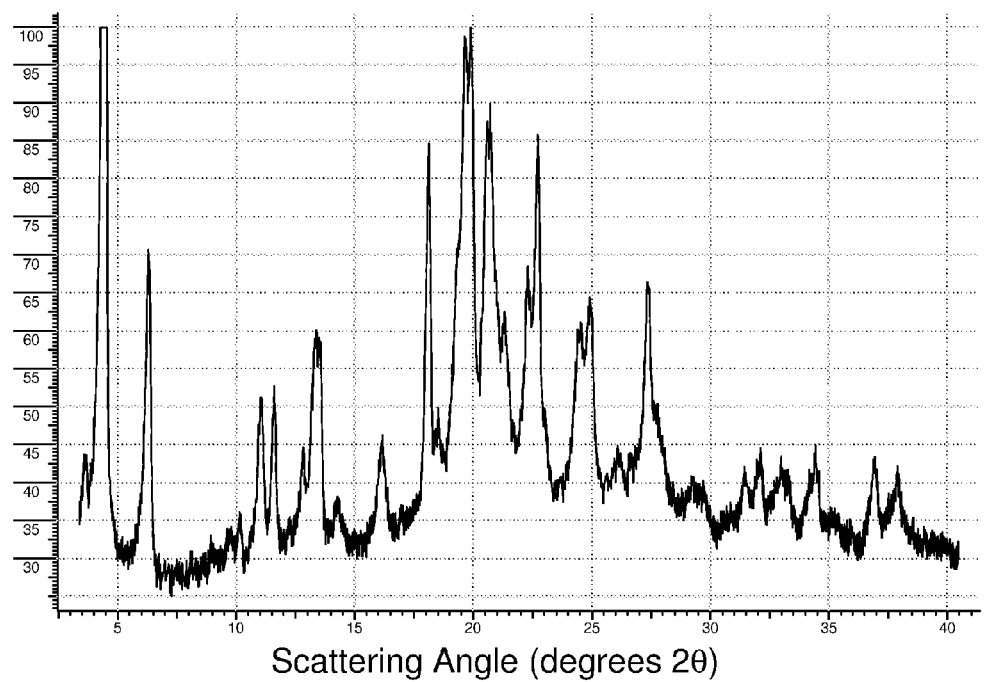
FIG. 12a is an x-ray powder diffraction pattern of the L-theanine/efavirenz cocrystal.
Figure 12B:
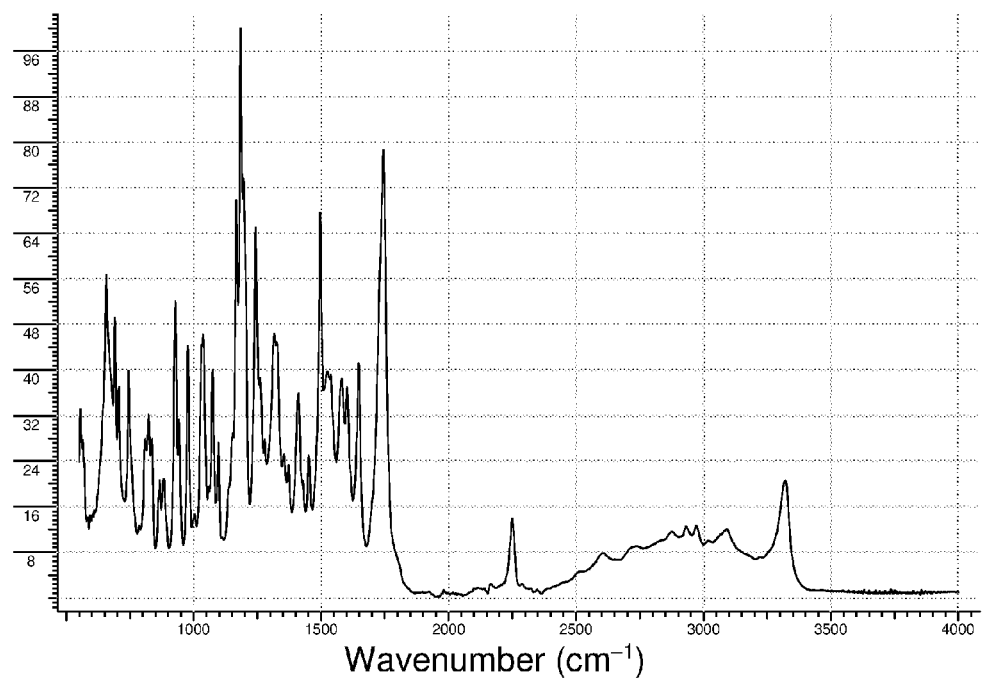
FIG. 12b is an infrared absorption spectrum of the L-theanine/efavirenz cocrystal.

0.315 g of efavirenz (0.998 mmol) and 0.177 g of L-theanine (1.016 mmol) were weighed directly into the bowl of an agate mortar, and wetted with 70% isopropanol to form a moderately thick slurry. The slurry was thoroughly ground at the time of mixing, and then periodically re-ground until the contents were dry. The XRPD pattern of the product is shown in FIG. 12a, while the FTIR spectrum is shown in FIG. 12b. The DSC melting endotherm of the product was characterized by a peak maximum at 136° C.

Example 13

Figure 13A:
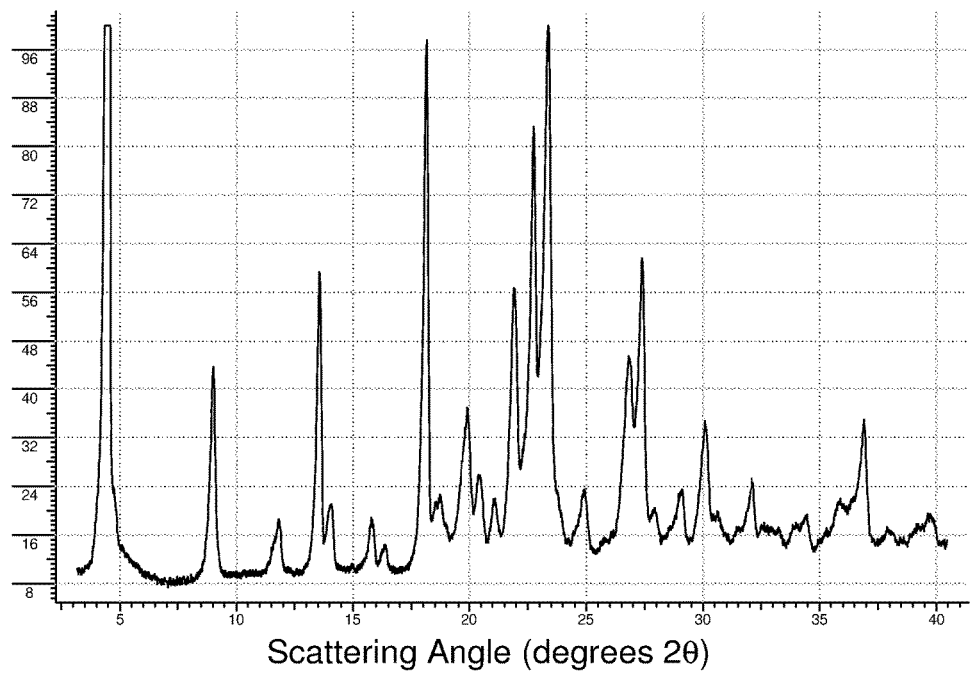
FIG. 13a is an x-ray powder diffraction pattern of the L-theanine/entacapone cocrystal.
Figure 13B:
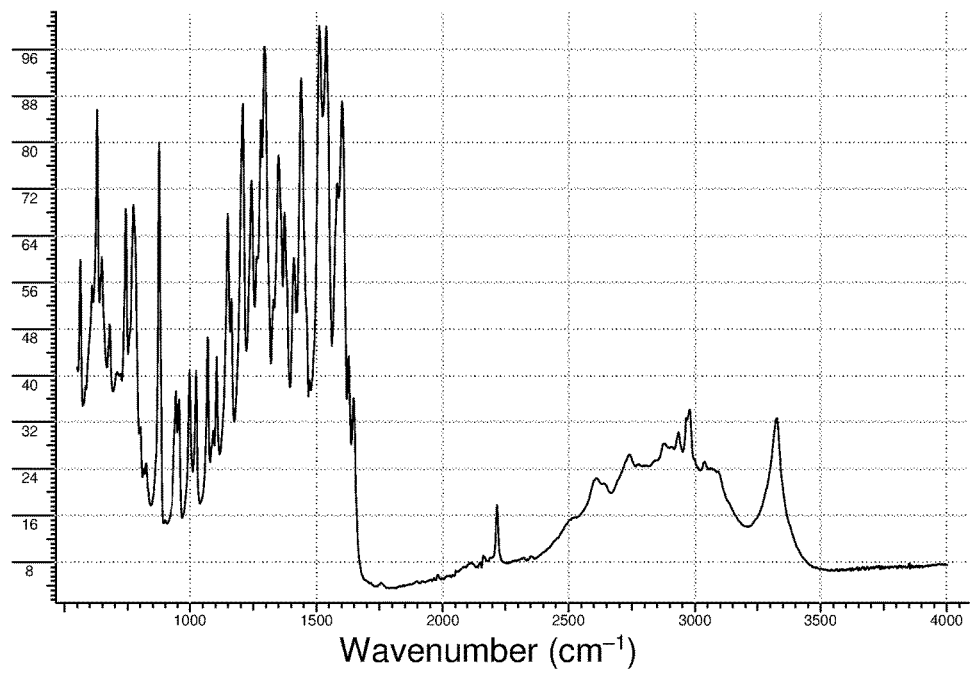
FIG. 13b is an infrared absorption spectrum of the L-theanine/entacapone cocrystal.

0.227 g of entacapone (0.744 mmol) and 0.132 g of L-theanine (0.758 mmol) were weighed directly into the bowl of an agate mortar, and wetted with 70% isopropanol to form a moderately thick slurry. The slurry was thoroughly ground at the time of mixing, and then periodically re-ground until the contents were dry. The XRPD pattern of the product is shown in FIG. 13a, while the FTIR spectrum is shown in FIG. 13b. The DSC melting endotherm of the product was characterized by a peak maximum at 160° C.

Example 14

Figure 14A:
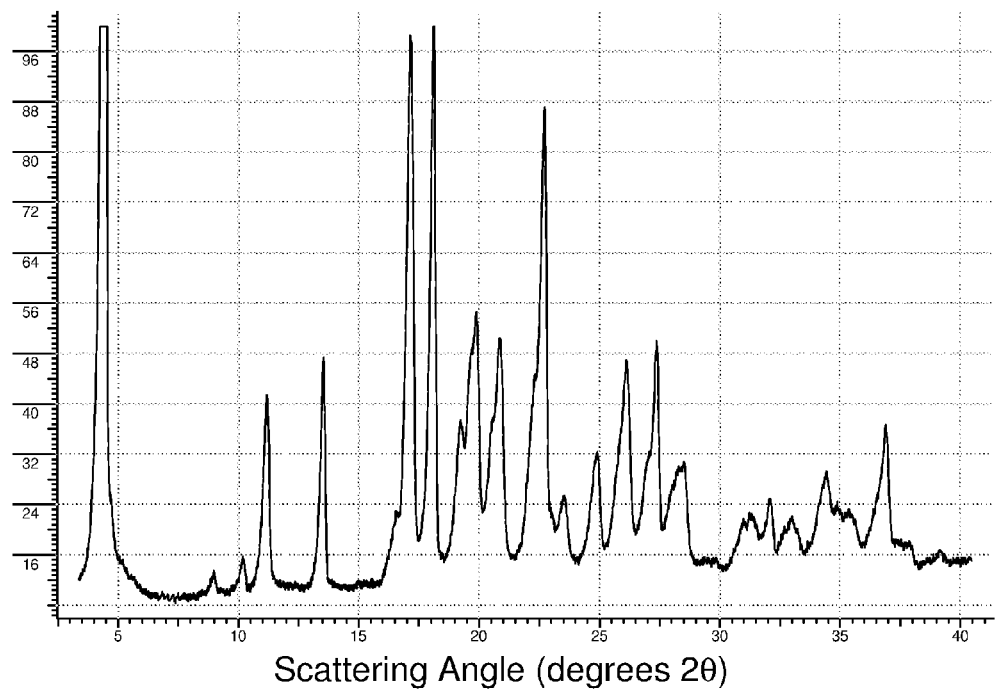
FIG. 14a is an x-ray powder diffraction pattern of the L-theanine/epinephrine cocrystal.
Figure 14B:
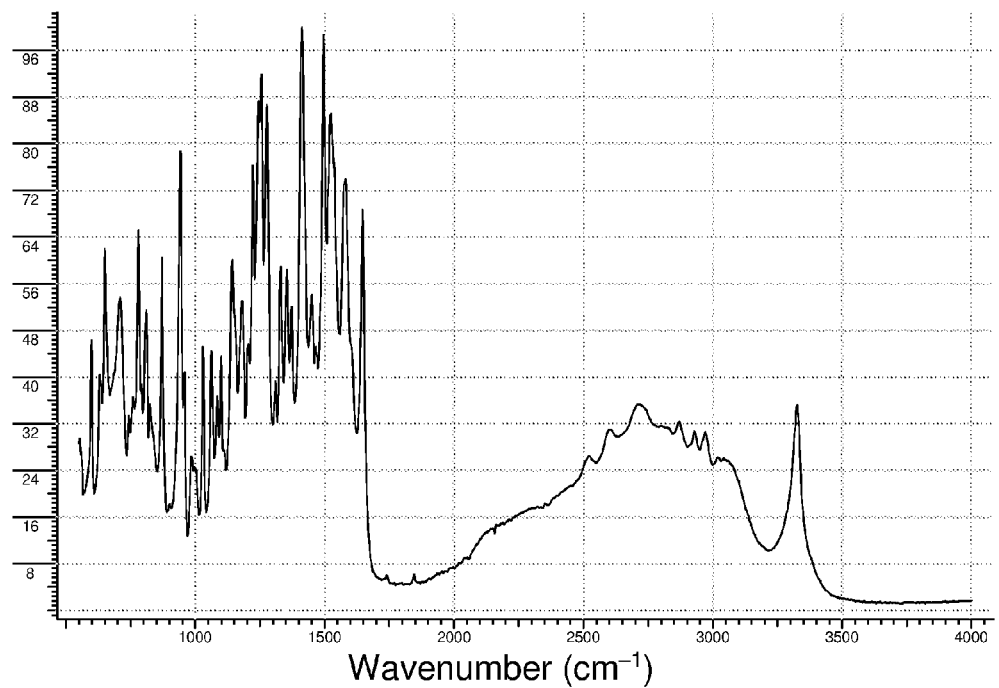
FIG. 14b is an infrared absorption spectrum of the L-theanine/epinephrine cocrystal.

0.316 g of epinephrine (1.725 mmol) and 0.305 g of L-theanine (1.751 mmol) were weighed directly into the bowl of an agate mortar, and wetted with 70% isopropanol to form a moderately thick slurry. The slurry was thoroughly ground at the time of mixing, and then periodically re-ground until the contents were dry. The XRPD pattern of the product is shown in FIG. 14a, while the FTIR spectrum is shown in FIG. 14b. The DSC melting endotherm of the product was characterized by a peak maximum at 205° C.

Example 15

Figure 15A:
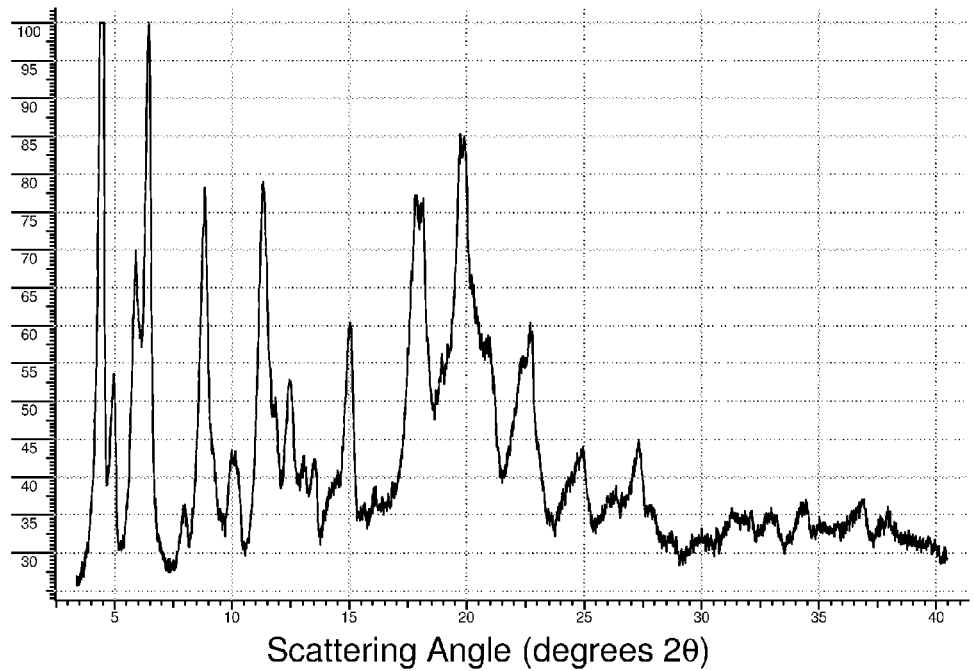
FIG. 15a is an x-ray powder diffraction pattern of the L-theanine/erythromycin cocrystal.
Figure 15B:
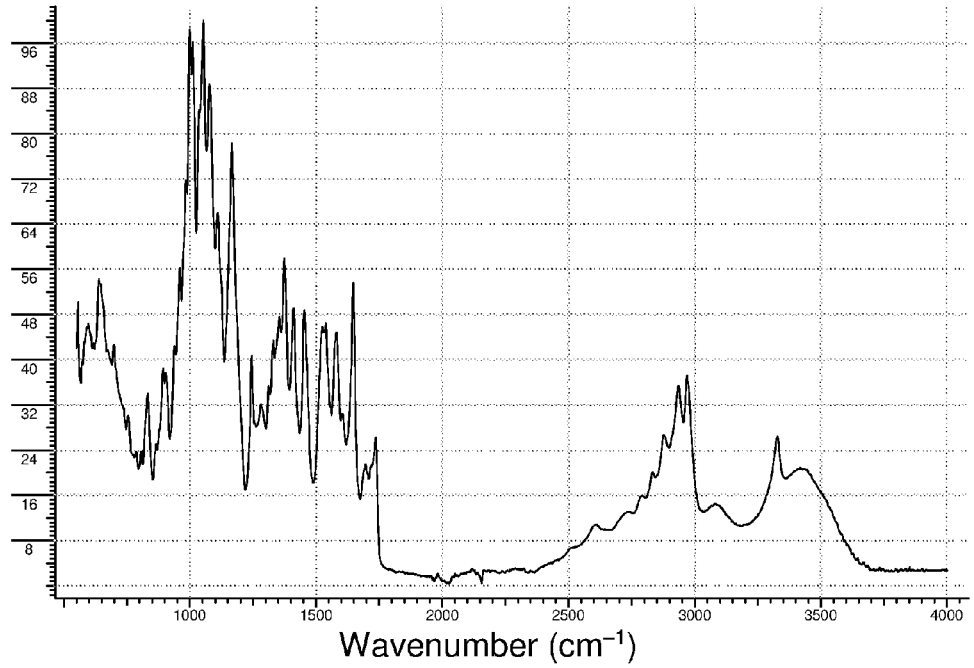
FIG. 15b is an infrared absorption spectrum of the L-theanine/erythromycin cocrystal.

0.417 g of erythromycin (0.568 mmol) and 0.101 g of L-theanine (0.580 mmol) were weighed directly into the bowl of an agate mortar, and wetted with 70% isopropanol to form a moderately thick slurry. The slurry was thoroughly ground at the time of mixing, and then periodically re-ground until the contents were dry. The XRPD pattern of the product is shown in FIG. 15a, while the FTIR spectrum is shown in FIG. 15b. The DSC melting endotherm of the product was characterized by a peak maximum at 219° C.

Example 16

Figure 16A:
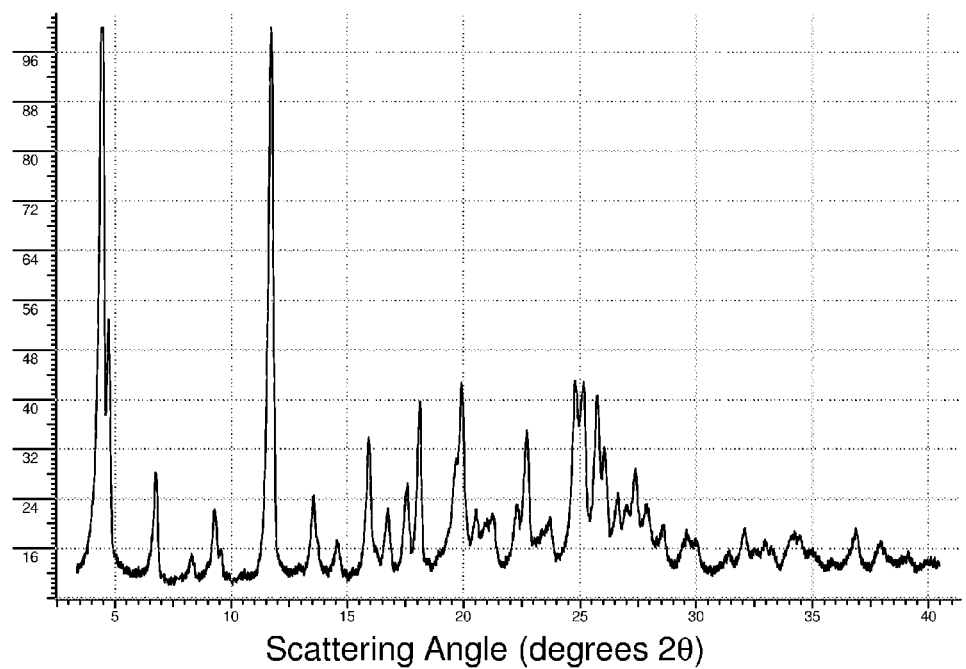
FIG. 16a is an x-ray powder diffraction pattern of the L-theanine/febuxostat cocrystal.
Figure 16B:
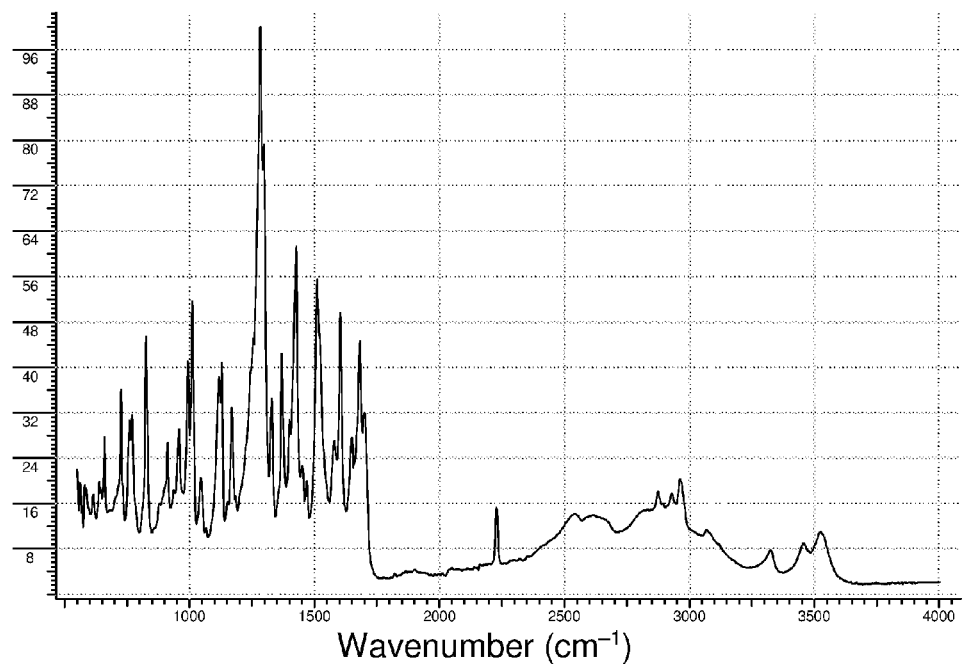
FIG. 16b is an infrared absorption spectrum of the L-theanine/febuxostat cocrystal.

0.326 g of febuxostat (1.030 mmol) and 0.180 g of L-theanine (1.033 mmol) were weighed directly into the bowl of an agate mortar, and wetted with 70% isopropanol to form a moderately thick slurry. The slurry was thoroughly ground at the time of mixing, and then periodically re-ground until the contents were dry. The XRPD pattern of the product is shown in FIG. 16a, while the FTIR spectrum is shown in FIG. 16b. The DSC melting endotherm of the product was characterized by a peak maximum at 182° C.

Example 17

Figure 17A:
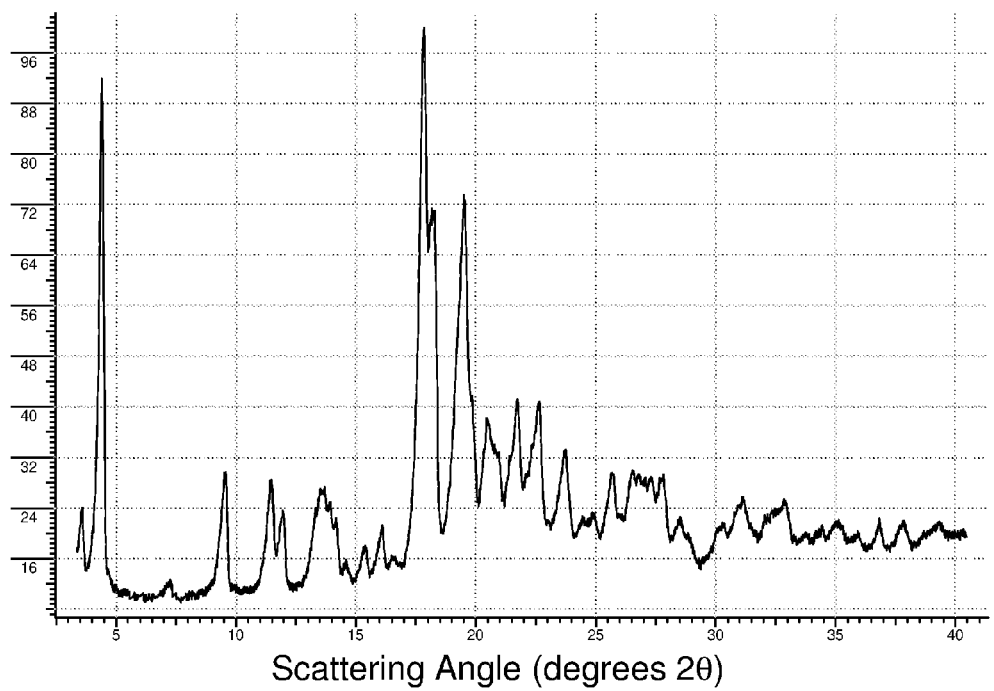
FIG. 17a is an x-ray powder diffraction pattern of the L-theanine/fexofenadine cocrystal.
Figure 17B:
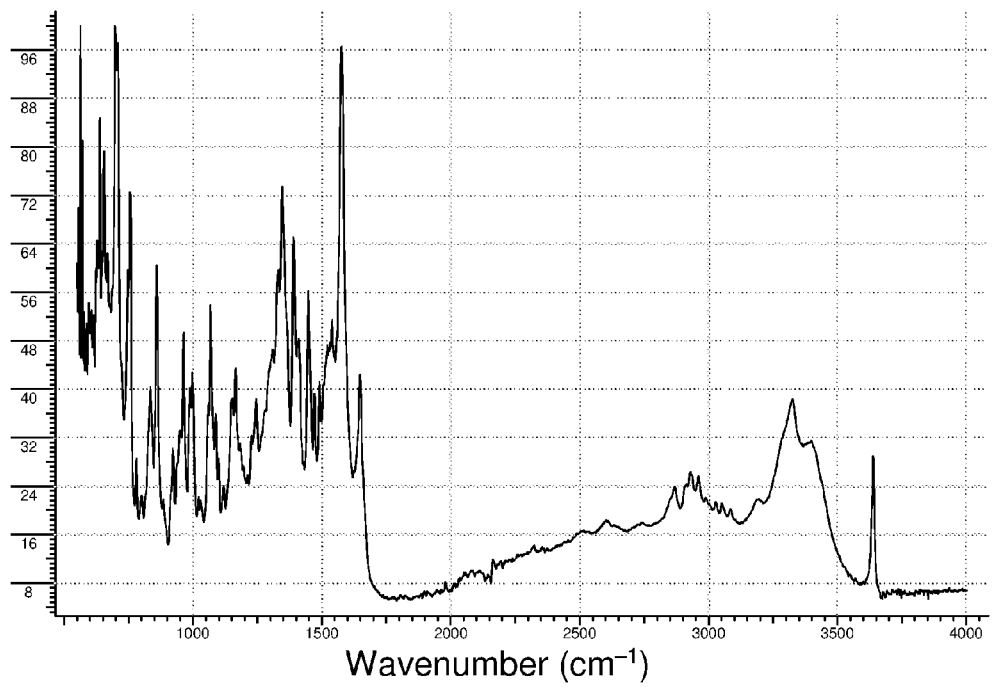
FIG. 17b is an infrared absorption spectrum of the L-theanine/fexofenadine cocrystal.

0.330 g of fexofenadine (0.658 mmol) and 0.119 g of L-theanine (0.683 mmol) were weighed directly into the bowl of an agate mortar, and wetted with 70% isopropanol to form a moderately thick slurry. The slurry was thoroughly ground at the time of mixing, and then periodically re-ground until the contents were dry. The XRPD pattern of the product is shown in FIG. 17a, while the FTIR spectrum is shown in FIG. 17b. The DSC melting endotherm of the product was characterized by a peak maximum at 206° C.

Example 18

Figure 18A:
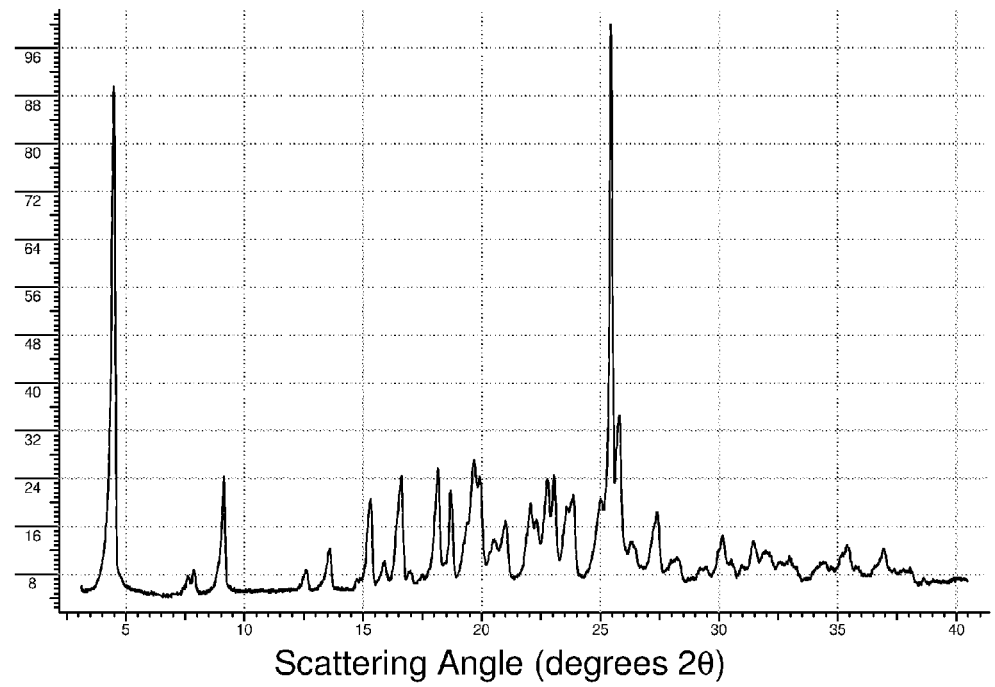
FIG. 18a is an x-ray powder diffraction pattern of the L-theanine/fluconazole cocrystal.
Figure 18B:
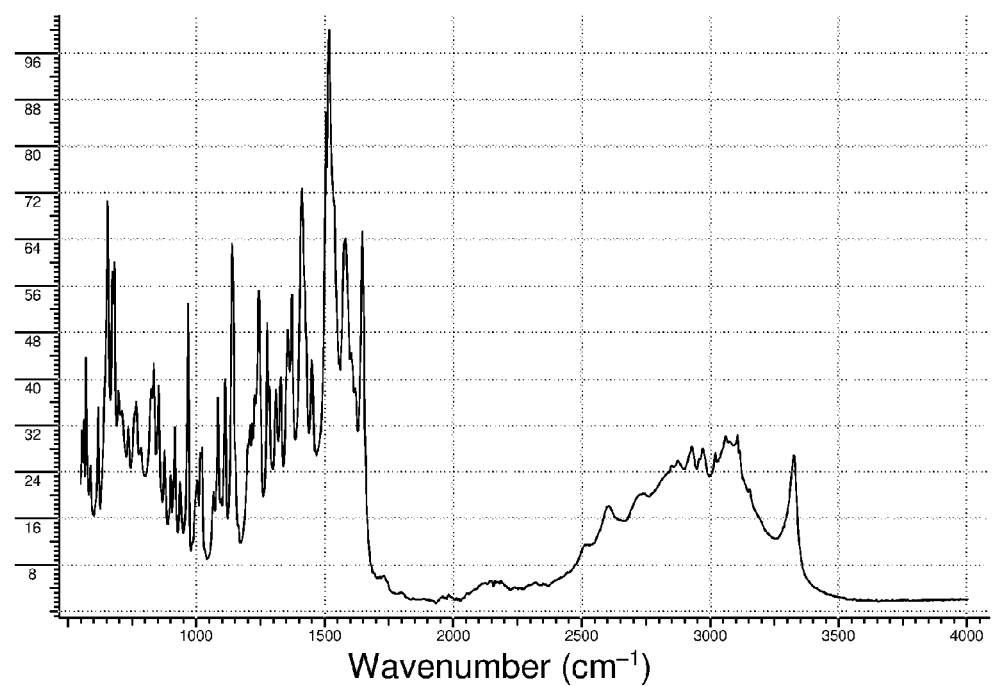
FIG. 18b is an infrared absorption spectrum of the L-theanine/fluconazole cocrystal.

0.355 g of fluconazole (1.159 mmol) and 0.204 g of L-theanine (1.171 mmol) were weighed directly into the bowl of an agate mortar, and wetted with 70% isopropanol to form a moderately thick slurry. The slurry was thoroughly ground at the time of mixing, and then periodically re-ground until the contents were dry. The XRPD pattern of the product is shown in FIG. 18a, while the FTIR spectrum is shown in FIG. 18b. The DSC melting endotherm of the product was characterized by a peak maximum at 102° C.

Example 19

Figure 19A:
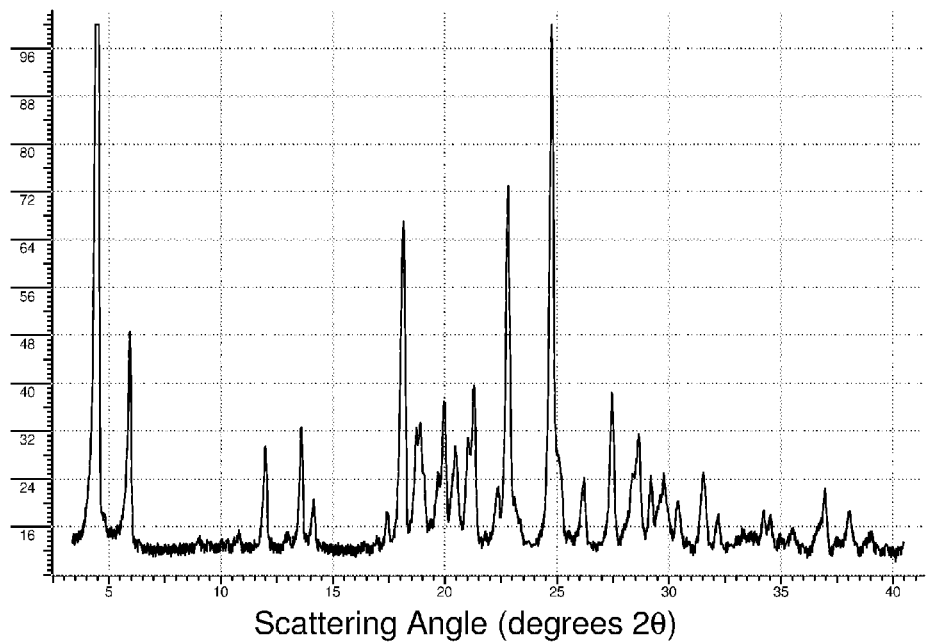
FIG. 19a is an x-ray powder diffraction pattern of the L-theanine/furosemide cocrystal.
Figure 19B:
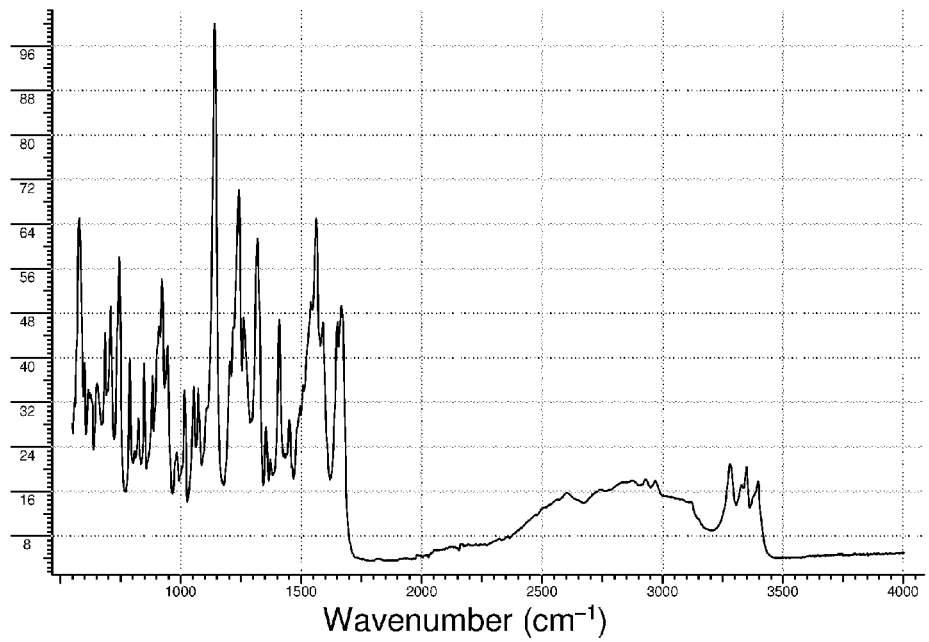
FIG. 19b is an infrared absorption spectrum of the L-theanine/furosemide cocrystal.

0.181 g of furosemide (0.547 mmol) and 0.094 g of L-theanine (0.540 mmol) were weighed directly into the bowl of an agate mortar, and wetted with 70% isopropanol to form a moderately thick slurry. The slurry was thoroughly ground at the time of mixing, and then periodically re-ground until the contents were dry. The XRPD pattern of the product is shown in FIG. 19a, while the FTIR spectrum is shown in FIG. 19b. The DSC melting endotherm of the product was characterized by a peak maximum at 193° C.

Example 20

Figure 20A:
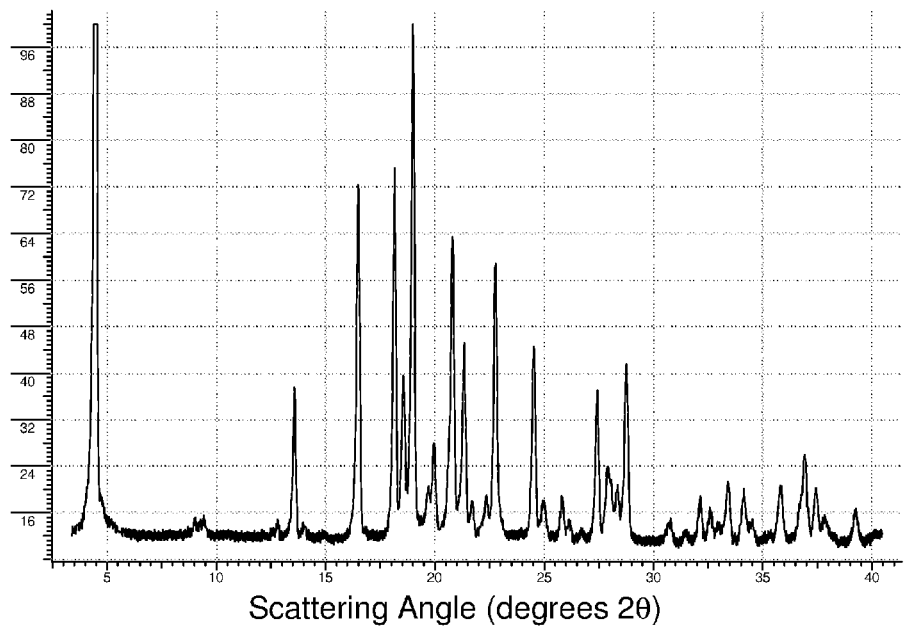
FIG. 20a is an x-ray powder diffraction pattern of the L-theanine/hydrochlorothiazide cocrystal.
Figure 20B:
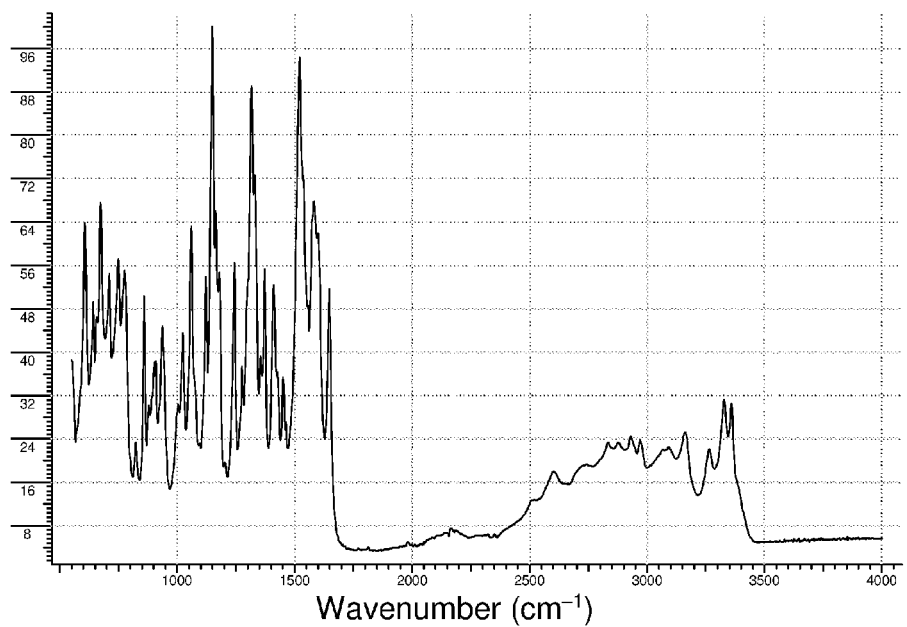
FIG. 20b is an infrared absorption spectrum of the L-theanine/hydrochlorothiazide cocrystal.

0.408 g of hydrochlorothiazide (1.370 mmol) and 0.239 g of L-theanine (1.372 mmol) were weighed directly into the bowl of an agate mortar, and wetted with 70% isopropanol to form a moderately thick slurry. The slurry was thoroughly ground at the time of mixing, and then periodically re-ground until the contents were dry. The XRPD pattern of the product is shown in FIG. 20a, while the FTIR spectrum is shown in FIG. 20b. The DSC melting endotherm of the product was characterized by a peak maximum at 204° C.

Example 21

Figure 21A:
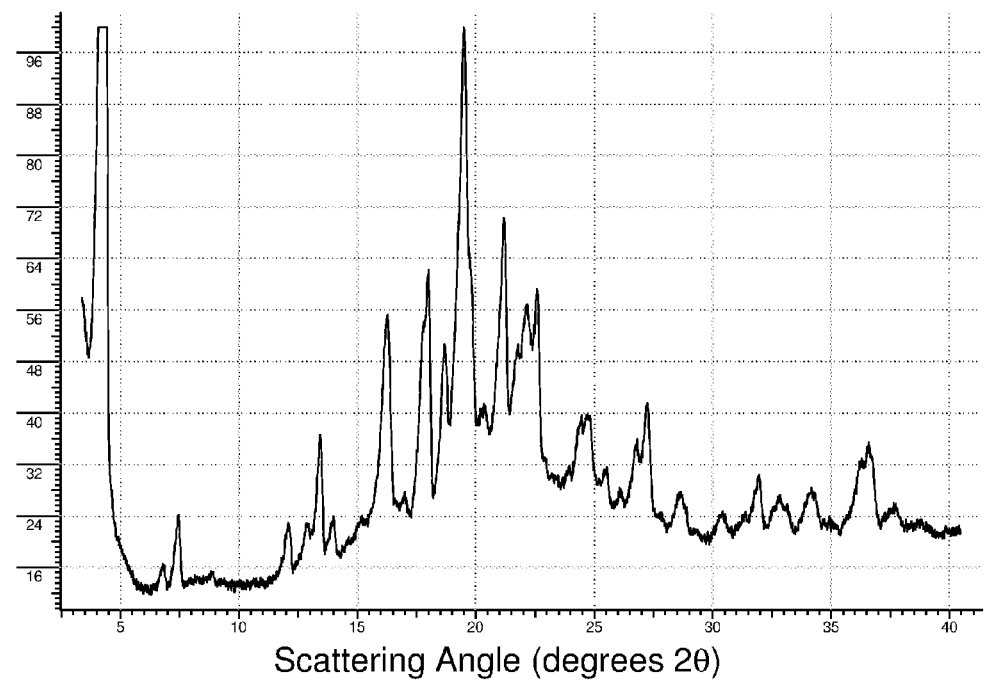
FIG. 21a is an x-ray powder diffraction pattern of the L-theanine/R-ibuprofen cocrystal.
Figure 21B:
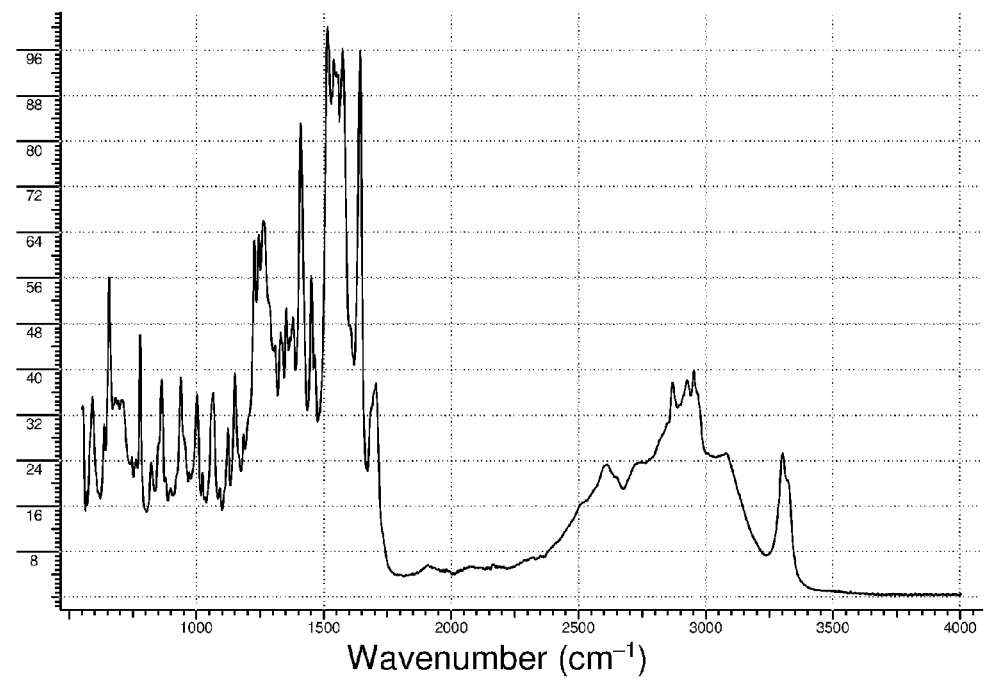
FIG. 21b is an infrared absorption spectrum of the L-theanine/R-ibuprofen cocrystal.

0.246 g of R-ibuprofen (1.193 mmol) and 0.213 g of L-theanine (1.223 mmol) were weighed directly into the bowl of an agate mortar, and wetted with 70% isopropanol to form a moderately thick slurry. The slurry was thoroughly ground at the time of mixing, and then periodically re-ground until the contents were dry. The XRPD pattern of the product is shown in FIG. 21a, while the FTIR spectrum is shown in FIG. 21b. The DSC melting endotherm of the product was characterized by a peak maximum at 51° C.

Example 22

Figure 22A:
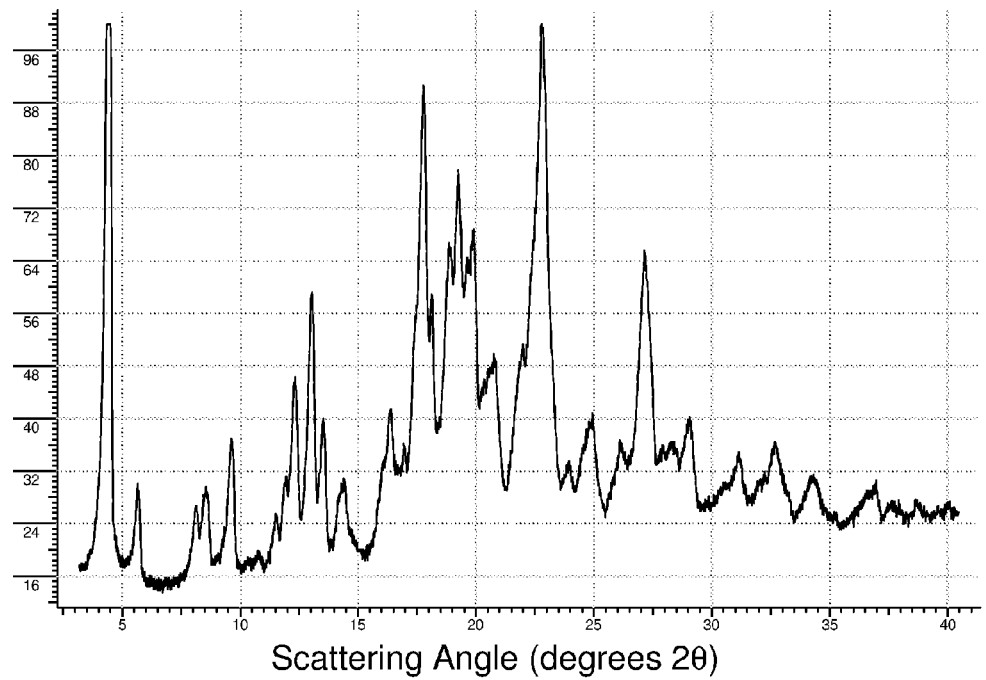
FIG. 22a is an x-ray powder diffraction pattern of the L-theanine/irinotecan cocrystal.
Figure 22B:
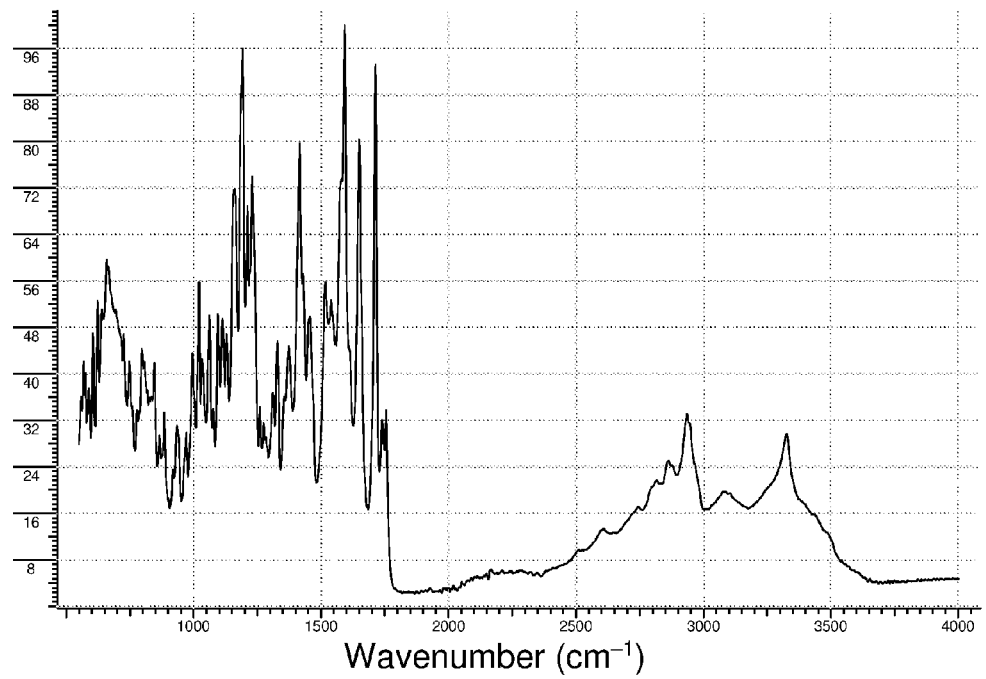
FIG. 22b is an infrared absorption spectrum of the L-theanine/irinotecan cocrystal.

0.309 g of irinotecan (0.527 mmol) and 0.094 g of L-theanine (0.540 mmol) were weighed directly into the bowl of an agate mortar, and wetted with 70% isopropanol to form a moderately thick slurry. The slurry was thoroughly ground at the time of mixing, and then periodically re-ground until the contents were dry. The XRPD pattern of the product is shown in FIG. 22a, while the FTIR spectrum is shown in FIG. 22b. The DSC melting endotherm of the product was characterized by a peak maximum at 218° C.

Example 23

Figure 23A:
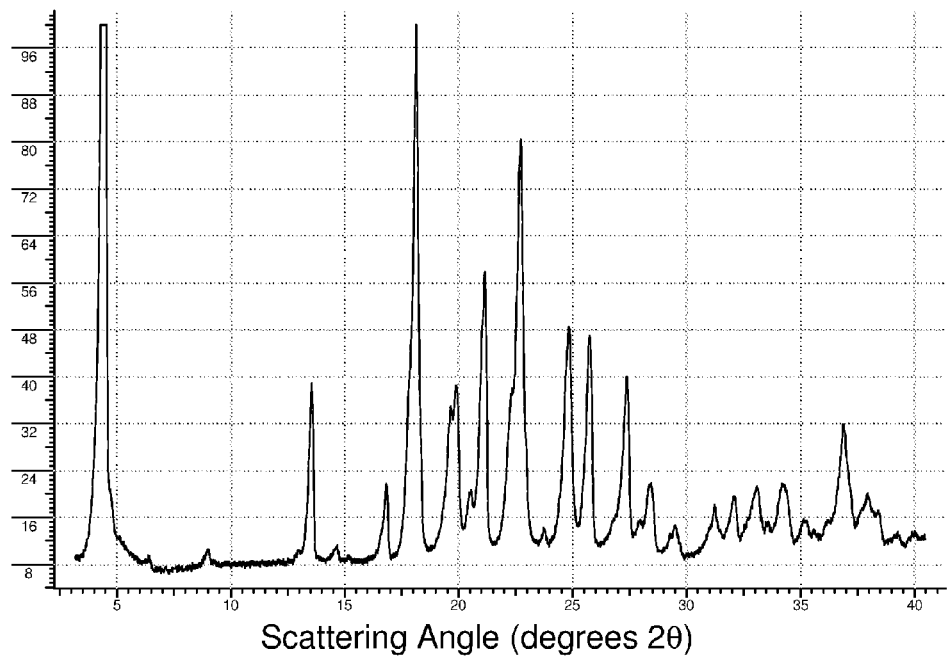
FIG. 23a is an x-ray powder diffraction pattern of the L-theanine/levodopa cocrystal.
Figure 23B:
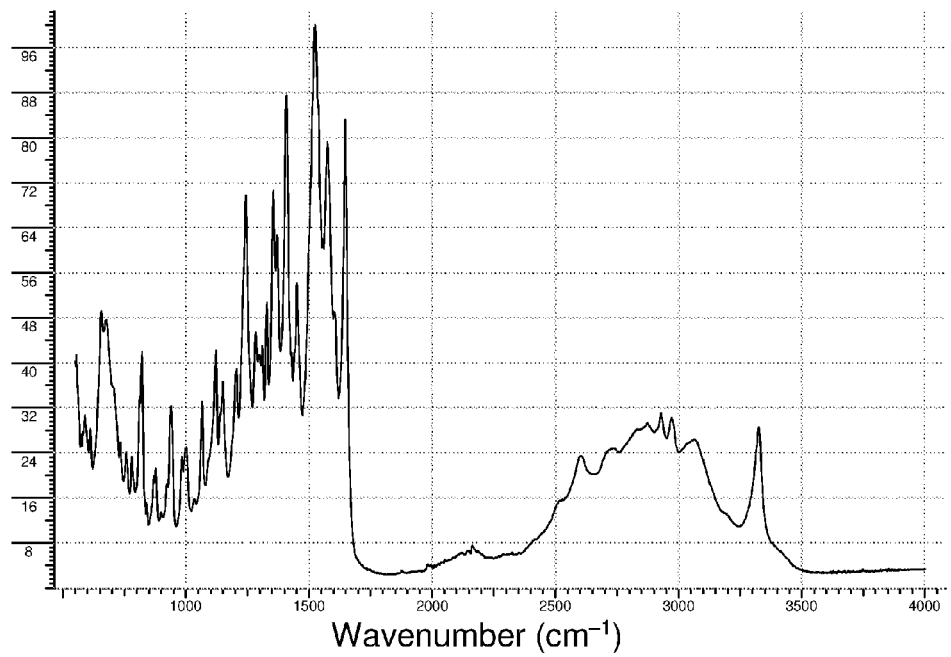
FIG. 23b is an infrared absorption spectrum of the L-theanine/levodopa cocrystal.

0.215 g of levodopa (1.090 mmol) and 0.191 g of L-theanine (1.096 mmol) were weighed directly into the bowl of an agate mortar, and wetted with 70% isopropanol to form a moderately thick slurry. The slurry was thoroughly ground at the time of mixing, and then periodically re-ground until the contents were dry. The XRPD pattern of the product is shown in FIG. 23a, while the FTIR spectrum is shown in FIG. 23b. The DSC melting endotherm of the product was characterized by a peak maximum at 211° C.

Example 24

Figure 24A:
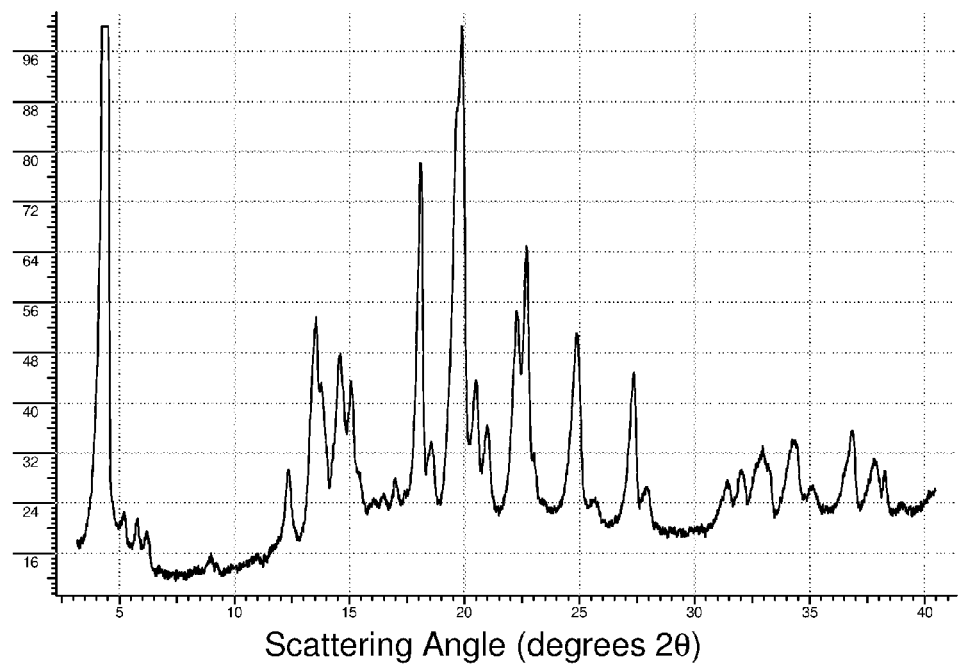
FIG. 24a is an x-ray powder diffraction pattern of the L-theanine/memantine cocrystal.
Figure 24B:
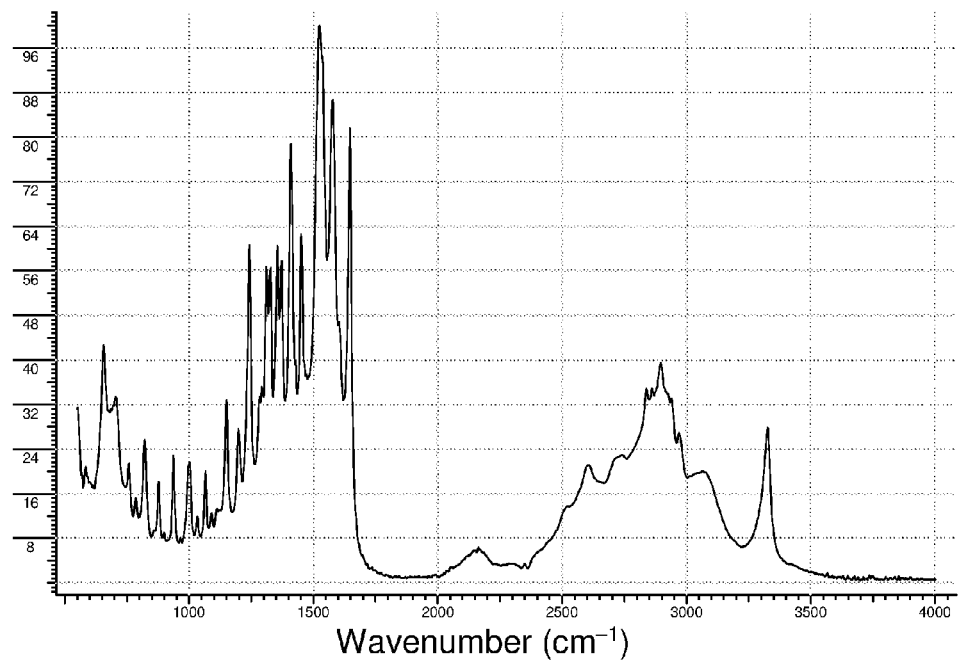
FIG. 24b is an infrared absorption spectrum of the L-theanine/memantine cocrystal.

0.142 g of memantine (0.792 mmol) and 0.140 g of L-theanine (0.804 mmol) were weighed directly into the bowl of an agate mortar, and wetted with 70% isopropanol to form a moderately thick slurry. The slurry was thoroughly ground at the time of mixing, and then periodically re-ground until the contents were dry. The XRPD pattern of the product is shown in FIG. 24a, while the FTIR spectrum is shown in FIG. 24b. The DSC melting endotherm of the product was characterized by a peak maximum at 207° C.

Example 25

Figure 25A:
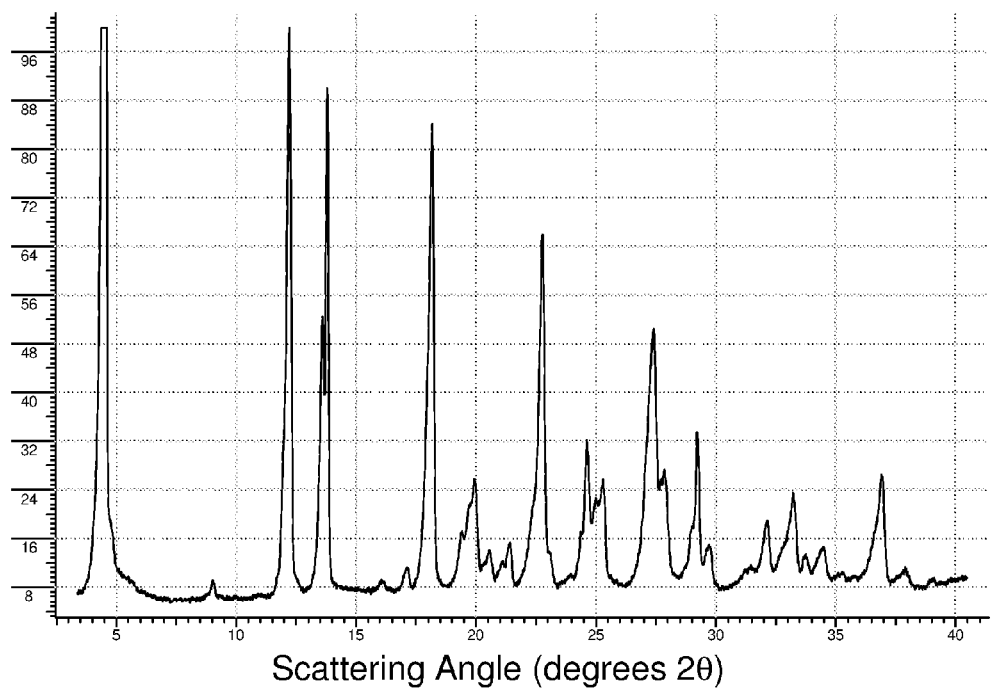
FIG. 25a is an x-ray powder diffraction pattern of the L-theanine/metronidazole cocrystal.
Figure 25B:
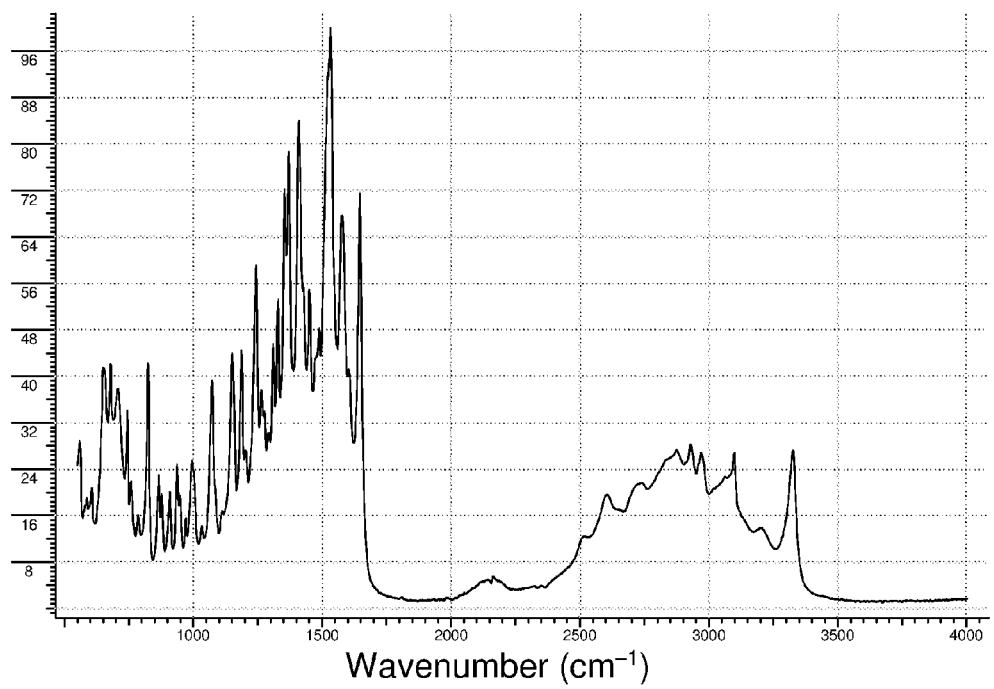
FIG. 25b is an infrared absorption spectrum of the L-theanine/metronidazole cocrystal.

0.335 g of metronidazole (1.957 mmol) and 0.348 g of L-theanine (1.998 mmol) were weighed directly into the bowl of an agate mortar, and wetted with 70% isopropanol to form a moderately thick slurry. The slurry was thoroughly ground at the time of mixing, and then periodically re-ground until the contents were dry. The XRPD pattern of the product is shown in FIG. 25a, while the FTIR spectrum is shown in FIG. 25b. The DSC melting endotherm of the product was characterized by a peak maximum at 160° C.

Example 26

Figure 26A:
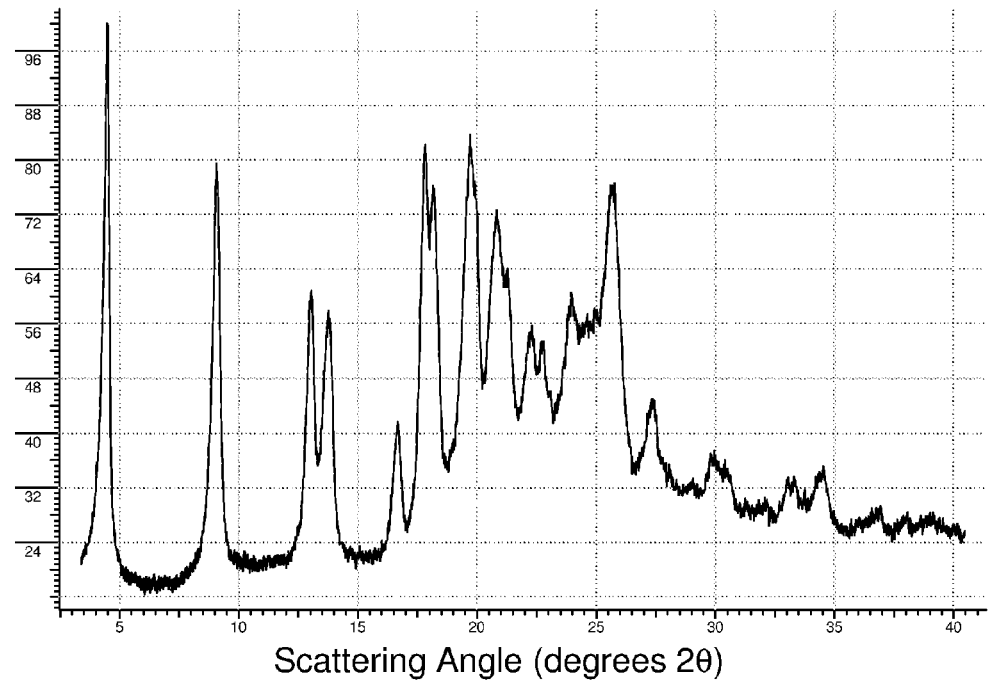
FIG. 26a is an x-ray powder diffraction pattern of the L-theanine/nilotinib cocrystal.
Figure 26B:
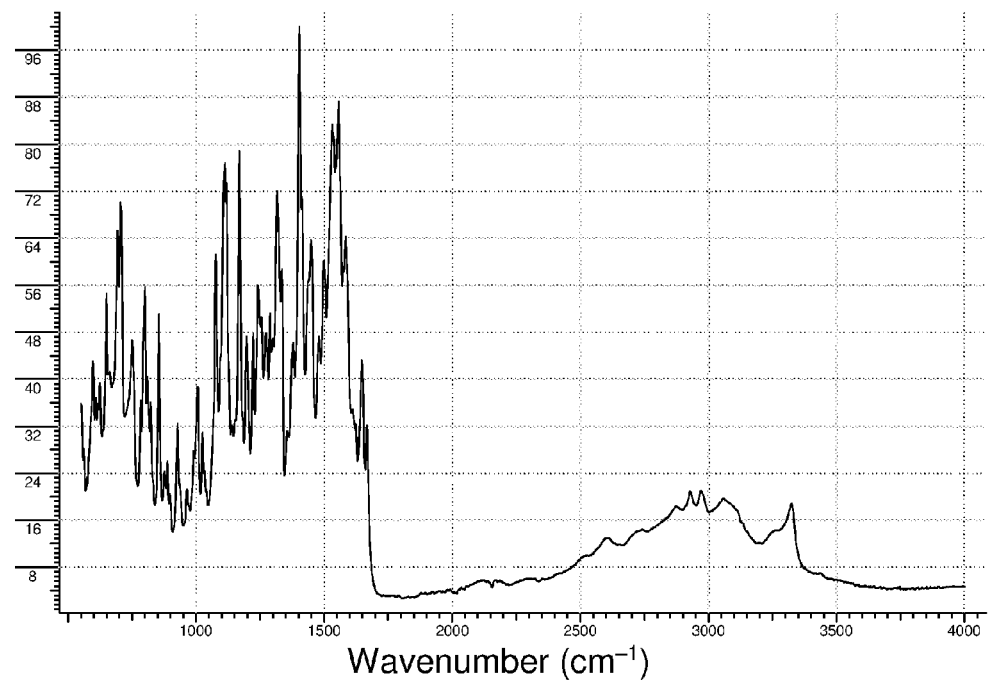
FIG. 26b is an infrared absorption spectrum of the L-theanine/nilotinib cocrystal.

0.271 g of nilotinib (0.512 mmol) and 0.090 g of L-theanine (0.517 mmol) were weighed directly into the bowl of an agate mortar, and wetted with 70% isopropanol to form a moderately thick slurry. The slurry was thoroughly ground at the time of mixing, and then periodically re-ground until the contents were dry. The XRPD pattern of the product is shown in FIG. 26a, while the FTIR spectrum is shown in FIG. 26b. The DSC melting endotherm of the product was characterized by a peak maximum at 211° C.

Example 27

Figure 27A:
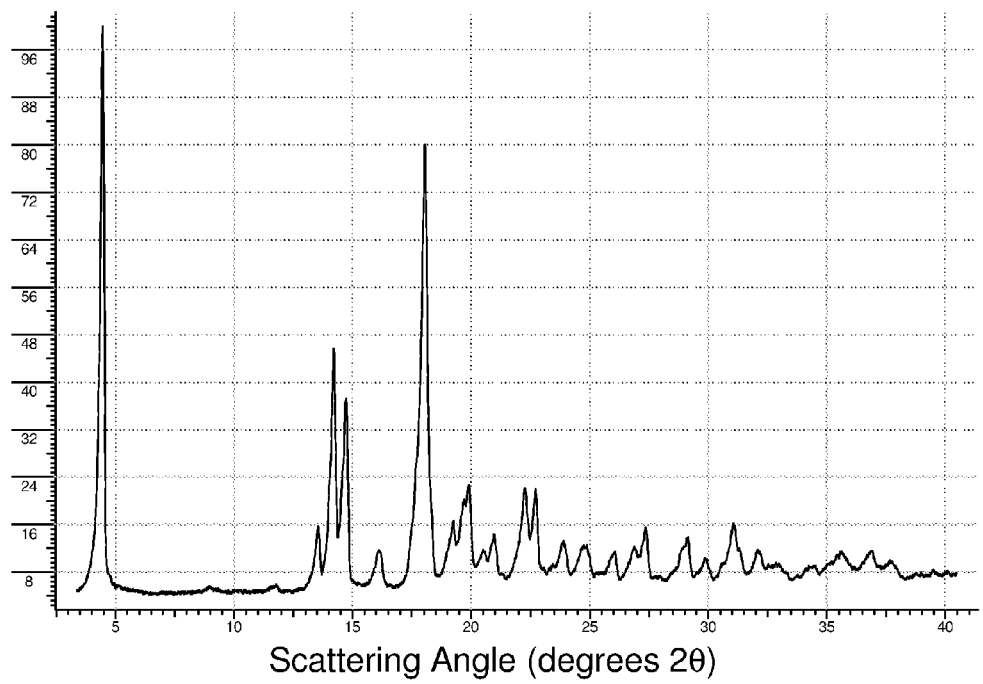
FIG. 27a is an x-ray powder diffraction pattern of the L-theanine/prednisone cocrystal.
Figure 27B:
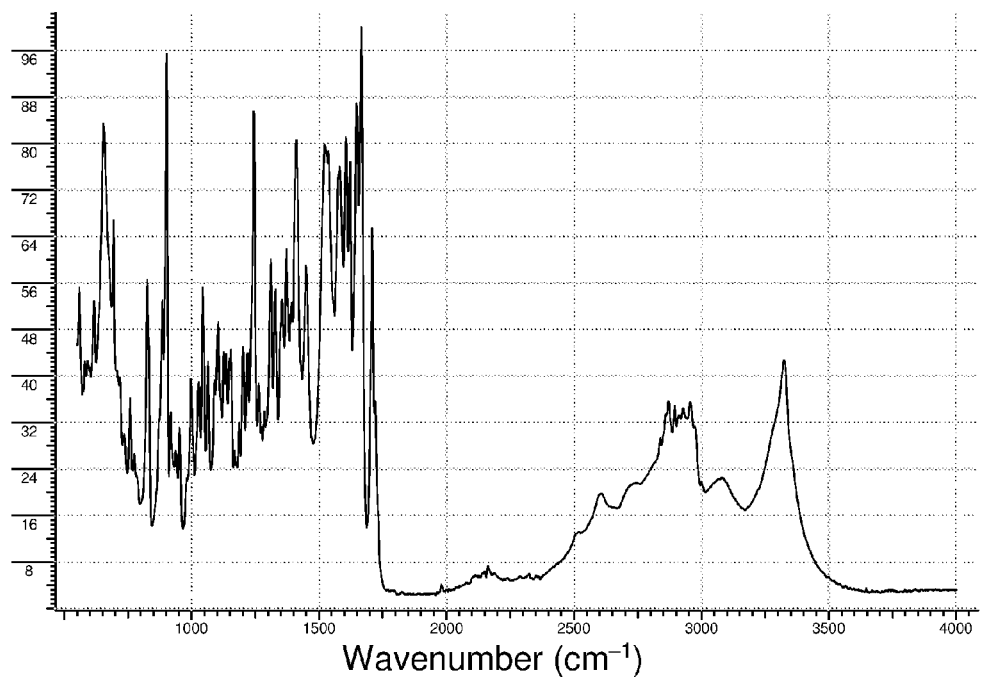
FIG. 27b is an infrared absorption spectrum of the L-theanine/prednisone cocrystal.

0.206 g of prednisone (0.575 mmol) and 0.103 g of L-theanine (0.591 mmol) were weighed directly into the bowl of an agate mortar, and wetted with 70% isopropanol to form a moderately thick slurry. The slurry was thoroughly ground at the time of mixing, and then periodically re-ground until the contents were dry. The XRPD pattern of the product is shown in FIG. 27a, while the FTIR spectrum is shown in FIG. 27b. The DSC melting endotherm of the product was characterized by a peak maximum at 201° C.

Example 28

Figure 28A:
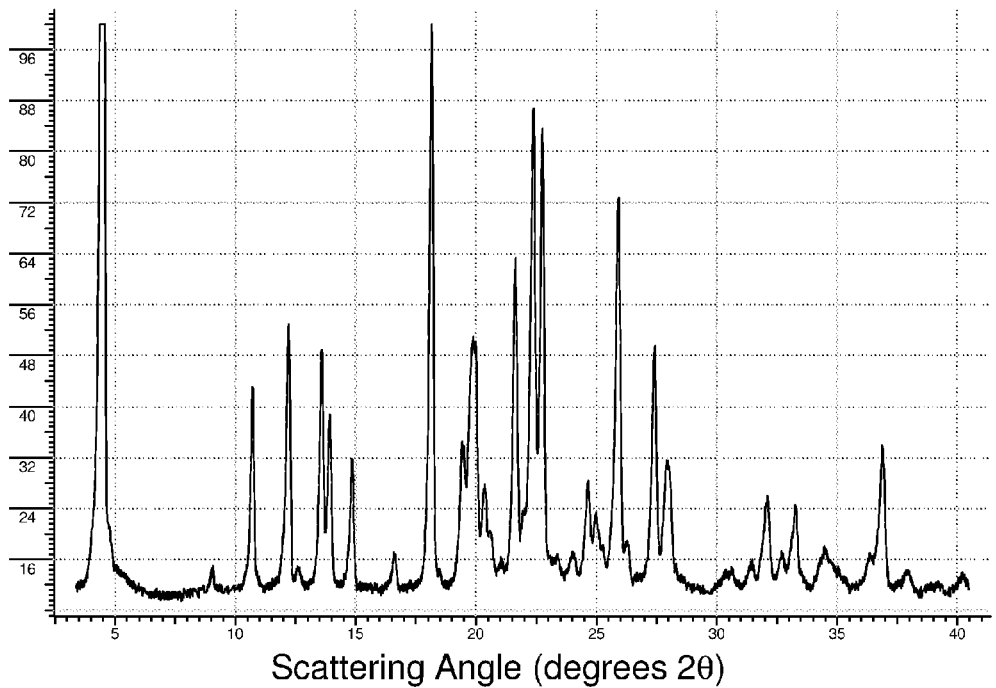
FIG. 28a is an x-ray powder diffraction pattern of the L-theanine/sulfamethoxazole amoxicillin cocrystal.
Figure 28B:
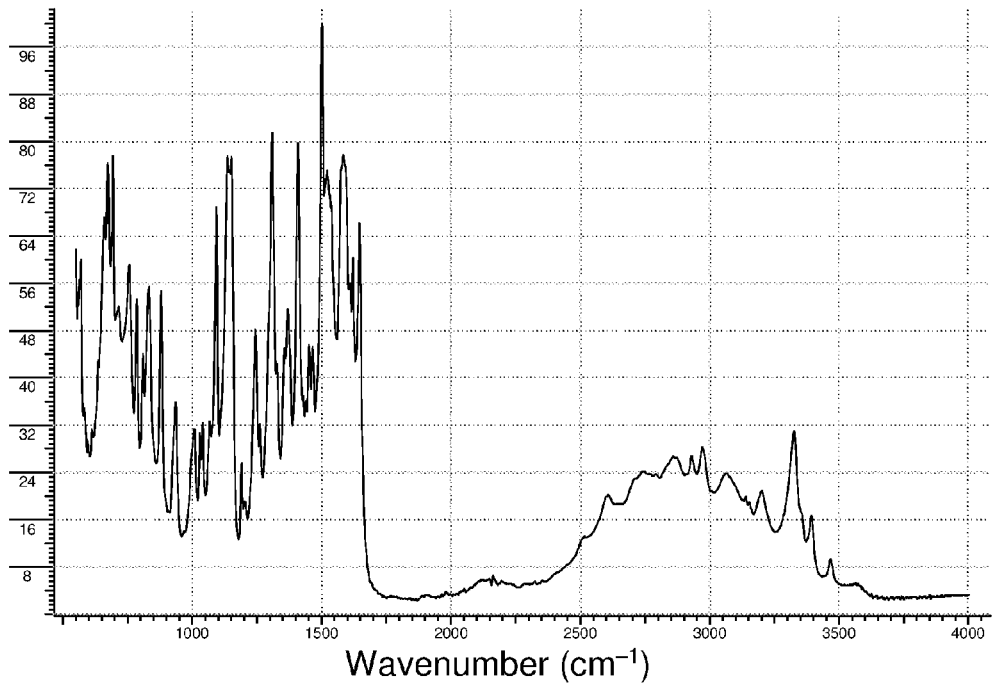
FIG. 28b is an infrared absorption spectrum of the L-theanine/sulfamethoxazole cocrystal.

0.368 g of sulfamethoxazole (1.453 mmol) and 0.259 g of L-theanine (1.487 mmol) were weighed directly into the bowl of an agate mortar, and wetted with 70% isopropanol to form a moderately thick slurry. The slurry was thoroughly ground at the time of mixing, and then periodically re-ground until the contents were dry. The XRPD pattern of the product is shown in FIG. 28a, while the FTIR spectrum is shown in FIG. 28b. The DSC melting endotherm of the product was characterized by a peak maximum at 169° C.

Example 29

Figure 29A:
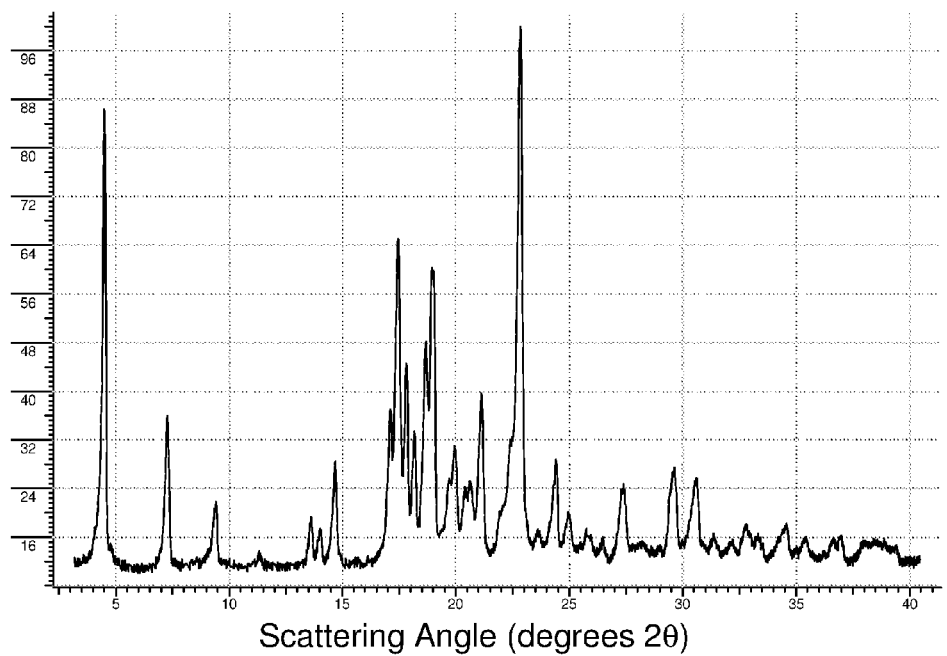
FIG. 29a is an x-ray powder diffraction pattern of the L-theanine/sumitriptan cocrystal.
Figure 29B:
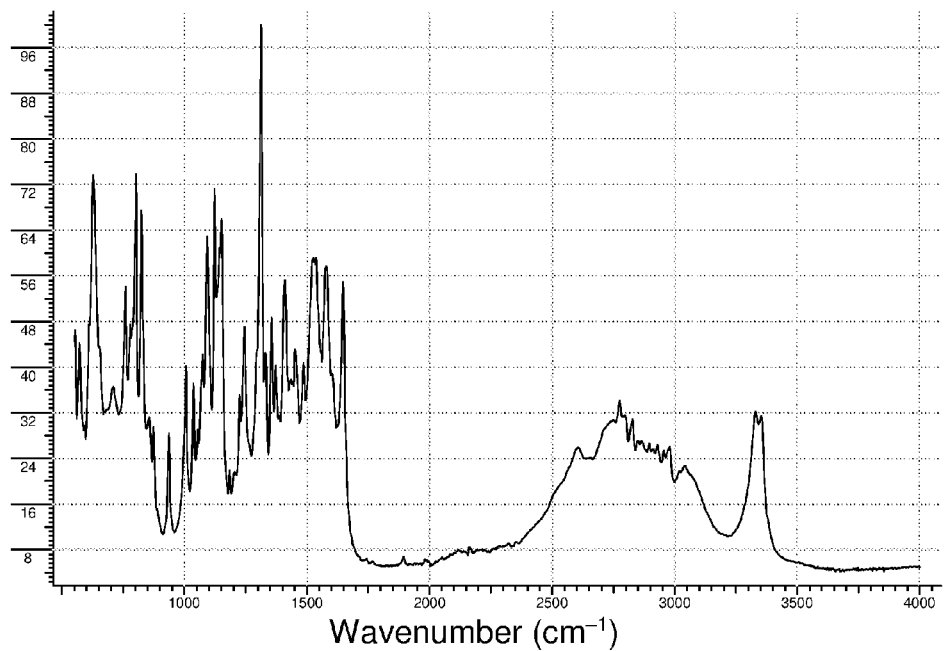
FIG. 29b is an infrared absorption spectrum of the L-theanine/sumitriptan cocrystal.

0.425 g of sumitriptan (0.963 mmol) and 0.168 g of L-theanine (0.964 mmol) were weighed directly into the bowl of an agate mortar, and wetted with 70% isopropanol to form a moderately thick slurry. The slurry was thoroughly ground at the time of mixing, and then periodically re-ground until the contents were dry. The XRPD pattern of the product is shown in FIG. 29a, while the FTIR spectrum is shown in FIG. 29b. The DSC melting endotherm of the product was characterized by a peak maximum at 173° C.

Example 30

Figure 30A:
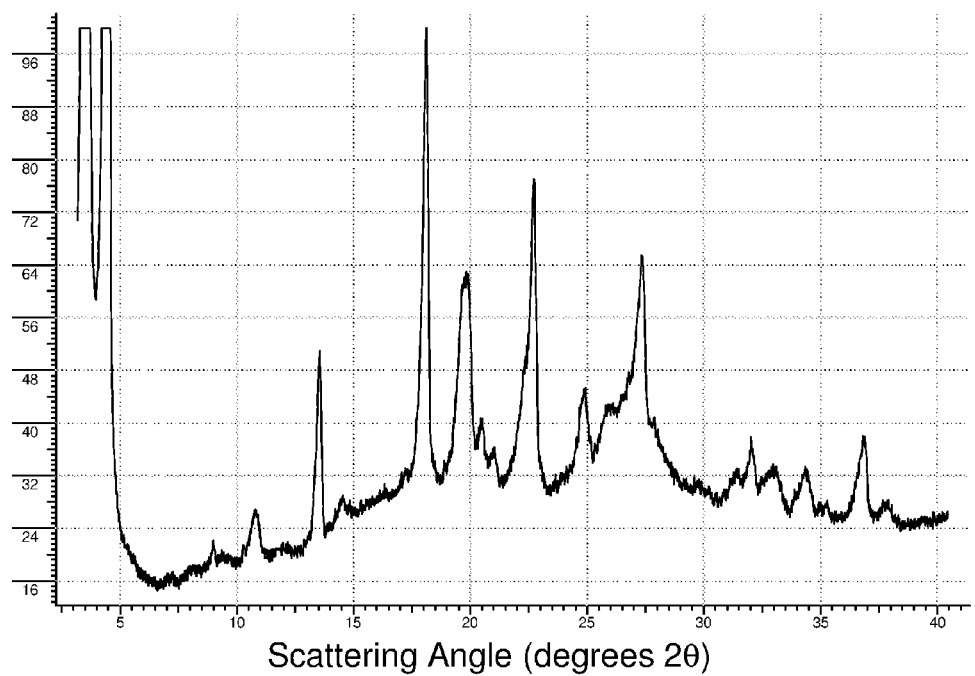
FIG. 30a is an x-ray powder diffraction pattern of the L-theanine/valganciclovir cocrystal.
Figure 30B:
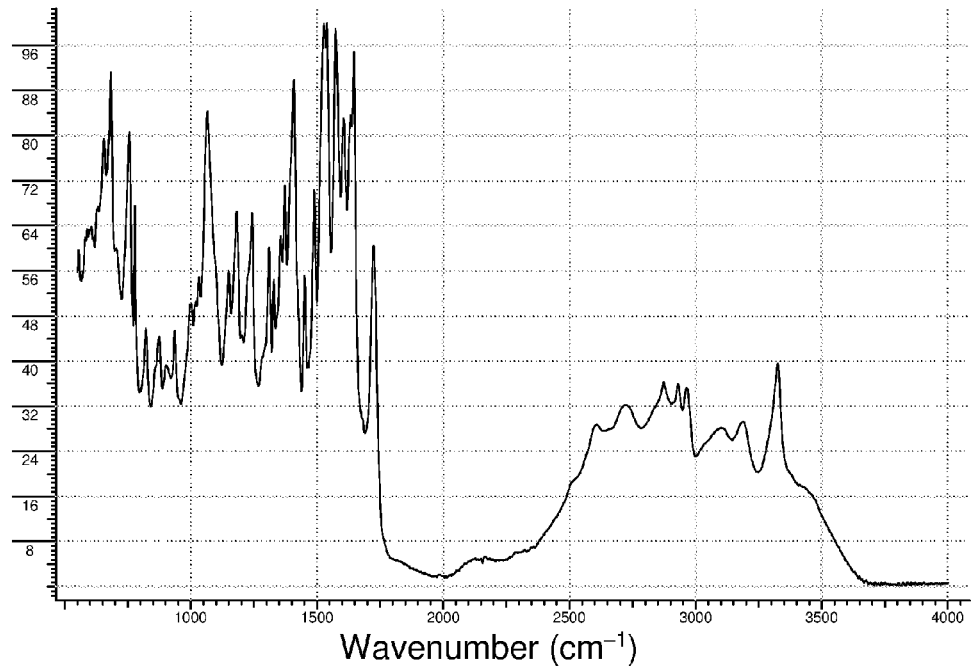
FIG. 30b is an infrared absorption spectrum of the L-theanine/valganciclovir cocrystal.

0.348 g of valganciclovir (0.982 mmol) and 0.174 g of L-theanine (0.999 mmol) were weighed directly into the bowl of an agate mortar, and wetted with 70% isopropanol to form a moderately thick slurry. The slurry was thoroughly ground at the time of mixing, and then periodically re-ground until the contents were dry. The XRPD pattern of the product is shown in FIG. 30a, while the FTIR spectrum is shown in FIG. 30b. The DSC melting endotherm of the product was characterized by a peak maximum at 212° C.

Example 31

Figure 31A:
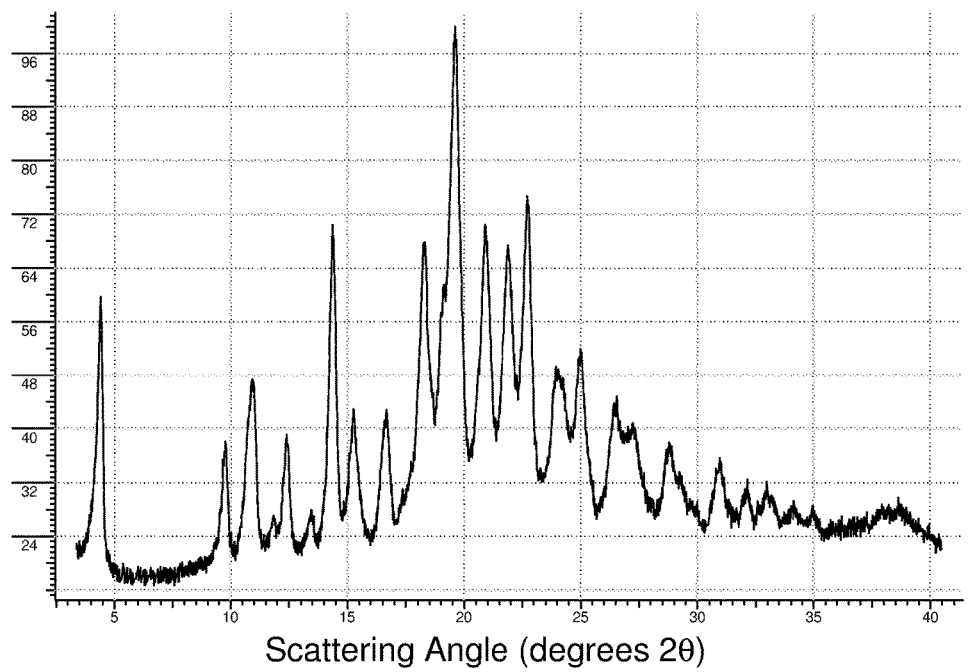
FIG. 31a is an x-ray powder diffraction pattern of the L-theanine/zafirlukast cocrystal.
Figure 31B:
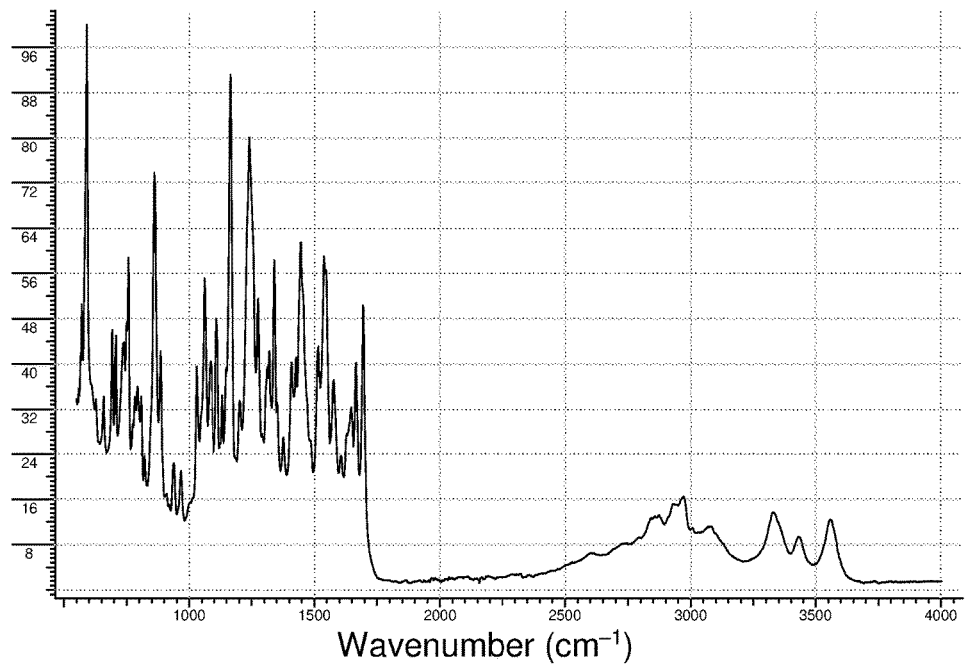
FIG. 31b is an infrared absorption spectrum of the L-theanine/zafirlukast cocrystal.

0.397 g of zafirlukast (0.690 mmol) and 0.122 g of L-theanine (0.700 mmol) were weighed directly into the bowl of an agate mortar, and wetted with 70% isopropanol to form a moderately thick slurry. The slurry was thoroughly ground at the time of mixing, and then periodically re-ground until the contents were dry. The XRPD pattern of the product is shown in FIG. 31a, while the FTIR spectrum is shown in FIG. 31b. The DSC melting endotherm of the product was characterized by a peak maximum at 211° C.

Example 32

Figure 32A:
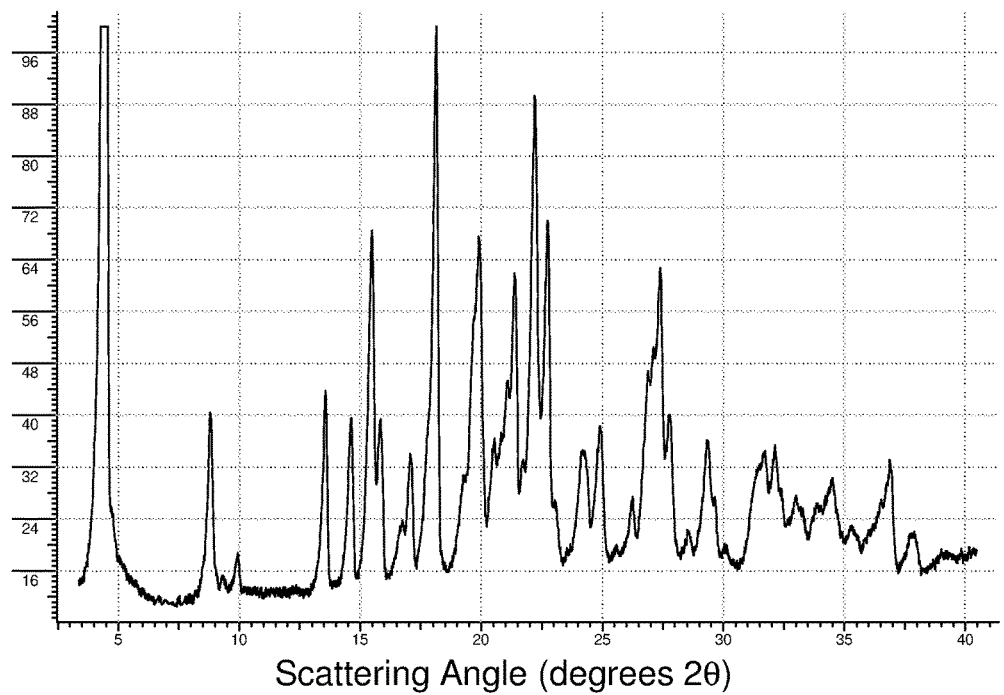
FIG. 32a is an x-ray powder diffraction pattern of the L-theanine/zidovudine cocrystal.
Figure 32B:
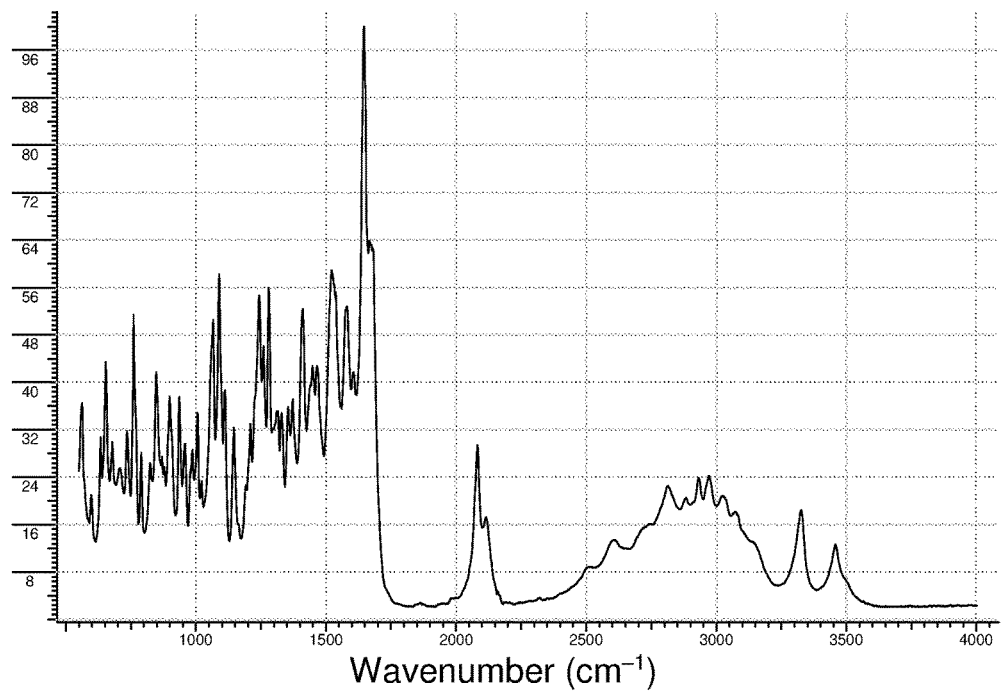
FIG. 32b is an infrared absorption spectrum of the L-theanine/zidovudine cocrystal.

0.343 g of zidovudine (1.283 mmol) and 0.226 g of L-theanine (1.297 mmol) were weighed directly into the bowl of an agate mortar, and wetted with 70% isopropanol to form a moderately thick slurry. The slurry was thoroughly ground at the time of mixing, and then periodically re-ground until the contents were dry. The XRPD pattern of the product is shown in FIG. 32a, while the FTIR spectrum is shown in FIG. 32b. The DSC melting endotherm of the product was characterized by a peak maximum at 122° C.

Example 33

Figure 33A:
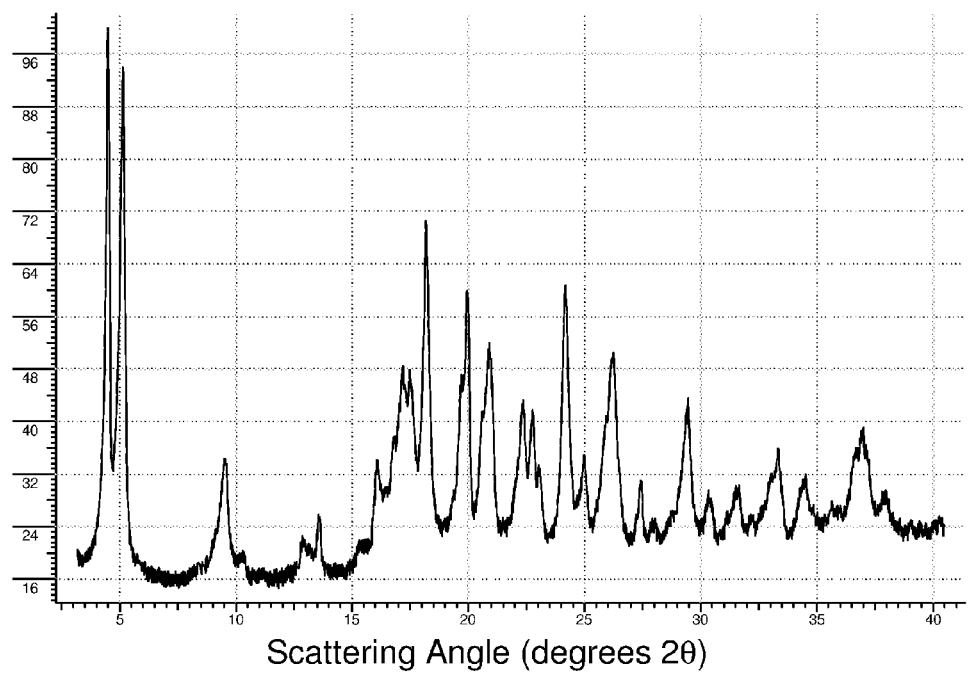
FIG. 33a is an x-ray powder diffraction pattern of the L-theanine/gluconate-zinc cocrystal.
Figure 33B:
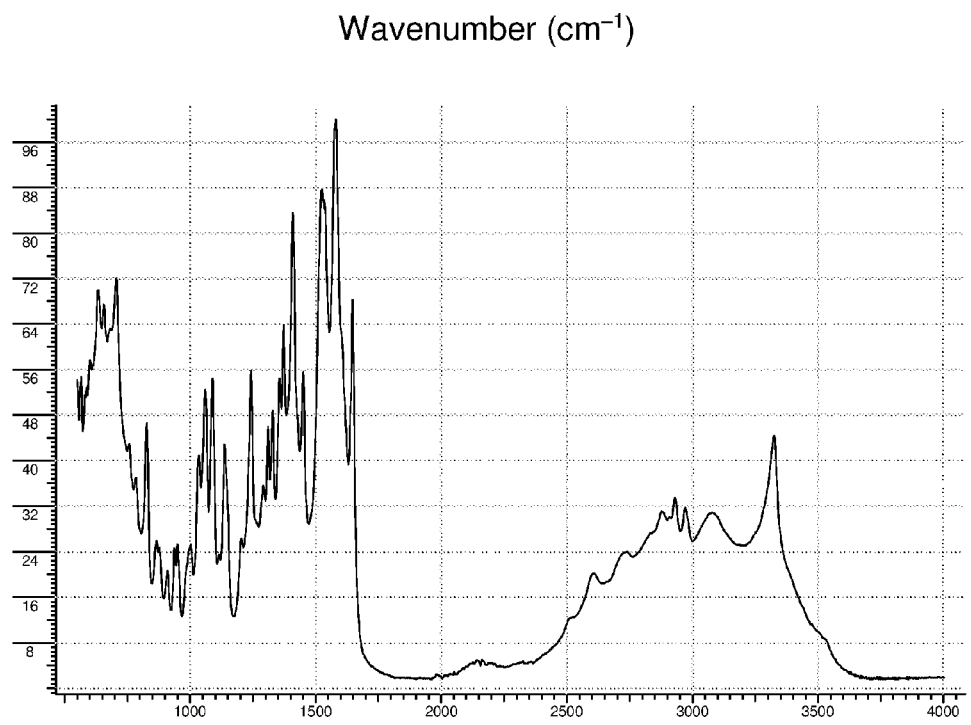
FIG. 33b is an infrared absorption spectrum of the L-theanine/gluconate-zinc cocrystal.

0.398 g of gluconate zinc (0.873 mmol) and 0.157 g of L-theanine (0.901 mmol) were weighed directly into the bowl of an agate mortar, and wetted with 70% isopropanol to form a moderately thick slurry. The slurry was thoroughly ground at the time of mixing, and then periodically re-ground until the contents were dry. The XRPD pattern of the product is shown in FIG. 33a, while the FTIR spectrum is shown in FIG. 33b. The DSC melting endotherm of the product was characterized by a peak maximum at 164° C.

Example 34

Figure 34A:
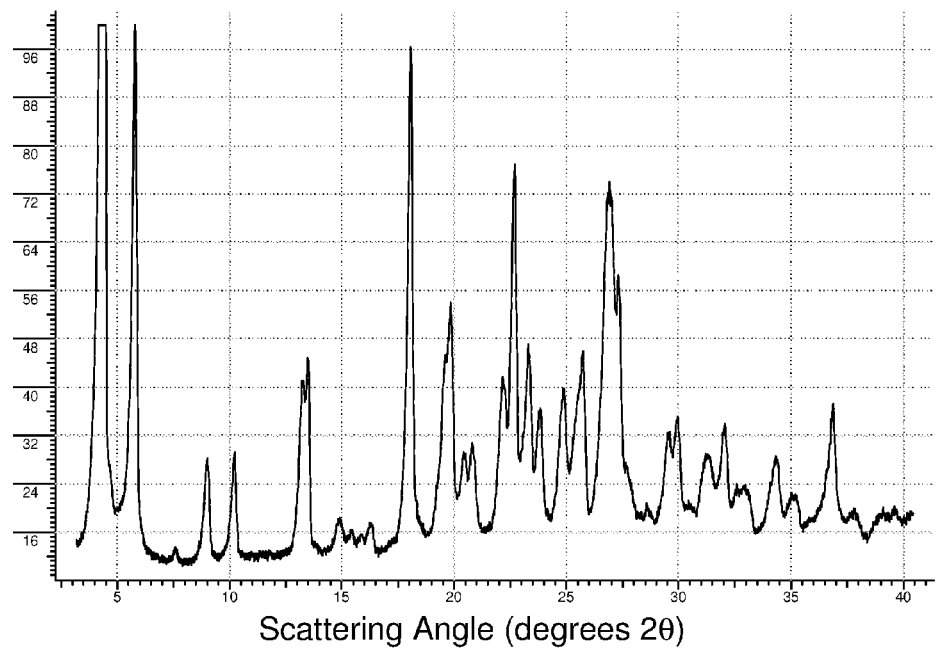
FIG. 34a is an x-ray powder diffraction pattern of the L-theanine/acyclovir cocrystal.
Figure 34B:
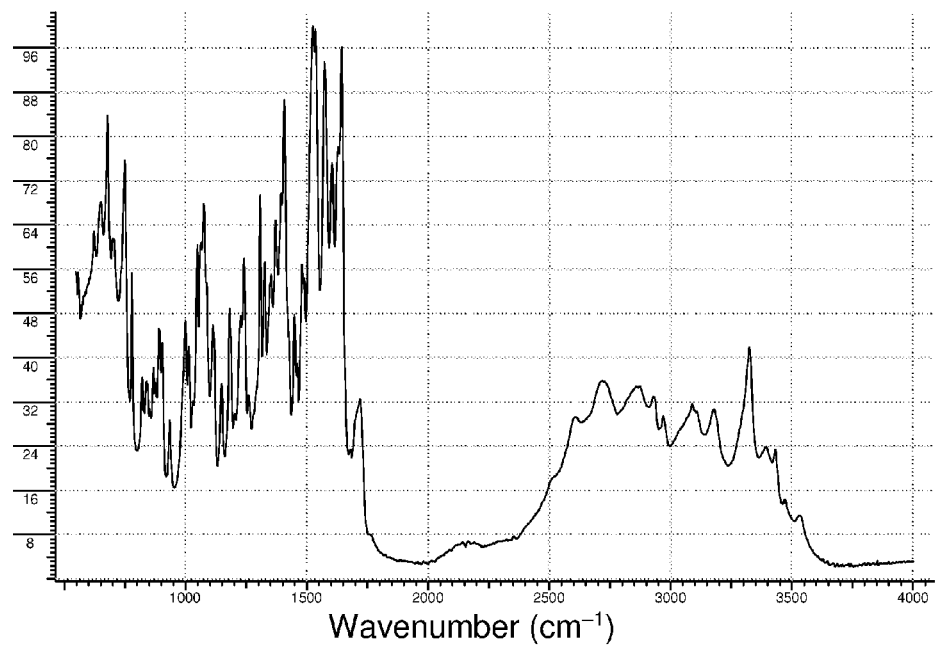
FIG. 34b is an infrared absorption spectrum of the L-theanine/acyclovir cocrystal.

0.384 g of Acyclovir (1.705 mmol) and 0.298 g of L-theanine (1.711 mmol) were weighed directly into the bowl of an agate mortar, and wetted with 70% isopropanol to form a moderately thick slurry. The slurry was thoroughly ground at the time of mixing, and then periodically re-ground until the contents were dry. The XRPD pattern of the product is shown in FIG. 34a, while the FTIR spectrum is shown in FIG. 34b. The DSC melting endotherm of the product was characterized by a peak maximum at 119° C.

Embodiments of the present invention include compositions of Theanine combined with the drugs listed in the table below. Embodiments of the present invention employing crystallization and Theanine dissolution of low solubility pharmaceuticals are highly-efficacious in the treatment of a variety of emergent conditions where improved drug delivery would benefit patients, including those presenting with, but not limited to, the conditions in the table below, with the drug(s) for treating the condition(s) listed next to the condition(s):

| Condition(s) | Drug |
| --- | --- |
| Acute pulmonary edema/congestive heart failure | Lasix |
| Acute myocardial infarction | Aspirin |
| Acute ischemic stroke | Aspirin |
| Acute allergic/anaphylactic reactions from medications, food, latex, insect bites/stings | Epinephrine |
| Cardiac arrest, acute exacerbation of asthma, ventricular fibrillation, airway obstruction | Epinephrine |
| Australian box jelly fish envenomations | Zinc gluconate |
| Neurologic emergencies including malignant hyperthermia, ecstasy intoxication/3,4-methylenedioxymethamphetamine, serotonin syndrome, 2,4-dinitrophenol poisoning. | Dantrolene sodium |

Embodiments of the present invention include compositions of Theanine combined with the drugs listed in the table below. Embodiments of the present invention employing crystallization and Theanine dissolution of low solubility pharmaceuticals are highly-efficacious in the treatment of a variety of additional conditions where improved drug delivery would benefit patients, including those presenting with, but not limited to, the conditions in the table below, with the drug(s) for treating the condition(s) listed next to the condition(s):

| Condition(s) | Drug(s) |
| --- | --- |
| Diseases/conditions associated with excessive amounts of glutamate: Spinal cord injury, stroke, traumatic brain injury, multiple sclerosis, Alzheimer's disease, Parkinson's disease, alcoholism, alcohol withdrawal, over-rapid benzodiazepine withdrawal, Huntington's disease, hypoglycemia, damage to a newborns brain caused by interrupted oxygen supply during delivery, exposure to nerve gas, and chronic nerve damage in such conditions as glaucoma, amyotrophic lateral sclerosis, and HIV dementia | Theanine |
| Parkinson's disease | Levodopa, Entacapone, Nilotinib |
| Hyperprolactinemia including amenorrhea with or without galactorrhea, infertility or hypogonadism; prolactin-secreting adenomas, acromegaly, idiopathic or postencephalitic Parkinson's disease | Bromocriptine |

-continued

| Condition(s) | Drug(s) |
|---|---|
| Hyperprolactinemic disorders, either idiopathic or due to pituitary adenomas | Cabergoline |
| Imatinib resistant chronic myelogenous leukemia, Alzheimer's disease, Parkinson's disease, Huntington's disease, dementia, amyotrophic lateral sclerosis | Nilotinib |
| Diseases/conditions associated with: Excessive amounts of glutamate, including moderate to severe Alzheimer's disease | Memantine |
| Neurodegenerative diseases such as muscle spasticity associated with multiple sclerosis, cerebral palsy, spinal cord injury and cerebrovascular accidents | Dantrolene sodium |
| Acute renal colic | (R)-Ibuprofen, IV Aspirin |
| Acute pericarditis | (R)-Ibuprofen, SL/IV aspirin |
| Dental pain, ligament injuries, | (R)-Ibuprofen, SL Aspirin |
| HIV/AIDS | Efavirenz, Zidovudine |
| *Clostridium difficile*, trichomoniasis, bacterial infections of the vagina, acne rosacea, giardiasis, amoebiasis, abscess, surgical wound infections, *helicobacter* infections, pseudomembranous enterocolitis, bacteroides infections | Metronidazole |
| Cytomegalovirus retinitis in patients who have AIDS, AIDS associated opportunistic infections, prevents CMV disease in patients who have received an organ transplant | Valganciclovir |
| Herpes simplex encephalitis, herpes labialis (cold sores), genital herpes, varicella-zoster (shingles and chickenpox), acute mucocutaneous HSV infections in immunocompromised patients, acute chickenpox in immunocompromised patients, ophthalmic herpes and herpes simplex blepharitis | Acyclovir |
| Oral *candida*/fungal infections | Fluconazole |
| Listeriosis | Ampicillin |
| Bronchitis, diphtheria, Legionnaires disease, pertussis pneumonia, dental prophylaxis | Erythromycin |
| Uncomplicated urinary tract infections, pneumocystis carinii pneumonia, toxoplasmosis, shigellosis, traveler's diarrhea | Sulfamethoxzole |
| Community-acquired pneumonia, acute exacerbations of chronic bronchitis, acute maxillary sinusitis, pharyngitis, tonsillitis, uncomplicated skin and soft tissue infections, acute bacterial otitis media | Cefdinir |
| Impetigo/soft tissue infections | Cefadroxil |
| Pharyngitis, tonsillitis, uncomplicated skin and soft tissue infections, lower respiratory infections, early stage Lyme disease | Amoxicillin |
| *Staphylococcus aureus* bacteremia including right sided endocarditis, complicated skin and skin structure gram-positive bacterial infections including MRSA | Daptomycin |
| Gout/hyperuricemia | Febuxostat |
| Heart failure, hypertension, pulmonary edema, fluid retention (edema) associate with ascites, liver cirrhosis, nephrotic syndrome | Lasix |
| Hypertension, heart failure, diabetes insipidus, fluid retention (edema) in patients with congestive heart failure, cirrhosis of the liver, nephrotic syndrome in patients taking steroids or estrogen | Hydrochlorothiazide |
| Migraine, cluster headaches | Sumatriptan, IV/SL Aspirin |
| Ramsay Hunt Syndrome | Acyclovir, Prednisone |
| Inflammation, autoimmune diseases, Bell's palsy, Hashimoto's encephalopathy, skin diseases, mild to moderate allergies, asthma, COPD, chronic inflammatory demyelinating polyneuropathy (CIDP), rheumatic disorders, allergic reactions, ulcerative colitis, Crohn's disease, adrenocortical insufficiency, thyroiditis, laryngitis, sinusitis, mild to moderate urticaria (hives), recurrent pericarditis, multiple sclerosis, nephrotic syndrome, myasthenia gravis, poison oak exposure, acute lymphoblastic leukemia, Non-Hodgkin lymphomas, Hodgkin's lymphoma, multiple myeloma and other hormone-sensitive tumors in combination with other anticancer drugs, uveitis, and sarcoidosis. | Prednisone, |
| Rhinovirus colds, Australian box jelly fish stings | Zinc gluconate |
| Acute lymphoblastic leukemia, acute myelobastic leukemia, Wilm's tumor, neuroblastoma, soft tissue and bone sarcomas, ovarian carcinoma, transitional cell bladder carcinoma, thyroid carcinoma, gastric carcinoma, Hodgkin's disease, malignant lymphoma, and bronchogenic carcinoma (small cell histologic type), and adjuvant therapy in women with evidence of axillary | Doxorubicin |

| Condition(s) | Drug(s) |
| --- | --- |
| lymph node involvement following resection of primary breast cancer | |
| Metastatic carcinoma of the colon and rectum | Irinotecan |
| Parkinson's disease and dopamine-responsive dystonias | Levodopa |
| Schizophrenia, bipolar disorder, autism | Aripiprazole |
| Pain, inflammation | Diflunisal, (R)-Ibuprofen |
| Asthma | Zafirulkast, Prednisone, |
| Hay fever | Fexofenadine |
| Stabilization of bimembrane structures | Zinc Gluconate (R)-Ibuprofen |

While a specific embodiment of the invention has been shown and described in detail to illustrate the application of the principles of the invention, it will be understood that the invention may be embodied otherwise without departing from such principles.

What is claimed is:

1. A method of treating Hodgkin's disease in a subject comprising administering an effective amount of a water-soluble composition comprising: a cocrystal containing doxorubicin and L-theanine; wherein said cocrystal is characterized as having an X-ray powder diffraction pattern with peaks (2θ) at 13.6, 18.2, 19.8, 22.0, 22.5, 25, and 38.2 degrees.

2. The method of claim 1, further comprising adding a sugar alcohol to said mixture.

3. The method of claim 2, wherein said sugar alcohol has a configuration selected from the group consisting of the L-configuration and the D-configuration.

* * * * *